United States Patent
Wang et al.

(10) Patent No.: US 9,938,347 B2
(45) Date of Patent: *Apr. 10, 2018

(54) TUMOR NECROSIS FACTOR (TNF) SUPERFAMILY RECEPTOR IGM ANTIBODIES AND USES THEREOF

(71) Applicant: IGM Biosciences A/S, Lyngby (DK)

(72) Inventors: Beatrice Tien-Yi Wang, San Francisco, CA (US); Max Allen Schwarzer, Los Altos, CA (US); Bruce Alan Keyt, Hillsborough, CA (US); Ramesh Baliga, Foster City, CA (US)

(73) Assignee: IGM BIOSCIENCES A/S, Lyngby (DK)

(*) Notice: Subject to any disclaimer, the term of this patent is extended or adjusted under 35 U.S.C. 154(b) by 0 days.

This patent is subject to a terminal disclaimer.

(21) Appl. No.: 15/638,748

(22) Filed: Jun. 30, 2017

(65) Prior Publication Data

US 2017/0320955 A1 Nov. 9, 2017

Related U.S. Application Data

(63) Continuation of application No. PCT/US2016/014153, filed on Jan. 20, 2016.

(60) Provisional application No. 62/105,323, filed on Jan. 20, 2015.

(51) Int. Cl.
C07K 16/28 (2006.01)

(52) U.S. Cl.
CPC ...... *C07K 16/2866* (2013.01); *C07K 2317/35* (2013.01); *C07K 2317/75* (2013.01)

(58) Field of Classification Search
CPC ............ C07K 16/2866; C07K 2317/35; C07K 2317/75
See application file for complete search history.

(56) References Cited

U.S. PATENT DOCUMENTS

| | | | |
|---|---|---|---|
| 5,585,089 A | 12/1996 | Queen et al. | |
| 5,693,761 A | 12/1997 | Queen et al. | |
| 5,693,762 A | 12/1997 | Queen et al. | |
| 5,939,598 A | 8/1999 | Kucherlapati et al. | |
| 6,180,370 B1 | 1/2001 | Queen et al. | |
| 7,115,717 B2 | 10/2006 | Mori et al. | |
| 7,229,617 B2 | 6/2007 | Nasoff et al. | |
| 7,229,618 B2 | 6/2007 | Johnson et al. | |
| 7,244,429 B2 | 7/2007 | Zhou et al. | |
| 7,521,048 B2 | 4/2009 | Gliniak et al. | |
| 7,790,165 B2 | 9/2010 | Zhou et al. | |
| 7,893,216 B2 | 2/2011 | Liu et al. | |
| 7,897,730 B2 | 3/2011 | Yu et al. | |
| 8,029,783 B2 | 10/2011 | Adams et al. | |
| 8,097,704 B2 | 1/2012 | Kim et al. | |
| 8,097,705 B2 | 1/2012 | Dong et al. | |
| 8,952,134 B2 | 2/2015 | Tso et al. | |
| 9,382,319 B2 | 7/2016 | Tso et al. | |
| 2006/0269555 A1 | 11/2006 | Salcedo et al. | |
| 2006/0269556 A1 | 11/2006 | Nocka et al. | |
| 2006/0269557 A1 | 11/2006 | Sherman et al. | |
| 2006/0269558 A1 | 11/2006 | Murphy et al. | |
| 2006/0269559 A1 | 11/2006 | Jackson et al. | |
| 2006/0269560 A1 | 11/2006 | Savarino | |
| 2006/0269561 A1 | 11/2006 | Paterson et al. | |
| 2006/0269562 A1 | 11/2006 | Bain et al. | |
| 2006/0269563 A1 | 11/2006 | Pizza et al. | |
| 2006/0269564 A1 | 11/2006 | Emery et al. | |
| 2006/0269565 A1 | 11/2006 | Yoshinaga et al. | |
| 2006/0269566 A1 | 11/2006 | Punnonen et al. | |
| 2006/0269567 A1 | 11/2006 | Yuen | |
| 2006/0269568 A1 | 11/2006 | Chung et al. | |
| 2006/0269569 A1 | 11/2006 | Yuen | |
| 2009/0053252 A1 | 2/2009 | Tschopp et al. | |
| 2011/0008354 A1 | 1/2011 | Adams et al. | |
| 2014/0294825 A1 | 10/2014 | Tso et al. | |
| 2015/0139997 A1 | 5/2015 | Vermot-Desroches et al. | |
| 2015/0353638 A1 | 12/2015 | Zheng et al. | |
| 2016/0222132 A1 | 8/2016 | Keyt et al. | |
| 2016/0368971 A1 | 12/2016 | Keyt et al. | |
| 2017/0183409 A1 | 6/2017 | Keyt et al. | |
| 2017/0283510 A1 | 10/2017 | Keyt et al. | |
| 2018/0009897 A1 | 1/2018 | Wang et al. | |

FOREIGN PATENT DOCUMENTS

| | | |
|---|---|---|
| EP | 2636736 A1 | 9/2013 |
| WO | 2008/025516 A2 | 3/2008 |
| WO | 2014/063368 A1 | 5/2014 |
| WO | 2014/161845 A1 | 10/2014 |
| WO | 2016/055432 A2 | 4/2016 |
| WO | 2016/122702 A1 | 8/2016 |
| WO | 2017/059380 A1 | 4/2017 |
| WO | 2017/059387 A1 | 4/2017 |
| WO | 2018/017761 A1 | 1/2018 |
| WO | 2018/017763 A1 | 1/2018 |

(Continued)

OTHER PUBLICATIONS

International Search Report and Written Opinion for PCT/US2016/014153 dated Apr. 19, 2016.
Aggarwal et al., "Historical Perspective on Tumor Necrosis Factor and Its Superfamily: 25 Years Later, a Golden Journey", Blood, 2012, pp. 651-665, vol. 119, No. 3.
Valley et al., "Tumor Necrosis Factor-Related Apoptosis-Inducing Ligand (TRAIL) Induces Death Receptor 5 Networks That Are Highly Organized", Journal of Biological Chemistry, 2012, pp. 21265-21278, vol. 287.
Lewis et al., "Open and Closed Conformations of the Isolated Transmembrane Domain of Death Receptor 5 Support a New Model of Activation", Biophysical Journal, 2014, pp. L21-L24, vol. 106.
Innes et al., "Significance of the Metastasis-Inducing Protein AGR2 for Outcome in Hormonally Treated Breast Cancer Patients", British Journal of Cancer, Apr. 2006, pp. 1057-1065, vol. 94, No. 7.
Reck et al., "A Randomized, Double-Blind, Placebo-Controlled Phase 2 Study of Tigatuzumab (CS-1008) in Combination with Carboplatin/Paclitaxel in Patients with Chemotherapy-Naïve Metastatic/Unresectable Non-Small Cell Lung Cancer", Dec. 2013, pp. 441-448, vol. 82, Issue 3.

(Continued)

*Primary Examiner* — Robert S Landsman
(74) *Attorney, Agent, or Firm* — Thompson Coburn LLP

(57) ABSTRACT

This disclosure provides dimeric, pentameric, and hexameric Tumor Necrosis Factor (TNF) superfamily receptor protein binding molecules and methods of using such binding molecules to direct apoptosis-mediated killing of TNF receptor-expressing cells.

16 Claims, 17 Drawing Sheets

(56) References Cited

FOREIGN PATENT DOCUMENTS

Figure 1B:
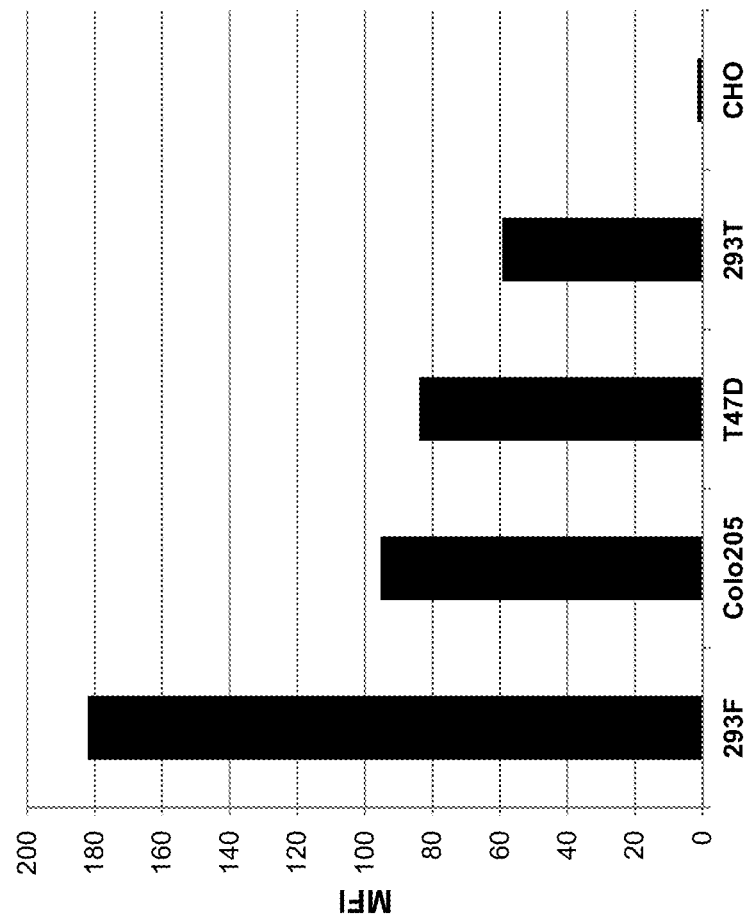

| WO | 2018/017888 A1 | 1/2018 |
|---|---|---|
| WO | 2018/017889 A1 | 1/2018 |

OTHER PUBLICATIONS

Brummel et al., "Probing the Combing Site of an Anti-Carbohydrate Antibody by Saturation-Mutagenesis: Role of be Heavy-Chain CDR3 Residues", Biochemistry, 1993, pp. 1180-1187, vol. 32.

Kobayashi et al., "Tryptophan H33 Plays an Important Role in Pyrimidine (6-4) Pyrimidone Photoproduct Binding by a High-Affinity Antibody", Protein Engineering, Design and Selection, 1999, pp. 879-884, vol. 12, No. 10.

Burks et al, "In vitro Scanning Saturation Mutagenesis of an Antibody Binding Pocket", Proceedings of the National Academy of Sciences USA, 1997, pp. 412-417, vol. 94.

Ströhlein et al., "The Trifunctional Antibody Catumaxomab in Treatment of Malignant Ascites and Peritoneal Carcinomatosis", 2010, pp. 1387-1394, vol. 6.

Mabry et al., "Therapeutic Bispecific Antibodies: The Selection of Stable Single-Chain Fragments to Overcome Engineering Obstacles", IDrugs, 2010, pp. 543-549, vol. 13.

Li et al., "Expression of TRAIL, DR4, and DR5 in Bladder Cancer: Correlation with Response to Adjuvant Therapy end Implications of Prognonsis", Urology, 2012, pp. e7-e15, vol. 79, No. 4.

Jiang et al, Apoptosis-Inducing Effect of the DR5 Monoclonal Antibody, D-6, Alone or in Combination with Cisplatin, on A2780 Ovarian Cancer Cells, Molecular Medicine Reports, May 3, 2012, pp. 316-320, vol. 6, No. 2.

Lim et al., "Lipid Raft-Dependent Death Receptor 5 (DR5) Expression and Activation are Critical for Ursodeoxycholic Acid-Induced Apoptosis in Gastric Cancer Cells", Carcinogenesis, 2011, pp. 723-731, vol. 32, No. 5.

Rajeshkumar et al., "A Combination of DR5 Agonistic Monoclonal Antibody with Gemcitabine Targets Pancreatic Cancer Stem Cells and Results in Long-Term Disease Control in Human Pancreatic Cancer Model", Molecular Cancer Therapeutics, Sep. 2010, pp. 2582-2592, vol. 9, No. 9.

Chen et al, "TRAIL Induces Apoptosis in Oral Squamous Carcinoma Cells: A Crosstalk with Oncogenic Ras Regulated Cell Surface Expression of Death Receptor 5", Oncotarget, Feb. 2013, pp. 206-217, vol. 4, No. 2.

Ichikawa et al, "Tumoricidal Activity of a Novel Anti-Human DR5 Monoclonal Antibody Without Hepatocyte Cytotoxicity", Nature Medicine, Aug. 2001, pp. 954-960, vol. 7, No. 8.

Elgueta et al, "Molecular Mechanism and Function of CD40/CD40L Engagement in the Immune System", Immunological Reviews, May 2009, pp. 1-31, vol. 229, No. 1.

Schaer et al., "Targeting Tumor-Necrosis Factor Receptor Pathways for Tumor Immunotherapy", Journal of ImmunoTherapy of Cancer, 2014, pp. 1-9, vol. 2, No. 7.

Allen et al. "Targeting TRAIL Death Receptor 4 with Trivalent DR4 Atrimer Complexes," Molecular Cancer Therapeutics, Oct. 2012, pp. 2087-2095, vol. 11.

Brunker et al. "RG7386, a Novel Tetravalent FAP-DR5 Antibody, Effectively Triggers FAP-Dependent, Avidity-Driven DR5 Hyperclustering and Tumor Cell Apoptosis," Molecular Cancer Therapeutics, May 2016, pp. 946-957, vol. 15, No. 5.

De Jong et al., "A Novel Platform for the Potentiation of Therapeutic Antibodies Based on Antigen-Dependent Formation of IgG Hexamers at the Cell Surface", PLOS Biology, Jan. 6, 2016, pp. 1-24.

Durham et al, "GITR Ligand Fusion Protein Agonist Enhances the Tumor Antigen-Specific CD8 T-Cell Response and Leads to Long-Lasting Memory", Journal for ImmunoTherapy of Cancer, 2017, pp. 1-12, vol. 5, No. 47.

Gieffers et al. "APG350 Induces Superior Clustering of TRAIL Receptors and Shows Therapeutic Antitumor Efficacy Independent of Cross-Linking via Fc? Receptors," Molecular Cancer Therapeutics, 2013, pp. 2735-2747, vol. 12, No. 12.

Guo et al, "Identification of Novel Epitopes with Agonistic Activity for the Development of Tumor Immunotherapy Targeting TRAIL-R1", Journal of Cancer, 2017, 2542-2553, vol. 8, No. 13.

Huet et al "Multivalent Nanobodies Targeting Death Receptor 5 Elicit Superior Tumor Cell Killing Through Efficient Caspase Induction," mAbs, 2014, pp. 1560-1570, vol. 6, No. 6.

Leyland et al, "A Novel Murine GITR Ligand Fusion Protein Induces Antitumor Activity as a Monotherapy That Is Further Enhanced in Combination with an OX40 Agonist", Clinical Cancer Research, Jul. 1, 2017, pp. 3416-3427, vol. 23, No. 13.

Liu et al., "The Tetravalent Anti-DR5 Antibody Without Cross-Linking Direct Induces Apoptosis of Cancer Cells", Biomedicine & Pharmacotherapy, 2015, pp. 41-45, vol. 70.

Morris et al., "Development and Characterization of Recombinant Human Fc:OX40L Fusion Protein Linked via a Coiled-Coil Trimerization Domain", Molecular Immunology, May 2007, pp. 3112-3121, vol. 44, No. 12.

Piao et al "TRAIL-Receptor 1 IgM Antibodies Strongly Induce Apoptosis in Human Cancer Cells in vitro and in vivo," Oncoimmunology, 2016, pp. 1-9 e1131380, vol. 5, No. 5.

Swers et al. "Multivalent Scaffold Proteins as Superagonists of TRAIL Receptor 2-Induced Apoptosis," Molecular Cancer Therapeutics, Jul. 2013, pp. 1235-1244, vol. 12, No. 7.

Tigue et al. "MEDI1873, a Potent, Stabilized Hexameric Agonist of Human GITR with Regulatory T-Cell Targeting Potential," Oncoimmunology, 2017, pp. 1-16 e1280645, vol. 6, No. 3.

Wang et al. "Pentamerisation of a scFv Directed Against TRAIL Receptor 2 Increases its Antitumour Efficacy," Immunology and Cell Biology, 2013, pp. 360-367, vol. 91.

TUMOR NECROSIS FACTOR (TNF) SUPERFAMILY RECEPTOR IGM ANTIBODIES AND USES THEREOF

CROSS-REFERENCE TO RELATED APPLICATIONS

This application is a bypass continuation of PCT Application No. PCT/US2016/014153, filed Jan. 20, 2016, which claims benefit to U.S. Provisional Appl. No. 62/105,323, filed on Jan. 20, 2015; the content of each are hereby incorporated by reference in their entireties. This application is related to U.S. application Ser. No. 15/544,873, which is the 371 National Phase of PCT Application No. PCT/US2016/014153, filed Jan. 20, 2016, which claims benefit to U.S. Provisional Appl. No. 62/105,323, filed on Jan. 20, 2015.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Jun. 28, 2017, is named 57912-167202_SL_June_2017.txt and is 154,148 bytes in size.

BACKGROUND

Since the advent of humanized antibodies, the therapeutic use of antibodies such as Rituxan® (rituximab), Herceptin® (trastuzumab) and Avastin® (bevacizumab), has revolutionized the fields of medicine, including oncology, the treatment of inflammatory disorders, such as rheumatoid arthritis, and many other indications. In the United States, more than 30 human or humanized antibodies have been approved for clinical use, and more than 600 new antibodies or antibody-like molecules are in various stages of development. Some antibodies have antagonistic function on soluble target molecules such as vascular endothelial growth factor (VEGF) or tumor necrosis factor (TNF), whose actions are part of the pathologic process of a disease. Alternatively, antibodies can bind, block and/or induce destruction of pathologic cells in certain diseases, such as cancer. The main functions of these therapeutic antibodies are binding through the Fab region, and recruitment of effector function via the Fc domain (which also mediates the long circulating half-life of antibodies). One of the major advantages of antibodies compared to small molecule drugs can be their exquisite specificity. Antibodies can very accurately target selected protein antigens, such as oncogenes, to the exclusion of very similar homologs, allowing for benign safety profiles. Hence, antibodies are well characterized for specific single targeting function.

As the field has progressed, antibody function has been enhanced through creative means of protein engineering, such as to provide higher affinity, longer half-life, and/or better tissue distribution, as well as combination of small and large molecule technologies for increased focus of cell destruction via toxic payload delivery (e.g. antibody-drug conjugates). Another approach to improving antibody function takes advantage of the multivalent binding capabilities of the immunoglobulin A (IgA) or immunoglobulin M (IgM) structure which allows one IgA or IgM molecule to bind multiple antigens. Heavy and light chain variable domains of interest can be expressed as an IgA or IgM isotype antibody, thereby creating a multimeric binding molecule with the same specificity as a monomeric antibody, e.g., an IgG antibody.

The multivalent nature of IgA or IgM molecules presents a useful tool for application to specific biological systems in which multiple components necessarily must be bound simultaneously to transmit biological signals. For instance, many receptor proteins on the surface of eukaryotic cells require the simultaneous activation of multiple monomers or subunits to achieve activation and transmission of a biological signal across a cell membrane, to the cytoplasm of the cell.

One such system of cell surface protein receptors requiring multimerization prior to, or commensurate with, activation is found in the Tumor Necrosis Factor (TNF) superfamily of receptor proteins. Within this superfamily of receptor proteins are members which, upon activation, transmit a signal to the nucleus of the cell causing apoptosis. Other family members of this superfamily cause activation of NF-κB, apoptosis pathways, extracellular signal-regulated kinase (ERK), p38 mitogen-activated protein kinase (p38MAPK), and c-Jun N-terminal kinase (JNK). Examples of TNF superfamily receptor members which regulate apoptosis of the cell when activated are the following: TNFR1 (DR1), TNFR2, TNFR1/2, CD40 (p50), Fas (CD95, Apo1, DR2), CD30, 4-1BB (CD137, ILA), TRAILR1 (DR4, Apo2), DR5 (TRAILR2), TRAILR3 (DcR1), TRAILR4 (DcR2), OPG (OCIF), TWEAKR (FN14), LIGHTR (HVEM), DcR3, DR3, EDAR, and XEDAR. (See, Aggarwal et al., *Blood*, 119:651-665, 2012).

More particularly, it is postulated that activation of the TNF superfamily receptor protein members mentioned above requires that at least three non-interacting receptor monomers be cross-linked, e.g., by a ligand, to form a stabilized receptor trimer, resulting in signal transduction across the cell membrane. Clustering of these TNF superfamily receptor protein trimers into "rafts" of trimers has been observed and has been postulated to lead to more effective activation of this TNF superfamily receptor protein-dependent signaling cascade. (See, Valley et al., *J. Biol. Chem.*, 287(25):21265-21278, 2012). Additional modes of activation have been discussed. (See, for instance, Lewis et al., *Biophys. J.*, 106(6):L21-L24, 2014).

Signaling through certain of the TNF superfamily receptor proteins noted above can lead to cell apoptosis. In the treatment of cancer, one therapeutic strategy is to activate an apoptotic signaling cascade in cancer cells, thereby halting progression. One manner in which this can be accomplished is by the binding of TNF superfamily receptor proteins expressed (or over-expressed) in cancer cells with a multivalent or multimeric agonist binding molecule, which can promote receptor trimerization and activation, leading to apoptosis. One TNF superfamily receptor protein that is activated upon cross-linking resulting in apoptosis is DR5 (TRAILR2).

Interest—in DR5 is heightened due to the finding that it is expressed at a higher level in various cancers than in normal tissue, such as bladder cancer (Y et al., *Urology*, 79(4):968.e7-15, 2012), gastric cancer (Lim et al., *Carcinogen.*, 32(5):723-732, 2011), ovarian cancer (Jiang et al., *Mol. Med. Rep.*, 6(2):316-320, 2012), pancreatic ductal adenocarcinoma (Rajeshkumar et al., *Mol. Cancer Ther.*, 9(9):2583-92, 2010), oral squamous cell carcinoma (Chen et al. *Oncotarget* 4:206-217, 2013) and non-small cell lung cancer (Reck et al., *Lung Canc.*, 82(3):441-448, 2013). It is of additional importance to the medical community that the observed higher level of expression of this family of receptor proteins, especially family member DR5, occurs in some of the most difficult to detect and treat cancers, such as pancreatic and gastric cancer.

While certain monoclonal antibodies, such as Tigatuzumab (CS-1008, Daiichi Sankyo Co. Ltd., disclosed in U.S. Pat. No. 7,244,429, VH and VL presented herein as SEQ ID NO: 7 and SEQ ID NO: 8, respectively), have been found to be effective in vitro and in vivo even without additional cross-linkers added, these antibodies have not resulted in significant clinical efficacy. (See, Reck et al., 2013). Examples of such anti-DR5 agonistic monoclonal IgG antibodies are Conatumumab (Amgen, described in U.S. Pat. No. 7,521,048, VH and VL presented herein as SEQ ID NO: 5 and SEQ ID NO: 6, respectively), Drozitumab (Genentech, as described in U.S. Pat. No. 8,029,783, VH and VL presented herein as SEQ ID NO: 3 and SEQ ID NO: 4, respectively), and Lexatumumab (Human Genome Sciences, as disclosed in U.S. Patent Application Publication No. 2006/0269555, VH and VL presented herein as SEQ ID NO: 1 and SEQ ID NO: 2, respectively).

Better binding molecules are needed to achieve the benefits of the basic research performed which provided a critical understanding of this subset of the TNF superfamily receptor proteins. Additional binding molecules are disclosed herein which, based on the understanding of the underlying biochemical mechanism of the TNF superfamily of receptor proteins, are capable of addressing this need.

SUMMARY

This disclosure provides a multimeric, e.g., dimeric, pentameric, or hexameric binding molecule including two, five, or six bivalent binding units or variants or fragments thereof, where each binding unit includes two IgA or IgM heavy chain constant regions or fragments thereof, each associated with an antigen-binding domain, where at least three of the antigen-binding domains of the binding molecule specifically and agonistically bind to a tumor necrosis factor (TNF) superfamily receptor protein that can induce apoptosis of a cell expressing the TNF superfamily receptor protein, and where the binding molecule can cross-link at least three identical TNF superfamily receptor proteins expressed on the surface of a cell, thereby inducing apoptosis of the cell.

In certain aspects a dimeric, pentameric, or hexameric binding molecule as provided herein can induce TNF superfamily receptor-mediated apoptosis in a TNF receptor superfamily-expressing cell at a higher potency than an equivalent amount of a bivalent IgG antibody or fragment thereof, which also specifically binds to and agonizes the same TNF superfamily receptor protein. In certain aspects, the three or more antigen-binding domains that specifically bind to and agonize the TNF superfamily receptor protein do not cross-react with other TNF superfamily receptor proteins. In certain aspects, the three or more antigen-binding domains that specifically bind to and agonize the TNF superfamily receptor protein can cross-react with other TNF superfamily receptor proteins.

In certain aspects, a dimeric, pentameric, or hexameric binding molecule as provided herein can include at least three, at least four, at least five, at least six, at least seven, at least eight, at least nine, at least ten, at least eleven, or twelve antigen-binding domains that specifically and agonistically bind to a TNF superfamily receptor protein expressed on the surface of the cell, thereby inducing apoptosis of the cell. In certain aspects, the at least three, at least four, at least five, at least six, at least seven, at least eight, at least nine, at least ten, at least eleven, or twelve antigen-binding domains bind to the same extracellular epitope of a single type of TNF superfamily receptor molecule expressed on the surface of the cell. In certain aspects, at least three, at least four, at least five, at least six, at least seven, at least eight, at least nine, at least ten, at least eleven, or twelve antigen-binding domains each specifically bind one of a group of two or more different extracellular epitopes of a single type of TNF superfamily receptor molecule expressed on the surface of the cell.

The binding units of a dimeric, pentameric, or hexameric binding molecule provided herein can be human, humanized, or chimeric immunoglobulin binding units.

In certain aspects, a dimeric, pentameric, or hexameric binding molecule as provided herein can bind to, without limitation, TNFR1 (DR1), TNFR2, TNFR1/2, CD40 (p50), Fas (CD95, Apo1, DR2), CD30, 4-1BB (CD137, ILA), TRAILR1 (DR4, Apo2), TRAILR2 (DR5), TRAILR3 (DcR1), TRAILR4 (DcR2), OPG (OCIF), TWEAKR (FN14), LIGHTR (HVEM), DcR3, DR3, EDAR, and XEDAR. In certain aspects, the binding molecule includes at least three antigen-binding domains that can specifically and agonistically bind to DR5. In certain aspects, the antigen binding domains do not bind to DR4, DcR1, or DcR2. In certain aspects the binding molecule includes at least three antigen-binding domains that can also specifically bind to DR4. In certain aspects, DR5 is expressed on a cancer cell.

In certain aspects a dimeric, pentameric, or hexameric binding molecule is provided where at least one, at least two, at least three, at least four, at least five, at least six, at least seven, at least eight, at least nine, at least ten, at least eleven, or twelve antigen-binding domains include a heavy chain variable region (VH) and a light chain variable region (VL), where the VH and VL include six immunoglobulin complementarity determining regions HCDR1, HCDR2, HCDR3, LCDR1, LCDR2, and LCDR3, where the HCDR1, HCDR2, HCDR3, LCDR1, LCDR2, and LCDR3 include the CDRs of an antibody including the VH and VL amino acid sequences SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; SEQ ID NO: 47 and SEQ ID NO: 48; SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 82 and SEQ ID NO: 83; SEQ ID NO: 84 and SEQ ID NO: 85; SEQ ID NO: 86 and SEQ ID NO: 87; or SEQ ID NO: 88 and SEQ ID NO: 89; respectively, or the ScFv sequence SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73 or the six CDRs with one or two amino acid substitutions in one or more of the CDRs.

In certain aspects a dimeric, pentameric, or hexameric binding molecule is provided where at least one, at least two, at least three, at least four, at least five, at least six, at least seven, at least eight, at least nine, at least ten, at least eleven, or twelve antigen-binding domains include an antibody VH and a VL, where the VH and VL include amino acid sequences at least 80%, at least 85%, at least 90%, at least 95% or 100% identical to SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; SEQ ID NO: 47 and SEQ ID NO: 48; SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 82 and SEQ ID NO: 83; SEQ ID NO: 84 and SEQ ID NO: 85; SEQ ID NO: 86 and SEQ ID NO: 87; or SEQ ID NO: 88 and SEQ ID NO: 89; respectively, or where the VH and VL are contained in an ScFv with an amino acid sequence at least 80%, at least 85%, at least 90%, at least 95% or 100% identical to SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

In certain aspects, the binding molecule as provided herein as a dimeric IgA molecule further including a J chain In certain aspects, the binding molecule as provided herein is a pentameric IgM molecule further including a J chain.

In certain aspects, the binding molecule as provided herein is a hexameric IgM molecule.

The disclosure further provides a composition including a dimeric, pentameric, or hexameric binding molecule as provided herein.

The disclosure further provides a polynucleotide that includes a nucleic acid sequence encoding a polypeptide subunit, e.g., a heavy or light chain of a binding molecule provided herein. In certain aspects, the polypeptide subunit includes a human IgA or IgM constant region or fragment thereof fused to the C-terminal end of a VH including: (a) HCDR1, HCDR2, and HCDR3 regions including the CDRs contained in the VH amino acid sequence SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 82, SEQ ID NO: 84, SEQ ID NO: 86, or SEQ ID NO: 88, or in the ScFv amino acid sequence SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73; or the CDRs contained in the VH amino acid sequence SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 82, SEQ ID NO: 84, SEQ ID NO: 86, or SEQ ID NO: 88, or in the ScFv amino acid sequence SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73 with one or two single amino acid substitutions in one or more of the HCDRs; or (b) an amino acid sequence at least 80%, at least 85%, at least 90%, at least 95% or 100% identical to SEQ ID NO: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 82, SEQ ID NO: 84, SEQ ID NO: 86, or SEQ ID NO: 88, or the VH portion of an ScFv with the amino acid sequence SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

In certain aspects, the polypeptide subunit includes a light chain constant region or fragment thereof fused to the C-terminal end of the polypeptide subunit to an antibody VL portion of the antigen-binding domain of the dimeric, pentameric, or hexameric binding molecule. In certain aspects the polypeptide subunit includes a human kappa or lambda light chain constant region or fragment thereof fused to the C-terminal end of a VL including: (a) LCDR1, LCDR2, and LCDR3 regions including the CDRs contained in the VL amino acid sequence SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 83, SEQ ID NO: 85, SEQ ID NO: 87, or SEQ ID NO: 89, or in the ScFv amino acid sequence SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73; or the CDRs contained in the VL amino acid sequence SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 83, SEQ ID NO: 85, SEQ ID NO: 87, or SEQ ID NO: 89, or in the ScFv amino acid sequence SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73, with one or two single amino acid substitutions in one or more of the LCDRs; or (b) an amino acid sequence at least 80%, at least 85%, at least 90%, at least 95% or 100% identical to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 83, SEQ ID NO: 85, SEQ ID NO: 87, or SEQ ID NO: 89, or the VL portion of an ScFv with the amino acid sequence SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

The disclosure further provides a composition including one, two, or more polynucleotides as provided herein. In certain aspects a composition is provided where the polynucleotides are on separate vectors. Such vectors are provided. In certain aspects, a composition is provided where the polynucleotides are on a single vector. Such a vector is provided. In certain aspects, the composition further includes a polynucleotide including a nucleic acid sequence encoding a J chain, or fragment thereof, or variant thereof.

The disclosure also provides a host cell including a polynucleotide as provided herein, a composition as provided herein, or the vector or vectors provided herein, where the host cell can express a dimeric, pentameric, or hexameric binding molecule as provided herein. The disclosure further provides a method of producing the binding molecule as provided herein, where the method includes culturing the host cell and recovering the binding molecule.

In another aspect, the disclosure provides a method of inducing TNF superfamily receptor-mediated apoptosis in a TNF superfamily receptor-expressing cell, where the method includes contacting the TNF superfamily receptor-expressing cell with a dimeric, pentameric, or hexameric binding molecule as provided herein.

In another aspect, the disclosure provides a method of inducing TNF superfamily receptor lipid raft formation in a TNF superfamily receptor-expressing cell, including contacting the TNF superfamily receptor-expressing cell with a dimeric, pentameric, or hexameric binding molecule as provided herein.

In another aspect, the disclosure provides a method of treating cancer, where the method includes administering to a subject in need thereof an effective amount of a dimeric, pentameric, or hexameric binding molecule as provided herein, where the cancer cells express a TNF superfamily receptor with apoptotic activity. In certain aspects the multimeric binding molecule can induce greater apoptosis of cancer cells than non-cancer cells, e.g., normal hepatocytes, e.g., normal human hepatocytes. In certain aspects, the TNF superfamily receptor is DR5. In certain aspects, the subject is human.

BRIEF DESCRIPTION OF THE DRAWINGS/FIGURES

Figure 1A:
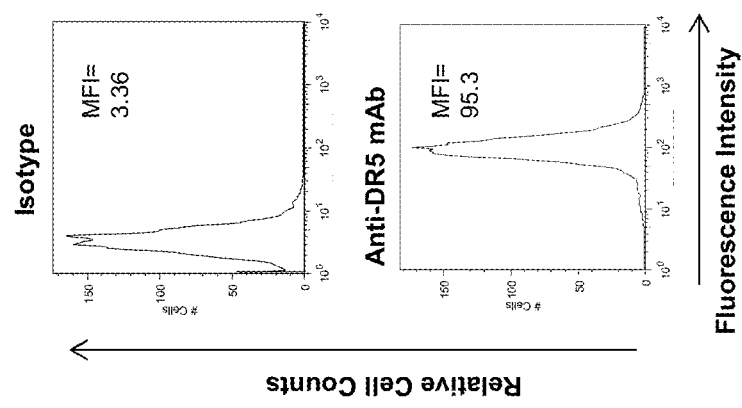

FIG. 1A-FIG. 1B: DR5 Expression Profiling on Cell Lines. (FIG. 1A) Surface expression of human DR5 on Colo205 cells, measured by flow cytometry; (FIG. 1B) Mean fluorescence intensity (MFI) of DR5 expression on a panel of cell lines.

Figure 2:
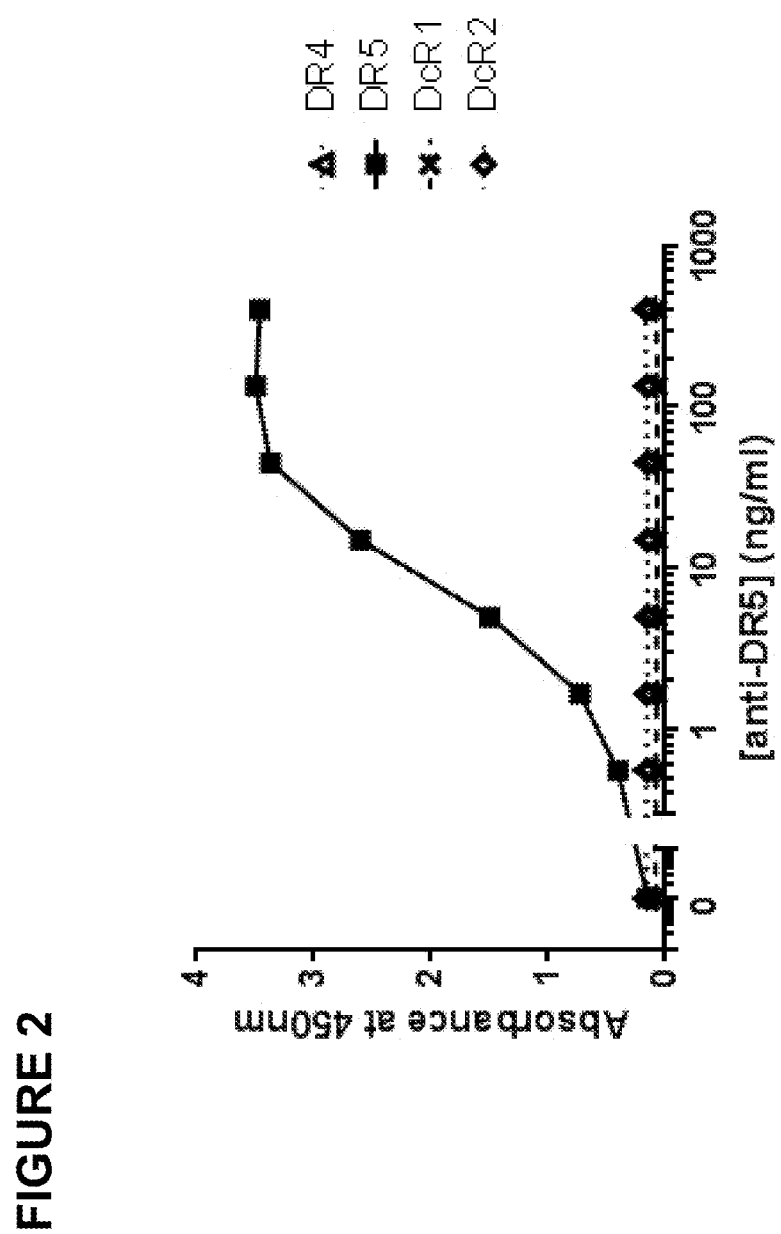

FIG. 2: Anti-DR5 mAb is Specific for DR5. Anti-human DR5 mAb binds specifically to DR5, and not DR4 or decoy receptors DcR1 and DcR2 as measured by ELISA.

Figure 3:
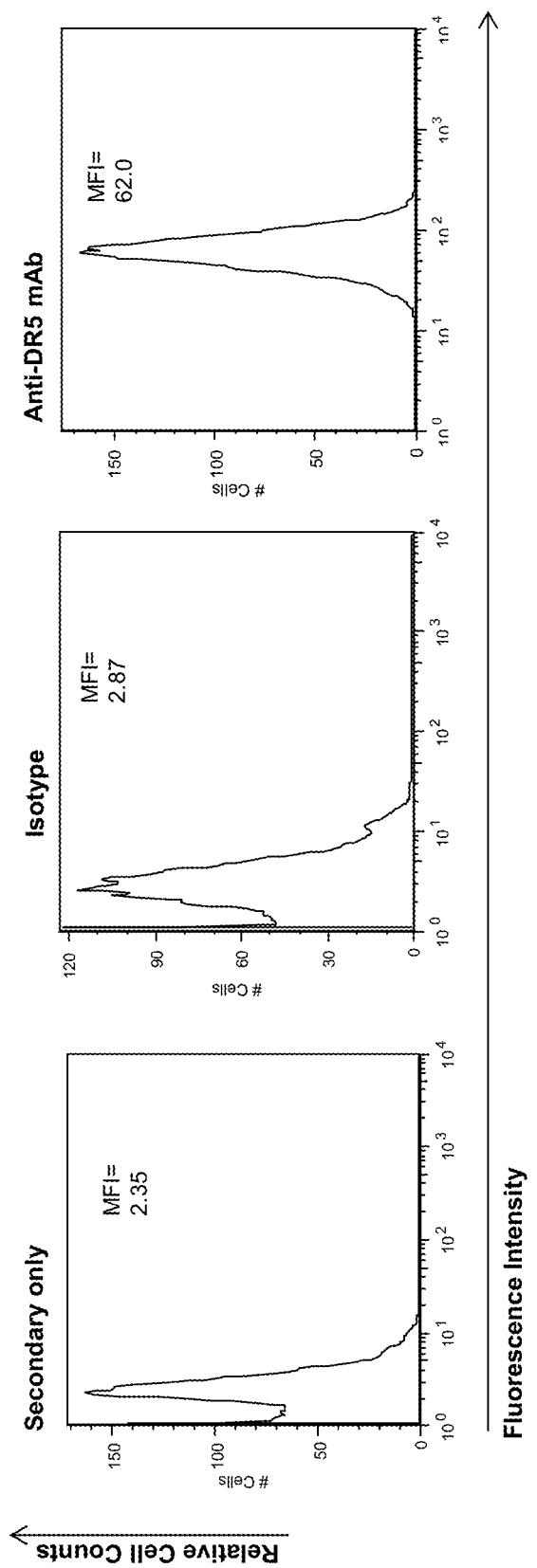

FIG. 3: Anti-DR5 mAb Cell Binding. Anti-human DR5 mAb or Isotype control were incubated with Colo205 cells for 15 minutes, washed, and stained with an allophycocyanin-conjugated secondary antibody. Binding was measured by flow cytometry.

Figure 4:
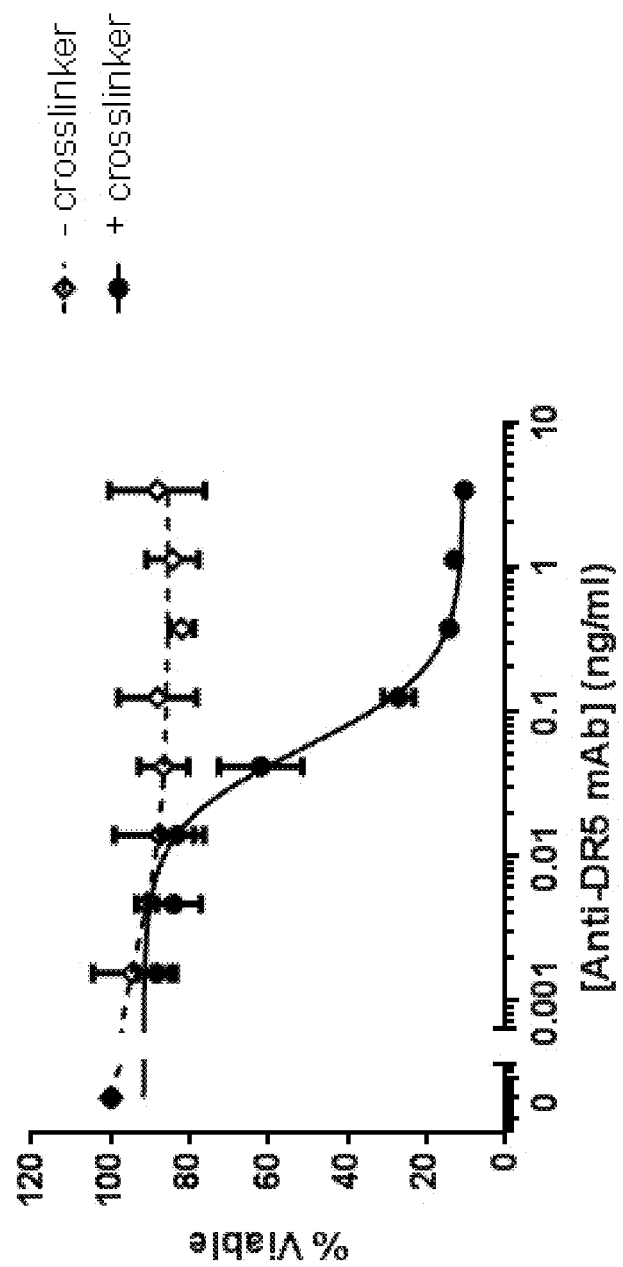

FIG. 4: Anti-DR5 IgG Requires Crosslinker for Cytotoxicity. Colo205 cells were incubated with anti-DR5 mAb in the absence or presence of crosslinker. Cell viability was measured after 24 hours. Isotype control displayed no cytotoxicity with or without crosslinker (data not shown).

Figure 5:
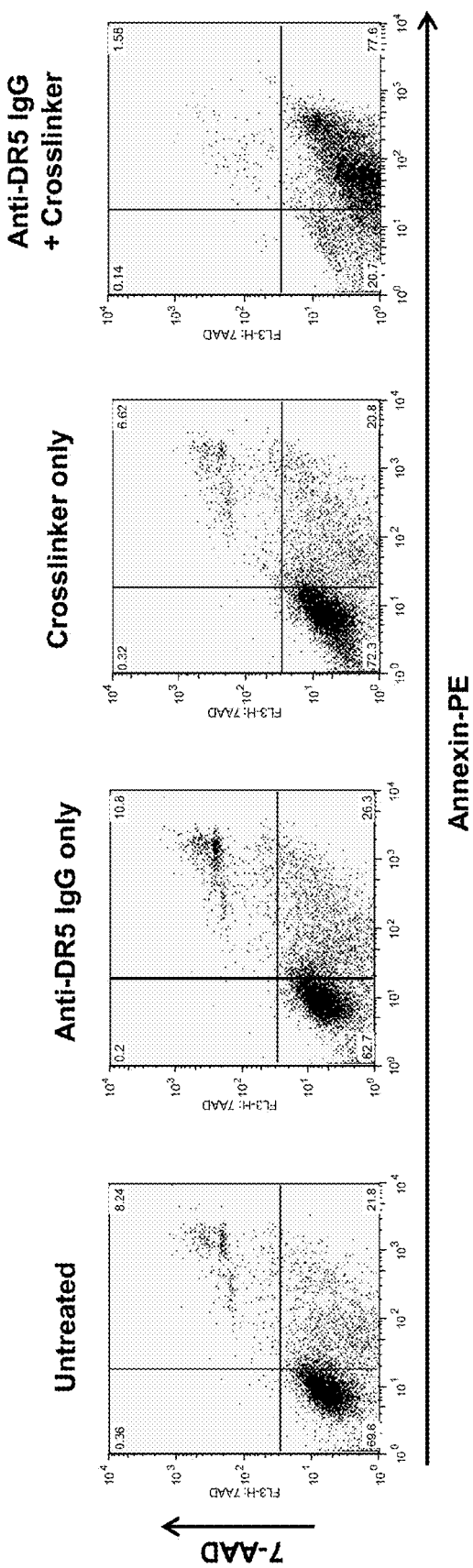

FIG. 5: Anti-DR5 IgG Requires Crosslinker for Apoptosis. Colo205 cells were incubated with 5 µg/mL anti-DR5 mAb in the absence or presence of crosslinker. After 4 hour treatment, Annexin V and 7-AAD were used to measure apoptotic and dead cells, respectively.

Figure 6:
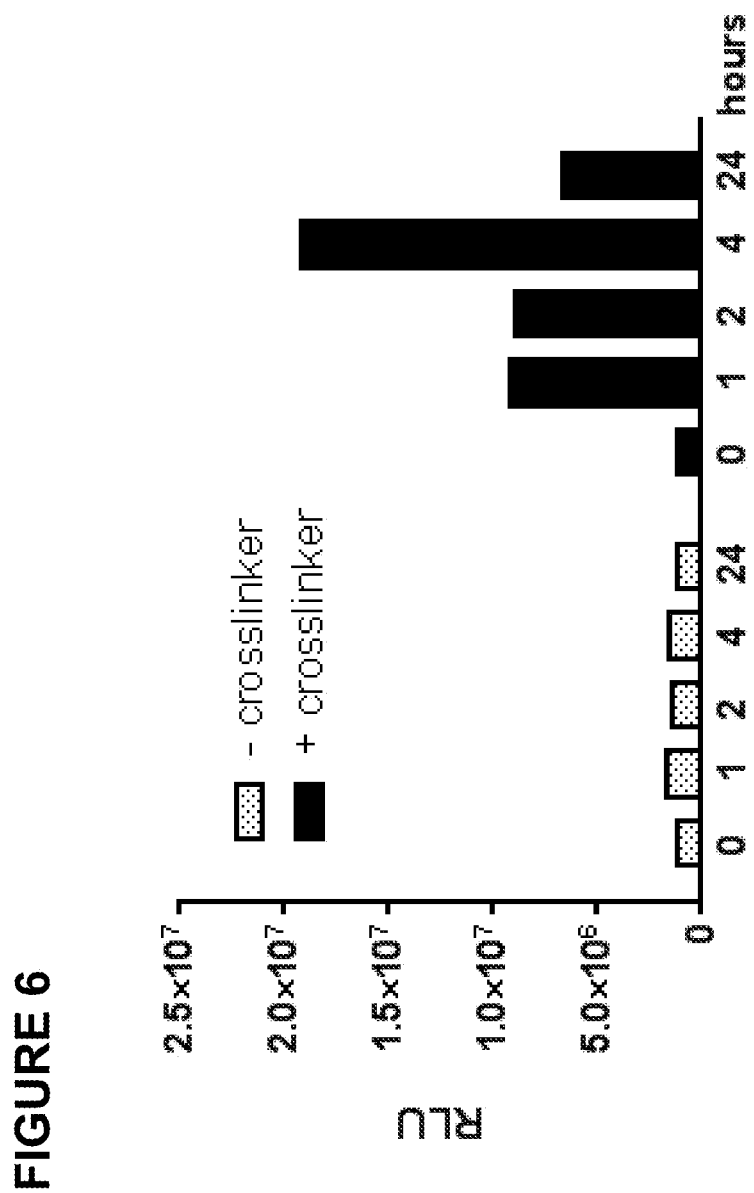

FIG. 6: Anti-DR5 IgG Requires Crosslinker for Caspase Activation. Colo205 cells were incubated with 5 µg/mL anti-DR5 mAb in the absence or presence of crosslinker. Caspase activation was measured after 1, 2, 4, and 24 hours of treatment.

FIG. 7A-FIG. 7D: Multimeric Anti-DR5 mAb is More Cytotoxic than Monomeric IgG.

Figure 7A:
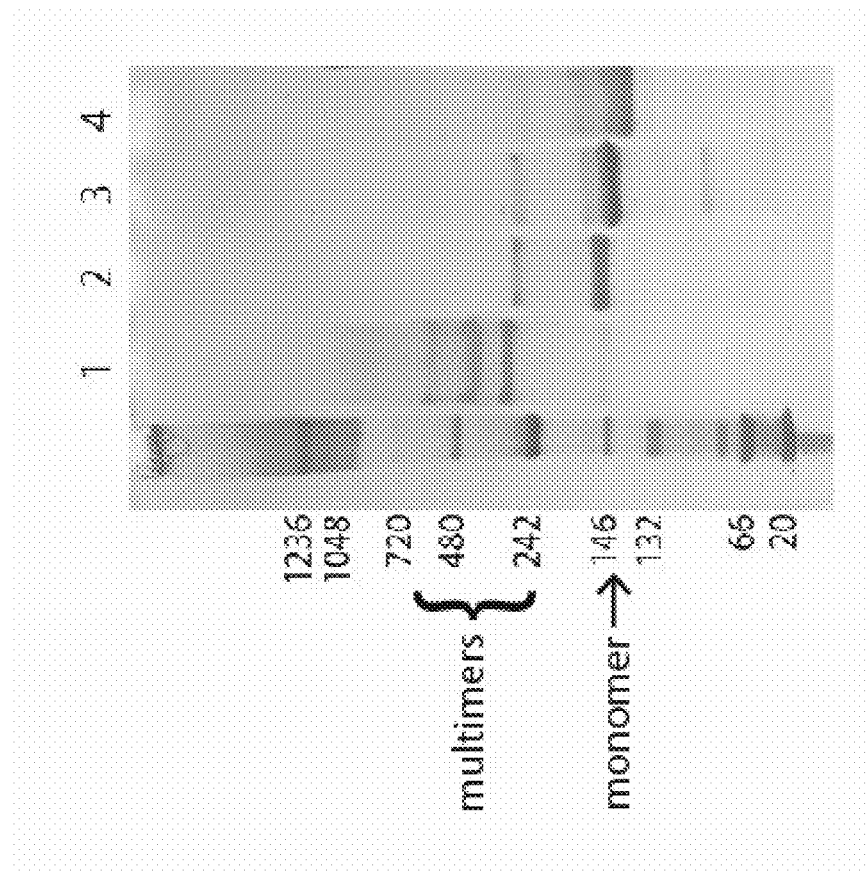

FIG. 7A: Non-reducing SDS-PAGE shows one anti-DR5 mAb that is predominantly multimeric (lane 1); Lane 1 corresponds to R&D Systems clone 71903, Lane 2 corresponds with BioLegend clone DJR2-4, Lane 3 corresponds to Acris Antibodies clone B-K29, and Lane 4 corresponds to Acris Antibodies clone B-D37.

Figure 7B:
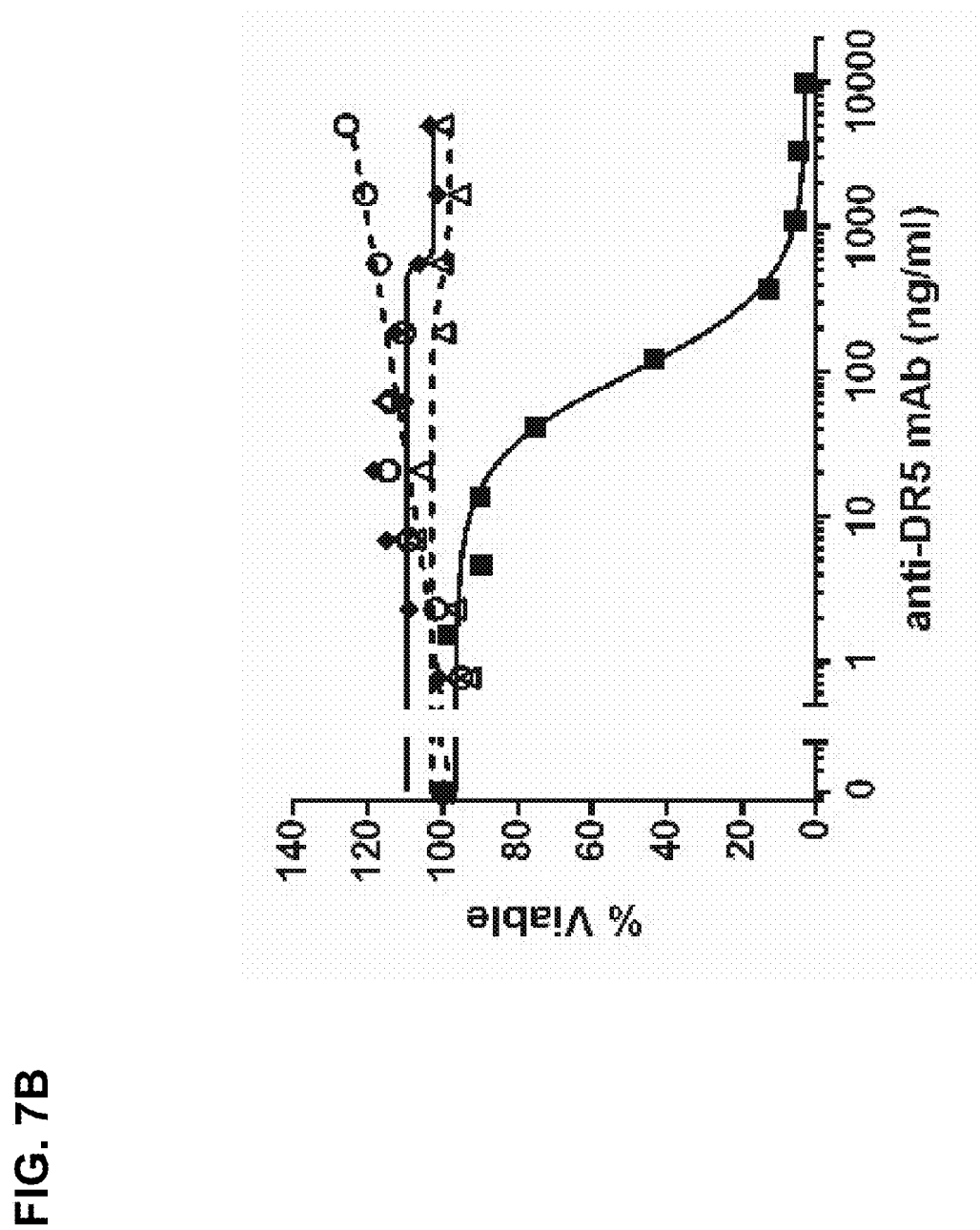

FIG. 7B: Cell viability assay showing that only the multimeric anti-DR5 mAb causes Colo205 cytotoxicity in the absence of crosslinker—R&D Systems clone 71903 (filled squares), BioLegend clone DJR2-4 (open circles, dashed line), Acris Antibodies clone B-K29 (filled diamonds), Acris Antibodies clone B-D37 (open triangles, dashed line).

Figure 7C:
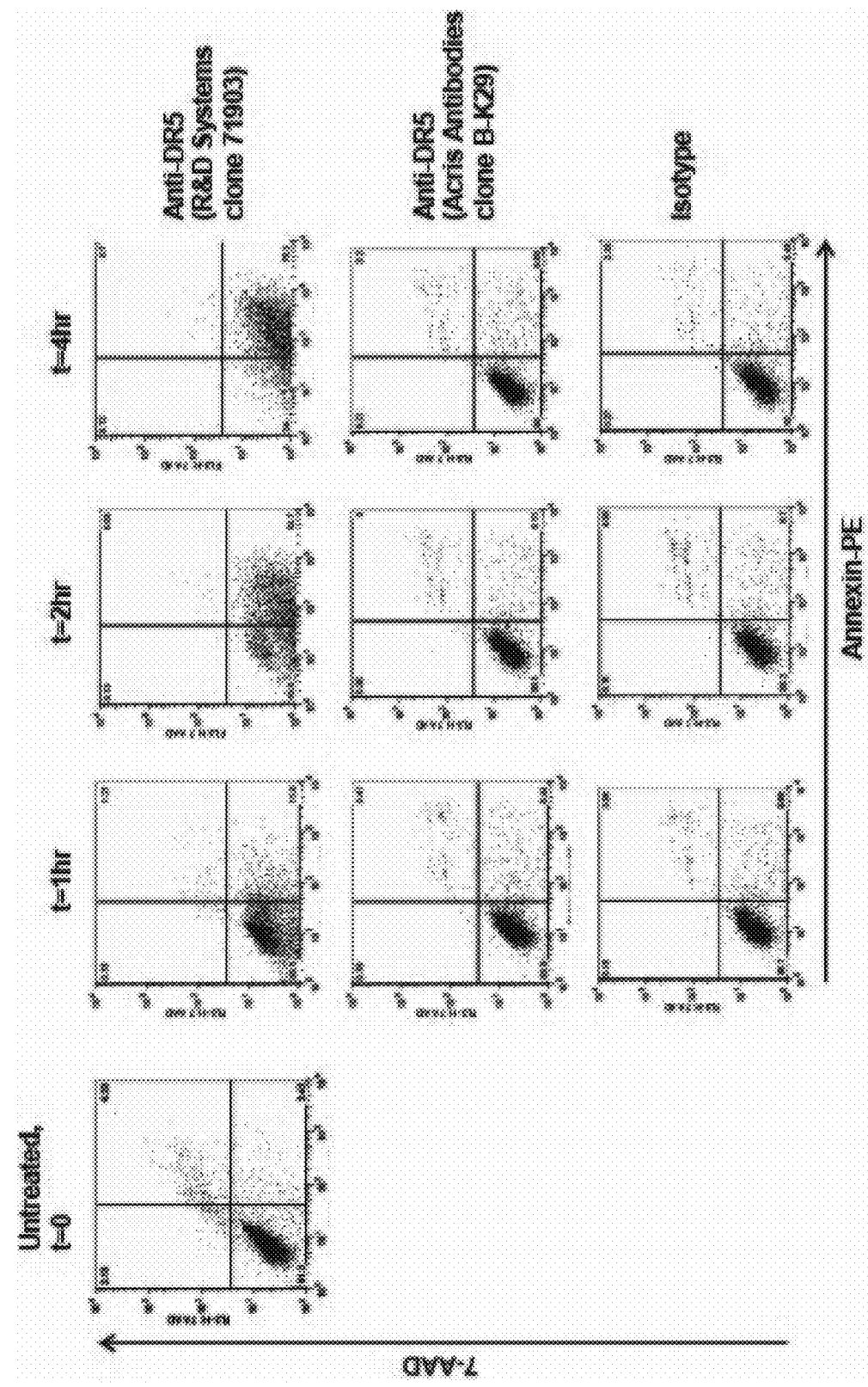

FIG. 7C: FACS assay results showing that in the absence of crosslinker, the multimeric anti-DR5 mAb induces apoptosis in Colo205 cells, but similar results are not observed for the monomeric anti-DR5 mAb or isotype control.

Figure 7D:
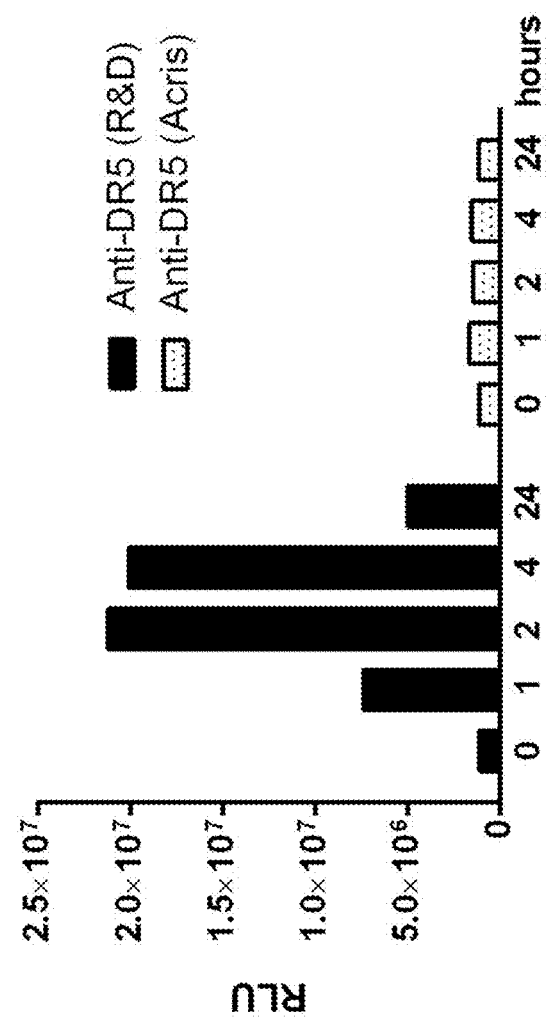

FIG. 7D: Caspase activation luminescence assay showing that in the absence of crosslinker the multimeric, but not monomeric, anti-DR5 mAb induces caspase activation in Colo205 cells.

Figure 8A:
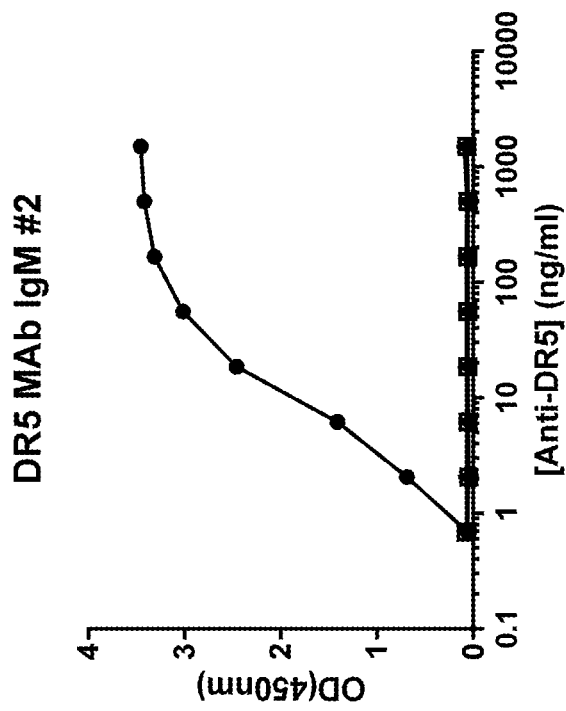
Figure 8B:
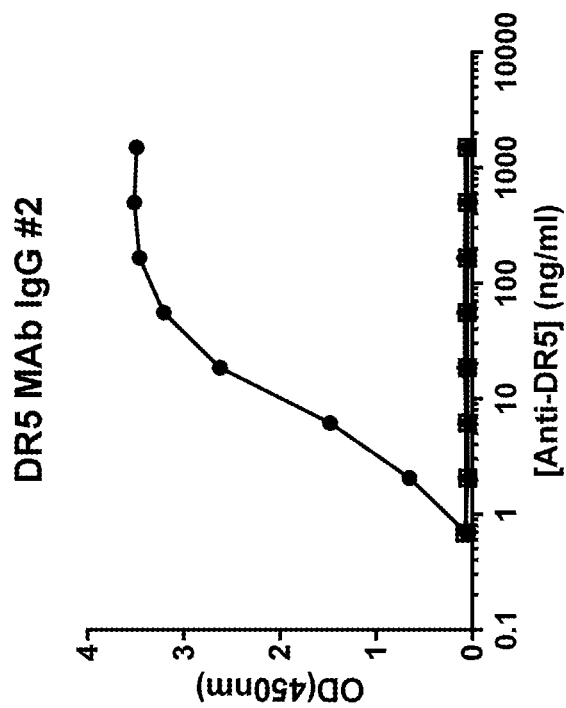

FIG. 8A-FIG. 8B: DR5 MAb IgM is Specific for DR5. DR5 MAb IgG (FIG. 8A) and IgM (FIG. 8B) #2 binds specifically to human DR5, and not DR4 or decoy receptors DcR1 and DcR2 as measured by ELISA. DR5, filled circles; DR4, filled triangles; DcR1, open squares; DcR2, open triangles.

Figure 9:
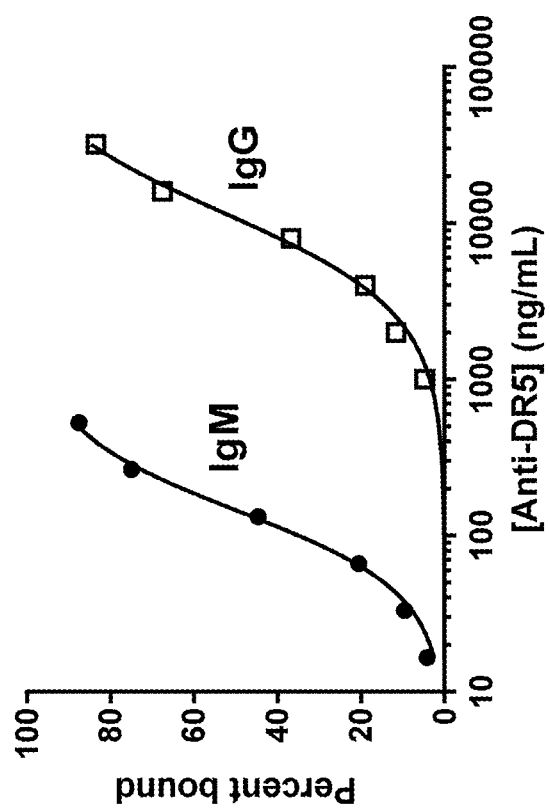

FIG. 9: DR5 MAb IgM Target Cell Binding. DR5 MAb IgM #1 (filled circles) or DR5 MAb IgG #1 (open squares) were incubated with Colo205 cells for 15 minutes, washed, and stained with an Anti-Human IgM or Anti-Human IgG Fc Alexa 647-conjugated secondary antibody. Binding (expressed as % of cells bound) was measured by flow cytometry.

FIG. 10A-FIG. 10E: DR5 MAb IgM Superagonists are More Cytotoxic than Monomeric IgG. Multimeric DR5 MAbs IgM #1 (FIG. 10A), IgM #2 (FIG. 10B), IgM #3 (FIG. 10C), and IgM #4 (FIG. 10D) are more cytotoxic than IgG equivalents on Colo205 cells. Panel E shows that DR5 MAb IgM #1 is more cytotoxic than crosslinked IgG. DR5 MAb IgM, filled circles; DR5 MAb IgG, open squares; DR5 MAb IgG+crosslinker, open triangles.

FIG. 11A-FIG. 11D: DR5 MAb IgM Superagonists are More Cytotoxic on Colo205 Tumor Cells than Primary Human Hepatocytes. Multimeric DR5 MAb IgM #1 (FIG. 11A), DR5 MAb IgM #2 (FIG. 11B), DR5 MAb IgM #3 (FIG. 11C), and DR5 MAb IgM #4 (FIG. 11D) were incubated with Colo205 tumor cells or primary human hepatocytes and cell viability was measured after 24 hours. DR5 MAb IgM treated Colo205 cells, filled circles; DR5 MAb IgM treated hepatocytes, open circles.

DETAILED DESCRIPTION

Definitions

It is to be noted that the term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

As used herein, the term "a non-naturally occurring polypeptide" or any grammatical variants thereof, is a conditional definition that explicitly excludes, but only excludes, those forms of the polypeptide that are, or might be, determined or interpreted by a judge or an administrative or judicial body, to be "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides which retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al., *Protein Eng.* 12(10): 879-884 (1999); and Burks et al., *Proc. Natl. Acad. Sci. USA* 94:412-417 (1997)).

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, which has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, the term "a non-naturally occurring polynucleotide" or any grammatical variants thereof, is a conditional definition that explicitly excludes, but only excludes, those forms of the nucleic acid or polynucleotide that are, or might be, determined or interpreted by a judge, or an administrative or judicial body, to be "naturally-occurring."

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

As used herein, the terms "TNF superfamily of receptor proteins," "TNF superfamily," "TNF receptor family," "TNF receptors" or any combination of such phrases, refer to the family of Tumor Necrosis Factor transmembrane receptor proteins expressed on the surface of various cells and tissues. Family members of this superfamily include those that, upon activation by ligand binding trigger apoptosis, proliferation and/or morphogenesis in the cell in which the receptor protein is expressed. TNF superfamily receptor protein members that trigger apoptosis upon activation include, but are not limited to the following receptors: TNFR1 (DR1), TNFR2, TNFR1/2, CD40 (p50), Fas (CD95, Apo1, DR2), CD30, 4-1BB (CD137, ILA), TRAILR1 (DR4, Apo2), TRAILR2 (DR5), TRAILR3 (DcR1), TRAILR4 (DcR2), OPG (OCIF), TWEAKR (FN14), LIGHTR (HVEM), DcR3, DR3, EDAR, and XEDAR. TNF superfamily receptor protein members which, upon activation, trigger proliferation include, but are not limited to the following receptors: TNFR1/2, GITR (AITR), TACI, BCMA, TWEAKR (FN14), RANK (TRANCER), CD27, CD40 (p50), OX40 (CD134), LT-OR, TNFR1 (DR1) and TNFR2. TNF superfamily receptor protein members which, upon activation, are believed to trigger morphogenesis include, but are not limited to the following receptors: Fas (CD95, Apo1, DR2), TRAILR1 (DR4, Apo2), DR5 (TRAILR2), TRAILR3 (DcR1), TRAILR4 (DcR2), OPG (OCIF), CD40 (p50), EDAR, XEDAR, and TNFR1/2.

Disclosed herein are certain binding molecules, or antigen-binding fragments, variants, or derivatives thereof that bind to certain TNF superfamily receptor proteins, thereby eliciting cellular apoptosis. Unless specifically referring to full-sized antibodies, the term "binding molecule" encompasses full-sized antibodies as well as antigen-binding subunits, fragments, variants, analogs, or derivatives of such antibodies, e.g., engineered antibody molecules or fragments that bind antigen in a manner similar to antibody molecules, but which use a different scaffold.

As used herein, the term "binding molecule" refers in its broadest sense to a molecule that specifically binds to a receptor, e.g., an epitope or an antigenic determinant. As described further herein, a binding molecule can comprise one of more "antigen binding domains" described herein. A non-limiting example of a binding molecule is an antibody or fragment thereof that retains antigen-specific binding.

As used herein, the terms "binding domain" or "antigen binding domain" refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain." Other binding domains include, without limitation, the variable heavy chain (VHH) of an antibody derived from a camelid species, or six immunoglobulin complementarity determining regions (CDRs) expressed in a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable domain of a heavy chain (for camelid species) or at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen-binding fragment of an antibody to a full sized antibody, e.g., an IgG antibody that includes two complete heavy chains and two complete light chains, an IgA antibody that includes four complete heavy chains and four complete light chains and optionally includes a J chain and/or a secretory component, or an IgM antibody that includes ten or twelve complete heavy chains and ten or twelve complete light chains and optionally includes a J chain.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4 or α1-α2)). It is the nature of this chain that determines the "isotype" of the antibody as IgG, IgM, IgA IgG, or IgE, respectively. The immunoglobulin subclasses (subtypes) e.g., $IgG_1$, $IgG_2$, $IgG_3$, $IgA_1$, $IgA_2$, etc. are well characterized and are known to confer functional specialization. Modified versions of each of these immunoglobulins are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are expressed, e.g., by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure, or a "binding unit."

The term "binding unit" is used herein to refer to the portion of a binding molecule, e.g., an antibody or antigen-binding fragment thereof, which corresponds to a standard "H2L2" immunoglobulin structure, i.e., two heavy chains or fragments thereof and two light chains or fragments thereof. In certain aspects, e.g., where the binding molecule is a bivalent IgG antibody or antigen-binding fragment thereof, the terms "binding molecule" and "binding unit" are equivalent. In other aspects, e.g., where the binding molecule is an IgA dimer, an IgM pentamer, or an IgM hexamer, the binding molecule comprises two or more "binding units." Two in the case of an IgA dimer, or five or six in the case of an IgM pentamer or hexamer, respectively. A binding unit need not include full-length antibody heavy and light chains, but will typically be bivalent, i.e., will include two "binding domains," as defined below. Certain binding molecules provided in this disclosure are dimeric, and include two bivalent binding units that include IgA constant regions or fragments thereof. Certain binding molecules provided in this disclosure are pentameric or hexameric, and include five or six bivalent binding units that include IgM constant regions or fragments thereof. A binding molecule comprising two or more, e.g., two, five, or six binding units, is referred to herein as "multimeric."

The terms "valency," "bivalent," "multivalent" and grammatical equivalents, refer to the number of binding domains in given binding molecule or binding unit. As such, the terms "bivalent", "tetravalent", and "hexavalent" in reference to a given binding molecule, e.g., an IgM antibody or fragment thereof, denote the presence of two binding domains, four binding domains, and six binding domains, respectively. In a typical IgM-derived binding molecule where each binding unit is bivalent, the binding molecule itself can have 10 or 12 valencies. A bivalent or multivalent binding molecule can be monospecific, i.e., all of the binding domains are the same, or can be bispecific or multispecific, e.g., where two or more binding domains are different, e.g., bind to different epitopes on the same antigen, or bind to entirely different antigens.

The term "epitope" includes any molecular determinant capable of specific binding to an antibody. In certain aspects, an epitope can include chemically active surface groupings of molecules such as amino acids, sugar side chains, phosphoryl, or sulfonyl, and, in certain aspects, can have a three dimensional structural characteristics, and or specific charge characteristics. An epitope is a region of a target that is bound by an antibody.

The term "target" is used in the broadest sense to include substances that can be bound by a binding molecule. A target can be, e.g., a polypeptide, a nucleic acid, a carbohydrate, a lipid, or other molecule. Moreover, a "target" can, for example, be a cell, an organ, or an organism that comprises an epitope bound that can be bound by a binding molecule.

Both the light and heavy chains are divided into regions of structural and functional homology. The terms "constant" and "variable" are used functionally. In this regard, it will be appreciated that the variable domains of both the variable light (VL) and variable heavy (VH) chain portions determine antigen recognition and specificity. Conversely, the constant domains of the light chain (CL) and the heavy chain (e.g., CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains actually comprise the carboxy-terminus of the heavy and light chain, respectively.

A "full length IgM antibody heavy chain" is a polypeptide that includes, in N-terminal to C-terminal direction, an antibody heavy chain variable domain (VH), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4) that can include a tailpiece.

A "full length IgA antibody heavy chain" is a polypeptide that includes, in N-terminal to C-terminal direction, an antibody heavy chain variable domain (VH), an antibody constant heavy chain constant domain 1 (CA1 or Cα1), an antibody heavy chain constant domain 2 (CA2 or Cα2), and an antibody heavy chain constant domain 3 (CA3 or Cα3) that can include a tailpiece.

As indicated above, variable region(s) allows a binding molecule to selectively recognize and specifically bind epitopes on antigens. That is, the VL domain and VH domain, or subset of the complementarity determining regions (CDRs), of a binding molecule, e.g., an antibody, combine to form the antigen binding domain. More specifically, an antigen binding domain can be defined by three CDRs on each of the VH and VL chains. Certain antibodies form larger structures. For example, IgA can form a molecule that includes two H2L2 binding units and a J chain covalently connected via disulfide bonds, which can be further associated with a secretory component, and IgM can form a pentameric or hexameric molecule that includes five or six H2L2 binding units and optionally a J chain covalently connected via disulfide bonds.

The six "complementarity determining regions" or "CDRs" present in an antibody antigen-binding domain are short, non-contiguous sequences of amino acids that are specifically positioned to form the binding domain as the antibody assumes its three dimensional configuration in an aqueous environment. The remainder of the amino acids in the binding domain, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.,* 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids which encompass the CDRs as defined by each of the above cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

CDR Definitions*

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

*Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5\times10^{-2}$ sec$^{-1}$, $10^{-2}$ sec$^{-1}$, $5\times10^{-3}$ sec$^{-1}$, $10^{-3}$ sec$^{-1}$, $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

A binding molecule, e.g., an antibody or antigen-binding fragment, variant, or derivative disclosed herein can be said to bind a target antigen with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$, $5'10^4$ M$^{-1}$ sec$^{-1}$, $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of binding domains and an antigen. See, e.g., Harlow at pages 29-34. Avidity is related to both the affinity of individual binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a bivalent monoclonal antibody with a receptor present at a high density on a cell surface would also be of high avidity.

Binding molecules or antigen-binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or K$_D$ no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Antibody fragments including single-chain antibodies or other binding domains can exist alone or in combination with one or more of the following: hinge region, CH1, CH2, CH3, or CH4 domains, J chain, or secretory component. Also included are antigen-binding fragments that can include any combination of variable region(s) with one or more of a hinge region, CH1, CH2, CH3, or CH4 domains, a J chain, or a secretory component. Binding molecules, e.g., antibodies, or antigen-binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al.

As used herein, the term "heavy chain subunit" includes amino acid sequences derived from an immunoglobulin heavy chain, a binding molecule, e.g., an antibody comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody or fragment, variant, or derivative thereof can include without limitation, in addition to a VH domain: a CH1 domain; a CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody or fragment, variant, or derivative thereof can include, in addition to a VH domain, a CH3 domain and a CH4 domain; or a CH3 domain, a CH4 domain, and a J chain. Further, a binding molecule for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule.

As used herein, the term "light chain subunit" includes amino acid sequences derived from an immunoglobulin light chain. The light chain subunit includes at least a VL, and can further include a CL (e.g., Cκ or Cλ) domain.

Binding molecules, e.g., antibodies or antigen-binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of a typical IgG heavy chain molecule.

As used herein the term "CH2 domain" includes the portion of a heavy chain molecule that extends, e.g., from about amino acid 244 to amino acid 360 of an IgG antibody using conventional numbering schemes (amino acids 244 to 360, Kabat numbering system; and amino acids 231-340, EU numbering system; see Kabat E A et al., op. cit. The CH3 domain extends from the CH2 domain to the C-terminal of the IgG molecule and comprises approximately 108 amino acids. Certain immunoglobulin classes, e.g., IgM, further include a CH4 region.

As used herein, the term "hinge region" includes the portion of a heavy chain molecule that joins the CH1 domain to the CH2 domain in IgG, IgA, and IgD heavy chains. This hinge region comprises approximately 25 amino acids and is flexible, thus allowing the two N-terminal antigen binding regions to move independently.

As used herein the term "disulfide bond" includes the covalent bond formed between two sulfur atoms. The amino acid cysteine comprises a thiol group that can form a disulfide bond or bridge with a second thiol group.

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The terms "multispecific antibody" or "bispecific antibody" refer to an antibody that has binding domains for two or more different epitopes within a single antibody molecule. Other binding molecules in addition to the canonical antibody structure can be constructed with two binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Ströhlein and Heiss, *Future Oncol.* 6:1387-94 (2010); Mabry and Snavely, *IDrugs.* 13:543-9 (2010)). A bispecific antibody can also be a diabody.

As used herein, the term "engineered antibody" refers to an antibody in which the variable domain in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

As used herein, the term "cross-linked" refers to joining together of two or more molecules by a third molecule. For example, a bivalent antibody with two binding domains that specifically bind to the same antigen can "cross-link" two copies of that antigen, e.g., as they are expressed on a cell. Many TNF superfamily receptor proteins require cross-linking of three or more receptors on the surface of a cell for activation. Cross-linking of TNF superfamily receptor proteins means, for instance, contacting a binding molecule, as disclosed herein, with TNF superfamily receptors expressed on the surface of a cell such that at least three such family members are simultaneously bound together by one or more binding molecules, thereby activating the receptors.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide. A portion of a polypeptide that is "amino-terminal" or "N-terminal" to another portion of a polypeptide is that portion that comes earlier in the sequential polypeptide chain. Similarly a portion of a polypeptide that is "carboxy-terminal" or "C-terminal" to another portion of a polypeptide is that portion that comes later in the sequential polypeptide chain. For example in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into RNA, e.g., messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" includes subjects, such as mammalian subjects, that would benefit from administration of a binding molecule such as an antibody, comprising one or more antigen binding domains. Such binding molecules, e.g., antibodies, can be used, e.g., for a diagnostic procedures and/or for treatment or prevention of a disease.

IgM Binding Molecules

IgM is the first immunoglobulin produced by B cells in response to stimulation by antigen, and is present at around 1.5 mg/ml in serum with a half-life of 5 days. IgM is a pentameric or hexameric molecule. An IgM binding unit includes two light and two heavy chains. While IgG contains three heavy chain constant domains (CH1, CH2 and CH3), the heavy (μ) chain of IgM additionally contains a fourth constant domain (CH4), that includes a C-terminal "tailpiece." The human IgM constant region typically comprises the amino acid sequence SEQ ID NO: 74. The human Cμ1 region ranges from about amino acid 5 to about amino acid 102 of SEQ ID NO: 74; the human Cμ2 region ranges from about amino acid 114 to about amino acid 205 of SEQ ID NO: 74, the human CO region ranges from about amino acid 224 to about amino acid 319 of SEQ ID NO: 74, the Cμ4 region ranges from about amino acid 329 to about amino acid 430 of SEQ ID NO: 74, and the tailpiece ranges from about amino acid 431 to about amino acid 453 of SEQ ID NO: 74. SEQ ID NO: 74 is presented below:

```
GSASAPTLFPLVSCENSPSDTSSVAVGCLAQDFLPDSITLSW

KYKNNSDISSTRGFPSVLRGGKYAATSQVLLPSKDVMQGT

DEHVVCKVQHPNGNKEKNVPLPVIAELPPKVSVFVPPRDGF

FGNPRKSKLICQATGFSPRQIQVSWLREGKQVGSGVTTDQV

QAEAKESGPTTYKVTSTLTIKESDWLGQSMFTCRVDHRGLT

FQQNASSMCVPDQDTAIRVFAIPPSFASIFLTKSTKLTCLVTD
```

```
LTTYDSVTISWTRQNGEAVKTHTNISESHPNATFSAVGEASI

CEDDWNSGERFTCTVTHTDLPSPLKQTISRPKGVALHRPDV

YLLPPAREQLNLRESATITCLVTGFSPADVFVQWMQRGQPL

SPEKYVTSAPMPEPQAPGRYFAHSILTVSEEEWNTGETYTC

VAHEALPNRVTERTVDKSTGKPTLYNVSLVMSDTAGTCY
```

Five IgM binding units can form a complex with an additional small polypeptide chain (the J chain) to form an IgM antibody. The human J chain comprises the amino acid sequence SEQ ID NO: 76. Without the J chain, IgM binding units typically assemble into a hexamer. While not wishing to be bound by theory, the assembly of IgM binding units into a pentameric or hexameric binding molecule is thought to involve the CO and CO domains. Accordingly, a pentameric or hexameric binding molecule provided in this disclosure typically includes IgM constant regions that include at least the CO and CO domains. SEQ ID NO: 76 is presented below:

```
MKNHLLFWGVLAVFIKAVHVKAQEDERIVLVDNKCKCARI

TSRIIRSSEDPNEDIVERNIRIIVPLNNRENISDPTSPLRTRFVY

HLSDLCKKCDPTEVELDNQIVTATQSNICDEDSATETCYTY

DRNKCYTAVVPLVYGGETKMVETALTPDACYPD
```

An IgM heavy chain constant region can additionally include a Cμ2 domain or a fragment thereof, a Cμ1 domain or a fragment thereof, and/or other IgM heavy chain domains. In certain aspects, a binding molecule as provided herein can include a complete IgM heavy (μ) chain constant domain, e.g., SEQ ID NO: 74, or a variant, derivative, or analog thereof.

Pentameric or Hexameric TNF Superfamily Binding Molecules

This disclosure provides a pentameric or hexameric binding molecule, i.e., a binding molecule with five or six "binding units" as defined herein, that can specifically bind to one or more TNF superfamily receptor proteins, e.g., DR5. A binding molecule as provided herein can possess improved binding characteristics or biological activity as compared to a binding molecule composed of a single binding unit, e.g., a bivalent IgG antibody. For example, a pentameric or hexameric binding molecule can more efficiently cross-link three or more TNF superfamily receptor molecules on the surface of a cell, e.g., a tumor cell, thereby facilitating apoptosis of the cell.

A binding molecule as provided herein can likewise possess distinctive characteristics compared to multivalent binding molecule composed of synthetic or chimeric structures. For example, use of human IgM constant regions can afford reduced immunogenicity and thus increased safety relative to a binding molecule containing chimeric constant regions or synthetic structures. Moreover, an IgM-based binding molecule can consistently form hexameric or pentameric oligomers resulting in a more homogeneous expression product. Superior complement fixation can also be an advantageous effector function of IgM-based binding molecules.

In certain aspects, the disclosure provides a pentameric or hexameric binding molecule comprising five or six bivalent binding units, respectively, where each binding unit includes two IgM heavy chain constant regions or fragments thereof.

In certain aspects, the two IgM heavy chain constant regions are human heavy chain constant regions.

Where the binding molecule provided herein is pentameric, the binding molecule can further comprise a J chain, or fragment thereof, or variant thereof.

An IgM heavy chain constant region can include one or more of a Cμ1 domain, a Cμ2 domain, a Cμ3 domain, and/or a Cμ4 domain, provided that the constant region can serve a desired function in the binding molecule, e.g., associate with second IgM constant region to form a binding domain, or associate with other binding units to form a hexamer or a pentamer. In certain aspects the two IgM heavy chain constant regions or fragments thereof within an individual binding unit each comprise a Cμ3 domain or fragment thereof, a Cμ4 domain or fragment thereof, a tailpiece (TP) or fragment thereof, or any combination of a Cμ3 domain a Cμ domain, and a TP or fragment thereof. In certain aspects the two IgM heavy chain constant regions or fragments thereof within an individual binding unit each further comprise a Cμ2 domain or fragment thereof, a Cμ1 domain or fragment thereof, or a Cμ1 domain or fragment thereof and a Cμ2 domain or fragment thereof.

In certain aspects each of the two IgM heavy chain constant regions in a given binding unit is associated with an antigen-binding domain, for example an Fv portion of an antibody, e.g., a VH and a VL of a human or murine antibody, where the VL can be associated with a light chain constant region. In a binding molecule as provided herein at least one antigen-binding domain of the binding molecule is a TNF superfamily receptor protein binding domain, i.e., a binding domain that can specifically bind to a member of the TNF superfamily of receptor proteins, e.g., human DR5.

IgA Binding Molecules

IgA plays a critical role in mucosal immunity, and comprises about 15% of total immunoglobulin produced. IgA is a monomeric or dimeric molecule. An IgA binding unit includes two light and two heavy chains. IgA contains three heavy chain constant domains (Cα1, Cα2 and Cα3), and includes a C-terminal "tailpiece." Human IgA has two subtypes, IgA1 and IgA2. The human IgA1 constant region typically comprises the amino acid sequence SEQ ID NO: 78. The human Cα1 region ranges from about amino acid 6 to about amino acid 98 of SEQ ID NO: 78; the human Cα2 region ranges from about amino acid 125 to about amino acid 220 of SEQ ID NO: 78, the human Cα3 region ranges from about amino acid 228 to about amino acid 330 of SEQ ID NO: 78, and the tailpiece ranges from about amino acid 331 to about amino acid 352 of SEQ ID NO: 78. The human IgA2 constant region typically comprises the amino acid sequence SEQ ID NO: 79. The human Cα1 region ranges from about amino acid 6 to about amino acid 98 of SEQ ID NO: 79; the human Cα2 region ranges from about amino acid 112 to about amino acid 207 of SEQ ID NO: 79, the human Cα3 region ranges from about amino acid 215 to about amino acid 317 of SEQ ID NO: 79, and the tailpiece ranges from about amino acid 318 to about amino acid 340 of SEQ ID NO: 79. SEQ ID NOS: 78 and 79 are presented below:

```
                                        SEQ ID NO: 78
ASPTSPKVFPLSLCSTQPDGNVVIACLVQGFFPQEPLSVTWS

ESGQGVTARNFPPSQDASGDLYTTSSQLTLPATQCLAGKSV

TCHVKHYTNPSQDVTVPCPVPSTPPTPSPSTPPTPSPSCCHPR
```

```
-continued
LSLHRPALEDLLLGSEANLTCTLTGLRDASGVTFTWTPSSG

KSAVQGPPERDLCGCYSVSSVLPGCAEPWNHGKTFTCTAA

YPESKTPLTATLSKSGNTFRPEVHLLPPPSEELALNELVTLTC

LARGFSPKDVLVRWLQGSQELPREKYLTWASRQEPSQGTT

TFAVTSILRVAAEDWKKGDTFSCMVGHEALPLAFTQKTIDR

LAGKPTHVNVSVVMAEVDGTCY

SEQ ID NO: 79
ASPTSPKVFPLSLDSTPQDGNVVVACLVQGFFPQEPLSVTW

SESGQNVTARNFPPSQDASGDLYTTSSQLTLPATQCPDGKS

VTCHVKHYTNPSQDVTVPCPVPPPPPCCHPRLSLHRPALED

LLLGSEANLTCTLTGLRDASGATFTWTPSSGKSAVQGPPER

DLCGCYSVSSVLPGCAQPWNHGETFTCTAAHPELKTPLTAN

ITKSGNTFRPEVHLLPPPSEELALNELVTLTCLARGFSPKDVL

VRWLQGSQELPREKYLTWASRQEPSQGTTTFAVTSILRVAA

EDWKKGDTFSCMVGHEALPLAFTQKTIDRMAGKPTHVNVS

VVMAEVDGTCY
```

Two IgA binding units can form a complex with two additional polypeptide chains, the
J chain (SEQ ID NO: 76) and the secretory component (precursor, SEQ ID NO: 80, mature, SEQ ID NO: 81) to form a secretory IgA (sIgA) antibody. While not wishing to be bound by theory, the assembly of IgA binding units into a dimeric sIgA binding molecule is thought to involve the Cα3 and tailpiece domains. Accordingly, a dimeric sIgA binding molecule provided in this disclosure typically includes IgA constant regions that include at least the Cα3 and tailpiece domains. SEQ ID NO: 80 and SEQ ID NO: 81 are presented below:

```
SEQ ID NO: 80:
MLLFVLTCLLAVFPAISTKSPIFGPEEVNSVEGNSVSITCYYP

PTSVNRHTRKYWCRQGARGGCITLISSEGYVSSKYAGRANL

TNFPENGTFVVNIAQLSQDDSGRYKCGLGINSRGLSFDVSLE

VSQGPGLLNDTKVYTVDLGRTVTINCPFKTENAQKRKSLYK

QIGLYPVLVIDSSGYVNPNYTGRIRLDIQGTGQLLFSVVINQL

RLSDAGQYLCQAGDDSNSNKKNADLQVLKPEPELVYEDLR

GSVTFHCALGPEVANVAKFLCRQSSGENCDVVVNTLGKRA

PAFEGRILLNPQDKDGSFSVVITGLRKEDAGRYLCGAHSDG

QLQEGSPIQAWQLFVNEESTIPRSPTVVKGVAGGSVAVLCP

YNRKESKSIKYWCLWEGAQNGRCPLLVDSEGWVKAQYEG

RLSLLEEPGNGTFTVILNQLTSRDAGFYWCLTNGDTLWRTT

VEIKIIEGEPNLKVPGNVTAVLGETLKVPCHFPCKFSSYEKY

WCKWNNTGCQALPSQDEGPSKAFVNCDENSRLVSLTLNLV

TRADEGWYWCGVKQGHFYGETAAVYVAVEERKAAGSRD

VSLAKADAAPDEKVLDSGFREIENKAIQDPRLFAEEKAVAD

TRDQADGSRASVDSGSSEEQGGSSRALVSTLVPLGLVLAVG
```

```
-continued
AVAVGVARARHRKNVDRVSIRSYRTDISMSDFENSREFGA

NDNMGASSITQETSLGGKEEFVATTESTTETKEPKKAKRSS

KEEAEMAYKDFLLQSSTVAAEAQDGPQEA

SEQ ID NO: 81:
KSPIFGPEEVNSVEGNSVSITCYYPPTSVNRHTRKYWCRQG

ARGGCITLISSEGYVSSKYAGRANLTNFPENGTFVVNIAQLS

QDDSGRYKCGLGINSRGLSFDVSLEVSQGPGLLNDTKVYTV

DLGRTVTINCPFKTENAQKRKSLYKQIGLYPVLVIDSSGYVN

PNYTGRIRLDIQGTGQLLFSVVINQLRLSDAGQYLCQAGDD

SNSNKKNADLQVLKPEPELVYEDLRGSVTFHCALGPEVAN

VAKFLCRQSSGENCDVVVNTLGKRAPAFEGRILLNPQDKD

GSFSVVITGLRKEDAGRYLCGAHSDGQLQEGSPIQAWQLFV

NEESTIPRSPTVVKGVAGGSVAVLCPYNRKESKSIKYWCLW

EGAQNGRCPLLVDSEGWVKAQYEGRLSLLEEPGNGTFTVIL

NQLTSRDAGFYWCLTNGDTLWRTTVEIKIIEGEPNLKVPGN

VTAVLGETLKVPCHFPCKFSSYEKYWCKWNNTGCQALPSQ

DEGPSKAFVNCDENSRLVSLTLNLVTRADEGWYWCGVKQ

GHFYGETAAVYVAVEERKAAGSRDVSLAKADAAPDEKVL

DSGFREIENKAIQDPR
```

An IgA heavy chain constant region can additionally include a Cα2 domain or a fragment thereof, a Cα1 domain or a fragment thereof, and/or other IgA heavy chain domains. In certain aspects, a binding molecule as provided herein can include a complete IgA heavy (α) chain constant domain (e.g., SEQ ID NO: 78 or SEQ ID NO: 79), or a variant, derivative, or analog thereof.

Dimeric TNF Superfamily Receptor Binding Molecules

This disclosure provides a dimeric binding molecule, e.g., a binding molecule with two IgA "binding units" as defined herein, that can specifically bind to one or more TNF superfamily receptor proteins, e.g., DR5. A binding molecule as provided herein can possess improved binding characteristics or biological activity as compared to a binding molecule composed of a single binding unit, e.g., a bivalent IgG antibody. For example, an IgA binding molecule can more efficiently cross-link three or more TNF superfamily receptors on the surface of a cell, e.g., a tumor cell, thereby facilitating apoptosis of the cell. Moreover, an IgA binding molecule can reach mucosal sites providing greater tissue distribution for the binding molecules provided herein. Use of an IgA-based binding molecule can allow, for example, greater tissue distribution for a binding molecule provided herein. Mucosal distribution could be beneficial for certain cancers, e.g., lung cancer, ovarian cancer, colorectal cancer, or squamous cell carcinoma. Likewise, a dimeric binding molecule as provided herein can possess binding characteristics or biological activity that can be distinguished from a binding molecule comprising five or six binding units, e.g., a hexameric or pentameric IgM antibody. For example, a dimeric binding molecule would be smaller, and could, for example, achieve better tissue penetration in solid tumors.

In certain aspects, the disclosure provides a dimeric binding molecule comprising two bivalent binding units, where each binding unit includes two IgA heavy chain constant regions or fragments thereof. In certain aspects, the two IgA heavy chain constant regions are human heavy chain constant regions.

A dimeric IgA binding molecule as provided herein can further comprise a J chain, or fragment thereof, or variant thereof. A dimeric IgA binding molecule as provided herein can further comprise a secretory component, or fragment thereof, or variant thereof.

An IgA heavy chain constant region can include one or more of a Cα1 domain, a α2 domain, and/or a Cα3 domain, provided that the constant region can serve a desired function in the binding molecule, e.g., associate with a light chain constant region to facilitate formation of an antigen binding domain, or associate with another IgA binding unit to form a dimeric binding molecule. In certain aspects the two IgA heavy chain constant regions or fragments thereof within an individual binding unit each comprise a Cα3 domain or fragment thereof, a tailpiece (TP) or fragment thereof, or any combination of a Cα3 domain, a TP, or fragment thereof. In certain aspects the two IgA heavy chain constant regions or fragments thereof within an individual binding unit each further comprise a Cα2 domain or fragment thereof, a Cα1 domain or fragment thereof, or a Cα1 domain or fragment thereof and a Cα2 domain or fragment thereof.

In certain aspects each of the two IgA heavy chain constant regions in a given binding unit is associated with an antigen binding domain, for example an Fv portion of an antibody, e.g., a VH and a VL of a human or murine antibody, where the VL can be associated with a light chain constant region. In a binding molecule as provided herein at least one antigen-binding domain of the binding molecule is a TNF superfamily receptor protein binding domain, i.e., a binding domain that can specifically bind to a member of the TNF superfamily of receptor proteins, e.g., human DR5.

TNF Superfamily Receptor Binding Domains

A TNF superfamily receptor protein binding molecule as provided herein can be dimeric, pentameric, or hexameric, comprising two, five, or six bivalent binding units, respectively. The binding units can be full length or variants or fragments thereof that retain binding function.

Each binding unit comprises two IgA or IgM heavy chain constant regions or fragments thereof, each associated with an antigen-binding domain. As noted above, an antigen binding domain is a region of a binding molecule that is necessary and sufficient to specifically bind to an epitope. A "binding molecule" as described herein can include one, two, three, four, five, six, seven, eight, nine, ten, eleven, twelve or more "antigen binding domains."

A dimeric, pentameric, or hexameric binding molecule as provided herein can include at least three antigen-binding domains which specifically and agonistically bind to a tumor necrosis factor (TNF) superfamily receptor protein. As noted above, some of these TNF superfamily receptor proteins, upon activation, can induce apoptosis of the cell expressing the TNF superfamily receptor protein which was bound. Apoptosis will occur, as presently understood, when multiple receptor proteins are bound together, causing cross-linking of the receptor molecules such that a signal is transmitted across the cell membrane into the cytosol of the cell expressing the TNF superfamily receptor protein.

A dimeric, pentameric, or hexameric binding molecule as provided herein can cross-link at least three identical TNF superfamily receptor proteins expressed on the surface of a cell. Due to the dimeric, pentameric, or hexameric nature of a TNF superfamily receptor protein binding molecule as provided herein can cross-link as many as three, four, five, six, seven, eight, nine, ten, eleven, or twelve TNF superfamily receptor proteins, the receptor proteins are necessarily spatially brought into proximity of each other, thereby contributing to their cross-linking and activation. When all five or all six of the bivalent binding units a TNF superfamily receptor protein binding molecule as provided herein binds to up to ten or twelve TNF superfamily receptor proteins on a single cell, respectively, cross-linking and activation of the receptors can occur.

Because each of the binding units is bivalent, each binding molecule can bind to as many as 10 (for pentameric binding molecules) or 12 (for hexameric binding molecules) TNF superfamily receptor proteins.

Upon activation of the receptors by the binding of a dimeric, pentameric, or hexameric binding molecule as provided herein, the cell can either undergo apoptosis, activation or morphogenesis, as described above, depending on which receptor of the superfamily is bound.

In certain aspects, a dimeric, pentameric, or hexameric binding molecule as presently disclosed can induce TNF superfamily receptor-mediated apoptosis in a TNF receptor superfamily-expressing cell at a higher potency than an equivalent amount of a bivalent IgG antibody or fragment thereof, which also specifically binds to and agonizes the same TNF superfamily receptor protein. Not wishing to be bound by theory, because a provided binding molecule is dimeric, pentameric, or hexameric, and because each binding unit is bivalent, such a binding molecule can induce receptor-mediated functions previously characterized for this superfamily of receptor proteins at a higher potency than any single binding unit alone, such as an equivalent IgG binding unit. IgG binding units are bivalent, containing two binding sites, but as previous clinical studies have shown, binding of two receptors of this superfamily with a single IgG molecule can be ineffective without addition of other components, such as cross-linkers, etc.

By "potency" or "improved binding characteristics" is meant the least amount of a given binding molecule necessary to achieve a given biological result, e.g., activation of 20%, 50%, or 90% of a TNF superfamily receptor protein in a given assay, e.g., a ELISA or Western blot based caspase assays, annexin-v staining as seen by FACS analysis, or other assay as provided in the examples below. For instance, when the TNF superfamily receptor protein is one which, when activated, causes apoptosis of the cell in which it is activated, potency can be expressed as a curve in which % survival of cells is on the Y axis, and binding molecule concentration (in, e.g., μg/ml or μM) is on the X axis.

Because a binding molecule as provided herein is dimeric, pentameric, or hexameric, it can contain as many as 4, 10, or 12, respectively, antigen-binding domains. Each of the antigen-binding domains can specifically bind to and agonize the TNF superfamily receptor. Further, each antigen-binding domain can be specific for one particular epitope of the TNF superfamily receptor protein. In certain aspects, the binding molecule does not cross-react with other TNF superfamily receptor proteins. However, in other aspects, two or more of the antigen-binding domains can be specific for different epitopes and/or different TNF superfamily receptor proteins.

Thus, a single dimeric, pentameric, or hexameric binding molecule can: a) simultaneously bind a single epitope on many identical receptor proteins, b) bind many different epitopes on the same identical receptor protein, or c) can bind different epitopes on different TNF superfamily receptor proteins. In embodiment a), a TNF superfamily receptor protein binding molecule as provided herein can bind multiple copies of an identical TNF superfamily receptor at the same location for each identical copy, thereby forming a raft of such receptor proteins in a single location and likely increasing the likelihood that the receptor proteins will be activated. In other embodiments, such as embodiment c), a dimeric, pentameric, or hexameric binding molecule as provided herein can be used to contact multiple different TNF superfamily receptor proteins, thereby activating more than one pathway through the various targeted receptors, to achieve the desired biological response in the cells. Of course, in these embodiments, a TNF superfamily receptor protein binding molecule as provided herein can contact and agonize such receptors all on one single cell, or across multiple cells.

Thus, a dimeric, pentameric, or hexameric binding molecule as provided herein can comprise three, four, five, six, seven, eight, nine, ten, or in the case of the hexameric binding molecules, as many as eleven, or twelve antigen-binding domains that specifically and agonistically bind to one or more TNF superfamily receptor proteins expressed on the surface of one or more cells, thereby inducing the intended or desired biological response in the cell(s).

The binding units of a dimeric, pentameric, or hexameric binding molecule as provided herein can be human, humanized, or chimeric immunoglobulin binding units. Methods of humanizing immunoglobulin sequences are well known in the art. Thus, the nucleotide sequences encoding a dimeric, pentameric, or hexameric binding molecule polypeptide can be directly from human sequences, or can be humanized or chimeric, i.e., encoded by sequences from multiple different species.

A dimeric, pentameric, or hexameric binding molecule as provided herein can specifically bind any one of the known TNF superfamily receptor proteins. These receptor proteins can be grouped into specific functions of triggering either morphogenesis, apoptosis or proliferation. Thus, a TNF superfamily receptor protein binding molecule as provided herein can, for instance, specifically bind to any one or more of the following receptors: TNFR1 (DR1), TNFR2, TNFR1/2, CD40 (p50), Fas (CD95, Apo1, DR2), CD30, 4-1BB (CD137, ILA), DR4 (TRAILR1, Apo2), DR5 (TRAILR2), DcR1 (TRAILR3), DcR2 (TRAILR4), OPG (OCIF), TWEAKR (FN14), LIGHTR (HVEM), DcR3, DR3, EDAR, and XEDAR.

In one embodiment, a TNF superfamily receptor protein binding molecule as provided herein specifically and agonistically binds to DR5 but does not specifically bind to other receptors, e.g., DR4 (TRAILR1, Apo2), decoy receptor DcR1 (TRAILR3) or decoy receptor DcR2 (TRAILR4). In certain aspects the TNF superfamily receptor protein binding molecule as provided herein can specifically and agonistically bind to DR5 and can also specifically bind to DR4.

The cells which express TNF superfamily receptor proteins can be any animal cell. For instance, in one embodiment, the cell is a human cell. For example, the cell can be any one or more of primate, rodent, canine, equine, etc., cells. Further, the cell expressing the TNF superfamily receptor protein can be a cancer cell. That is, the cell can be a cell in a tumor which is malignant or benign.

A dimeric, pentameric, or hexameric binding molecule as provided herein can be genetically engineered such that its antigen-binding domains are encoded by sequences known to specifically bind a TNF superfamily receptor protein. Many groups have published sequences of variable regions of monoclonal antibodies, most of the IgG isotype that are characterized and are known to specifically bind to a TNF superfamily receptor, e.g., DR5. Non-limiting immunoglobulin variable domain sequences that are known to specifically bind to DR5 are provided in Tables 2 and 3. Other monoclonal antibody sequences specific for other members of the TNF superfamily of receptor proteins have been published. One of skill in the art is capable of engineering these published sequences into immunoglobulin structures, such as an IgG, IgA, IgM structure, or biologically active or functional fragments thereof (such as scFv fragments and the like, as discussed above). Methods for genetically engineering cloned variable regions into immunoglobulin domains, and expressing and purifying such constructs are published and within the capability of one skilled in the art.

Thus, in certain aspects, a TNF superfamily receptor protein binding domain as provided herein comprises six immunoglobulin complementarity determining regions HCDR1, HCDR2, HCDR3, LCDR1, LCDR2, and LCDR3, or the six immunoglobulin complementarity determining regions with one, two, three, four, or five single amino acid substitutions in one or more CDR, of an anti-DR5 mAb comprising the VH and VL amino acid sequences SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; SEQ ID NO: 47 and SEQ ID NO: 48; SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 82 and SEQ ID NO: 83; SEQ ID NO: 84 and SEQ ID NO: 85; SEQ ID NO: 86 and SEQ ID NO: 87; or SEQ ID NO: 88 and SEQ ID NO: 89; respectively, or the ScFv amino acid sequence SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

TABLE 2

Anti-DR5 Antibody VH and VL Sequences

| SEQ ID | VH or Heavy Chain | SEQ ID | VL or Light Chain | Reference |
|---|---|---|---|---|
| 1 | EVQLVQSGGGVERPGGSLRLSCAASGFTFDDYGMS WVRQAPGKGLEWVSGINWNGGSTGYADSVKGRV TISRDNAKNSLYLQMNSLRAEDTAVYYCAKILGAG RGWYFDLWGKGTTVTSS | 2 | SSELTQDPAVSVALGQTVRITCQGDSLRSYYAS WYQQKPGQAPVLVIYGKNNRPSGIPDRFSGSSSG NTASLTTTGAQAEDEADYYCNSRDSSGNHVVFG GGTKLTVL | U.S. Patent App. Pub. No. 20060269555A1 |
| 3 | EVQLVQSGGGVERPGGSLRLSCAASGFTFDDYAMS WVRQAPGKGLEWVSGINWQGGSTGYADSVKGRV TISRDNAKNSLYLQMNSLRAEDTAVYYCAKILGAG RGWYFDYWGKGTTVTSS | 4 | SELTQDPAVSVALGQTVRITCGDSLRSYYASW YQQKPGQAPVLVIYGANNRPSGIPDRFSGSSSGN TASLTITGAQAEDEADYYCNSADSSGNHVVFGG GTKLTVL | U.S. Pat. No. 8,029,783 |
| 5 | QVQLQESGPGLVKPSQTLSLTCTVSGGSISSGDYFW SWIRQLPGKGLECIGHIHNSGTTYYNPSLKSRVTISV DTSKKQFSLRLSSVTAADTAVYYCARDRGGDYYY GMDVWGQGTTVTSS | 6 | EIVLTQSPGTLSLSPGERATLSCRASQGISRSYLA WYQQKPGQAPSLLIYGASSRATGIPDRFSGSGSG TDFTLTISRLEPEDFAVYYCQQFGSSPWTFGQGT KVEIK | U.S. Pat. No. 7,521,048 |
| 7 | EVQLVESGGGLVQPGGSLRLSCAASGFTFSSYVMS WVRQAPGKGLEWVATISSGGSYTYYPDSVKGRFTI SRDNAKNTLYLQMNSLRAEDTAVYYCARRGDSMI TTDYWGQGTLVTSSASTKGPSVFPLAPSSKSTSGG TAALGCLVKDYFPEPVTVSWNSGALTSGVHTFPAV LQSSGLYSLSSVVTVPSSSLGTQTYICNVNHKPSNT KVDKRVEPKSCDKTHTCPPCPAPELLGGPSVFLPP KPKDTLMISRTPEVTCVVVDVSHEDPEVKFNWYVD GVEVHNAKTKPREEQYNSTYRVVSVLTVLHQDWL NGKEYKCKVSNKALPAPIEKTISKAKGQPREPQVYT LPPSREEMTKNQVSLTCLVKGFYPSDIAVEWESNG QPENNYKTTPPVLDSDGSFFLYSKLTVDKSRWQQG NVFSCSVMHEALHNHYTQKSLSLSPGK | 8 | DIQMTQSPSSLSASVGDRVTITCKASQDVGTAVA WYQQKPGKAPKLLIYWASTRHTGVPSRFSGSGS GTDFTLTISSLQPEDFATYYCQQYSSYRTFGQGT KVEIKRTVAAPSVFIFPPSDEQLKSGTASVVCLLN NFYPREAKVQWKVDNALQSGNSQESVTEQDSK DSTYSLSSTLTLSKADYEKHKVYACEVTHQGLS SPVTKSFNRGEC | U.S. Pat. No. 7,790,165 |
| 9 | QIQLVQSGPE LKKPGETVKI SCKASGYTFT DFSMNWVKQA PGKGLKWMGW INTETGEPTY ADDFKGRFAL SMETSASTAY LQINNLKNED TATYFCVRID YWGQGTTLTV SS | 10 | DVVMTQTPLS LPVSLGDQAS ISCRSSQSLV HSNGNTYLHW YLQKPGQSPK LLIYKVSNRF SGVPDRFSGS GSGTDFTLKI SRVEAEDLGV YFCFQSTHVP HTFGGGTKLE IKR | U.S. Pat. No. 7,893,216 |
| 11 | MDWTWRILFLVAAATSAHSQVQLVQSGAEMKKPG ASVKVSCKTSGYTFTNYKINWVRQAPGQGLEWMG WMNPDTSTGYPQKFQGRVTMTRNTSISTAYMELS SLRSEDTAVYYCARSYGSGSYYRDYYYGMDVWG QGTTVTSS | 12 | MEAPAQLLFLLLLWLPDTTGEIVLTQSPATLSLS PGERATLSCRASQSVSSYLAWYQQKPGQAPRLL IYDASNRATGIPARFSGSGSGTDFTLTISSLEPEDF AVYYCQQRSNWPLTFGGGTKVEIKR | U.S. Pat. No. 7,115,717 |
| 13 | MKHLWFFLLL VAAPRWVLSE VQLQQSGPEL VKPGASVKIS CKASGYSFIG YFMNWMKQSH GKSLEWISRF NPYNGDTFYN QKFKGKATLT VDKSSTTAHM ELLSLTSEDS AVYFCGRSAY YFDSGGYFDY WGQGTTLTVS SASTKGPSVF PLAPSSKSTS GGTALLGCLV KDYFPEPVTV SWNSGALTSG VHTFPAVLQS SGLYSLSSVV TVPSSSLGTQ TYICNVNHKP SNTKVDKRVE PKSCDKTHTC PPCPAPELLG GPSVFLPPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPRSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K | 14 | MVLQTQVFIS LLLWISGAYG DVVMTQTPLS LPVSLGDQAS ISCRSSQSLV HSNGNTYLHW YLQKPGQSPK LLIYKVSNRF SGVPDRFSGS GSGTDFTLKI SRVEAEDLGI YFCSQSTHVP WTFGGGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC | EP Patent Publication No. EP2636736A1 |
| 15 | QVQLVQSGSELKKPGASVKVSCKASGYTFTDFSMN WVRQAPGQGLEWMGWINTETGEPTYADDFKGRFV FSLDTSVSTAYLQISSLKAEDTAVYYCARIDYWGQ GTTVTSS | 16 | DIVMTQSPLSLPVTPGEPASISCRSSQSLVHSNGN TYLHWYLQKPGQSPQLLIYKVSNRFSGVPDRFS GSGSGTDFTLKISRVEAEDVGVYYCFQSTHVPHT FGQGTKLEIKR | PCT Publication No. WO 2014/063368 A1 |
| 17 | MGXLGLSWVFLVVILEGVQCEVHLVESGGGLVRPG GSLKLSCAASGFAFSSYDMSWVRQTPEKRLEWVA YISDGGGITYYPDTMKGRFTISRDNAKNTLSLQMSS LKSEDTAMYYCARHITMVVGPFAYWGQGTLVTVS AASTKGPSVFPLAPCSRSTSGGTAALGCLVKDYFPE PVTVSWNSGALTSGVHTFPAVLQSSGLYSLSSVVTV PSSSLGTQTYICNVNHKPSNTKVDKRVEPKSCDKTH TCPPCPAPELLGGPSVFLPPKPKDTLMISRTPEVTC VVVDVSHEDPEVKFNWYVDGVEVHNAKTKPREEQ YNSTYRVVSVLTVLHQDWLNGKEYKCKVSNKGLP APIEKTISKAKGQPREPQVYTLPPSREEMTKNQVSL | 18 | MRLPAQLLGLLMLWVSGSSGDIQMTQSSSSFSV SLGDRVTITCKASEDIYNRLAWYQQKPGNAPRL LISGATSLETGVPSRFSGSGSGKDYTLSITSLQTE DVATYYCQQYWSTPLTFGAGTKLELKRAVAAP SVDIFPPSDEQLKSGTASVVCLLNNFYPREAKVQ WKVDNALQSGNSQESVTEQDSKDSTYSLSSTLT LSKADYEKHKVYACEVTHQGLSSPVTKSFNRGE C | U.S. Pat. No. 7,897,730 |

TABLE 2-continued

Anti-DR5 Antibody VH and VL Sequences

| SEQ ID | VH or Heavy Chain | SEQ ID | VL or Light Chain | Reference |
|---|---|---|---|---|
| | TCLVKGFYPSDIAVEWESNGQPENNYKTTPPVLDS DGSFFLYSKLTMDKSRWQQGNVFSCSVMHEALHN HYTQKSLSLSPGK | | | |
| 19 | MELGLSWVFLVVILEGVQCEVQLQQSGPELVKPGA SVRMSCKASGYTFTSYFIHWVKQRPGQGLEWIGWI YPGNVNTKYSEKFKGKATLTADKSSTAYMQFSSL TSEDSAVYFCARGEAGYFDYWGQGTTLTVSSASTK GPSVFPLAPCSRSTSGGTAALGCLVKDYFPEPVTVS WNSGALTSGVHTFPAVLQSSGLYSLSSVVTVPSSSL GTQTYICNVNEKPSNTKVDKRVEPKSCDKTHTCPP CPAPELLGGPSVFLFPPKPKDTLMISRTPEVTCVVVD VSHEDPEVKFNWYVDGVEVENAKTKPREEQYNST YRVVSVLTVLHQDWLNGKEYKCKVSNKGLPAPIE KTISKAKGQPREPQVYTLPPSREEMTKNQVSLTCLV KGFYPSDIAVEWESNGQPENNYKTTPPVLDSDGSFF LYSKLTMDKSRWQQGNVFSCSVMEEALENHYTQK SLSLSPGK | 20 | MRLPAQLLGLLMLWVSGSSGDIVMTQSHKFMS TSVGDRVSITCKASQDVSTAVAWYQQKPGQSPR LLIYWASTRHTGVPDRFTGSGSGTDYTLTISSVQ AEDQALYYCQQHYRTPWTFGGGTKLEIKRAVA APSVDIFPPSDEQLKSGTASVVCLLNNFYPREAK VQWKVDNALQSGNSQESVTEQDSKDSTYSLSST LTLSKADYEKEKVYACEVTEQGLSSPVTKSFNR GEC | U.S. Pat. No. 7,897,730 |
| 21 | QVQLVQSGAEVKKPGASVKVSCKASGYTFTSYDIN WVRQATGQGLEWMGWMNPNSDNTGYAQKFQGR VTMTRNTSISTAYMELSSLRSEDTAVYYCARWNHY GSGSHFDYWGQGTLVTVSS | 22 | DIQMTQSPSSLSASVGDRVTITCRASQSISIYLNW YQQKPGKAPKLLIYAASSLQSGVPLRFSGSGSGT DFTLTISSLQPEDIATYYCQQSYKTPLTFGGGTK VEIK | U.S. Pat. No. 7,521,048 |
| 23 | QVQLQESGPGLVKPSQTLSLTCTVSGGSISSGGHYW SWIRQHPGKGLEWIGYIYYSGSTYYNPSLKSRVTIS VDTSKNQFSLKLSSVTAADTAVYYCARDDSSGWGF DYWGQGILVTVSS | 24 | DIQMTQSPSSLSASVGDRVTITCRASQGLRNDLG WFQQKPGKVTKRLIYAASSLQRGVPSRFSGSGS GTEFTLTISSLQPEDFATYCLQHYSFPWTFGQG TKVEIK | U.S. Pat. No. 7,521,048 |
| 25 | QVQLQESGPGLVKPSQTLSLTCTVSGGSISSGGHYW SWIRQHPGKGLEWIGYIYYSGSAYYNPSLKSRVTIS VDTSKNQFSLKLSSVTAADTAVYYCARDDSSGWGF DYWGQGILVTVSS | 26 | DIQMTQSPSSLSASVGDRVTITCRASQGLRNDLG WFQQKPGKAPKRLIYAASSLQRGVPSRFSGSGS GTEFTLTISSLQPEDFTTYFCLQHNSFPWTFGQGT KVEIK | U.S. Pat. No. 7,521,048 |
| 27 | QVQLQESGPGLVKPSQTLSLTCTVSGGSISSGGHYW SWIRQHPGKGLEWIGYIYYSGSAYYNPSLKSRVTIS VDTSKNQFSLKLSSVTAADTAVYYCARDDSSGWGF DYWGQGILVTVSS | 28 | DIQMTQSPSSLSASVGDRVTITCRASQGLRNDLG WFQQKPGKAPKRLIYAASSLQRGVPSRFSGSGS GTEFTLTISSLQPEDFTTYFCLQHNSFPWTFGQGT KVEIK | U.S. Pat. No. 7,521,048 |
| 29 | QVQLVESGGGLVKPGGSLRLSCAASGFTFSDYYMN WIRQAPGKGKAPWVSHISSSGSILDYADSVKGRFTISR DNAKNSLYLQMNSLRVEDTAVYYCARDGAAAGT DAFDLWGQGTMVTVSS | 30 | DIQMTQSPSSLSASVGDRVTITCRSSQSISNYINW YQQRPGKAPNLLIHDVSSFQDAVPSRFSRSGSGT VFTLTISSLQPEDFATYFCQQTYITPFTFGPGTKV DIK | U.S. Pat. No. 7,521,048 |
| 31 | QVQLVESGGGVVQPGRSLRLSCAASGFTFSYYGIH WVRQAPGKGLEWVAVIWYDGSNKYYADSVKGRF TISRDNSKNTLYLQMNSLRAEDTAVYYCARGRYSS SSWWYFDLWGRGTLVTVSS | 32 | DIQMTQSPSSLSASVGDRVTITCRASQGISNYLA WYQQKPGKVPKLLIYAASTLQSGVPSRFSGSGS GTDFTLTISSLQPEDVATYYCQKYNSAPLTFGGG TKVEIK | U.S. Pat. No. 7,521,048 |
| 33 | QVQAEQSGPGLVKPSETLSLTCTVSGGSISNYYWS WIRQPPGKGLEWIGYIYYSGSTKYNPSLKSRVTISV DTSKNQFSLKLTSVTTADTAVYYCARDSPRGFSGY EAFDSWGQGTLVTVSS | 34 | DIVMTQSPDSLAVSLGERATINCKSSQSVLYRSN NKIYLAWYQQKPGQPPKLLIYWASTRESGVPDR FSGSGSGTDFTLTISSLLAEDVAVYYCQQYYSTP FTFGPGTKVDIK | U.S. Pat. No. 7,521,048 |
| 35 | QVQLQESGPGLVKPSQTLSLTCTVSGGSISSDNYYW SWIRQHPGKGLEWIGYIYYSGSTYYNPSLKSRVTIS VDTSKNQFSLKLSSVTAADTAVYYCARGVNWNFL FDIWGQGTMVTVSS | 36 | DIVMTQSPLSLPVTPGEPASISCRSSQSLLRRNGY NYLDWYLQKPGQSPQLLIYLGSNRASGVPDRFS GSGSGTDFTLKISRVEAEDVGVYYCMQALQTPL TFGGGTEVEIK | U.S. Pat. No. 7,521,048 |
| 37 | QVQLVESGGGLVKPGGSLRLSCAASGFTFSDYYMS WIRQAPGKGLEWVSYISRSGSTIYYADSVKGRFTIS RDNAKNSLYLQMNSLRAEDTAVYYCARSLGGMDV | 38 | DIVMTQFPDSLAVSLGERATINCKSSQSVLHSSN NKNYLTWYQLKPGQPPKLLIYWASTRESGVPDR FSGSGSGTDFTLTISSLQAEDVAVYYCHQYYSTP | U.S. Pat. No. 7,521,048 |
| 39 | QVQLVESGGGVVQPGRSLRLSCAASGFTFNNYGM HWVRQAPGKGLEWVAVIWYDGSNKYYADSVKGR FTISRDNSKNTLYLQMNSLRAEDTAVYYCARDRTV YSNSSPFYYYYYGMDVWGQGTTVTVSS | 40 | DIQMTQSPSSLSASVGDRVTITCRTSQSISTYLNW YQQKPGKAPKLLISATSSLQSGVPSRFSGSGSGT DFTLTISSLQPEDFATYYCQQSYSTPLTFGGGTK VEIK | U.S. Pat. No. 7,521,048 |
| 41 | QVQLVESGGGVVQPGRSLRLSCAASGFTFSTYGMH WVRQAPGKGLEWVAVIWYDGSNKYYADSVKGRF TISRDNSKNTLYLQMNSLRAEDTAVYYCARDRTVY SSSSPFYYYYYGMDVWGQGTTVTVSS | 42 | DIQMTQSPSSLSASVGDRVTITCRASQSISSYLNW YQQKPGKAPKLLISATSSFQSGVPSRFSGSGSGT DFTLTISSLQPEDFAAYYCQQSYSTPLTFGGGTK VEIK | U.S. Pat. No. 7,521,048 |
| 43 | QVQLQQWGARLLKPSETLSLTCAVYGGSFSGYYW SWIRQPPGKGLEWIGEINHSGSTNYNPSLKSRVTISV | 44 | DIVMTQSPDSLAVSLGERATINCKSSQSVLHSSN NKNYLVWYQQKPGQPPKLLIYWASTRESGVPD | U.S. Pat. No. 7,521,048 |

TABLE 2-continued

Anti-DR5 Antibody VH and VL Sequences

| SEQ ID | VH or Heavy Chain | SEQ ID | VL or Light Chain | Reference |
|---|---|---|---|---|
| | DTSKNQFSLKLRSVTAADTAVYYCARGGSSGYWY FDLWGRGTLVTVSS | | RFSGSGSGTDFTLTISSLQAEDVAVYYCQQYYST PLTFGGGTKVEIK | |
| 45 | EVQVVESGGGLVKPGGSLRLSCAASGFTFSSYSMN WVRQAPOKGLEWVSSISSSSSYIYADSVKGRFTIS RDNAKNSLYLQMNSLRAEDTAVYYCARGGSSWYG DWFDPWGQGTLVTVSS | 46 | DIQMTQSPSSVSASVGDRVTITCRASQGISSWLV WYQQKPGKAPKLLIYAASSLQSGVPSRFSGSGS GTDFTLTISSLQPEDFATYYCQQANSFPFTFGGG TKVEIK | U.S. Pat. No. 7,521,948 |
| 47 | QLVESGGGVVQPGRSLRLSCAASGFTFSSYGMHW RQAPGKGLEWVAVIWYDGRNKYYADSVKGRFTIS RDNSKNTLYLQMNSLRAEDTAVYYCAREVGYCTN GVCSYYYYGMDVWGQGTTVTVSS | 48 | DIQMTQSPSSLSASVGDRVTITCRASQGISNYLA WFQQKPGKAPKSLIYAASSLQSGVPSKFSGSGSG TDFTLTISSLQPEDFATYYCQQYNSYPLTFGGGT KVEIK | U.S. Pat. No. 7,521,048 |
| 49 | QVQLQESGPGLVKPSQTLSLTCSVSGGSISSGGYYW SWIRQHPGKGLEWIGYIYYSGSTYCNPSLKSRVTIS VDTSKNQFSLKLSSVTAADTAVYYCARDNGSGSYD WFDPWGQGILVTVSS | 50 | DIQMTQSPSSVSASVGDRVTITCRASQGISSWLA WYQQKPGKAPKFLIVASSFQSGVPSRFSGSGSG TDFILTISSLQPEDFATYYCQQANSFPRTFGQGT KVEIK | U.S. Pat. No. 7,521,048 |
| 51 | QVQMQESGPGLVKPSQTLSLTCTVSGGSISSGDYY WSWIRQHPGKNLEWIGYIYYSGSTYYNPSLKSRVTI SVDTSKNQFSLKLSSVTAADTAVYYCARDNGSGSY DWFDPWGQGTLVTVSS | 52 | DIQMTQSPSSVSASVGDRVTITCRASQGISSWLA WYQQKPGKAPKFLIVASSLQSGVPSRFSGSGSG TDFTLTISSLQPEDFATYYCQQANSFPRTFGQGT KVEIK | U.S. Pat. No. 7,521,048 |
| 53 | KVQLQQSGAELVKPGASVKLSCKASGYTFDYTIH WVKQRSGQGLEWIGWFYPGGGYIKYNEKFKDRAT LTADKSSNTVYMELSRLTSEGSAVYFCARHEEGIYF DYWGQGTTLTVSS | 54 | DIAMTQSHKFMSTLVGDRVSITCKASQDVNTAI AWYQQKPGQSPKLLIYWASTRHTGVPDRFTGSG SGTDYTLTISSMEAEDAATYYCQQWSSNPLTFG AGTKLELKRA | U.S. Pat. No. 7,229,617 |
| 55 | KVQLQQSGAELVKPGASVKLSCKASGYTFTDYTIH WVKQRSGQGLEWIGWFYPGGGYIKYNEKFKDRAT LTADKSSNTVYMELSRLTSEDSAVYFCARHEEGIYF DYWGQGTTLTVSS | 56 | DIVMTQSHKFMSTSVGDRVSITCKASQDVNTAI AWYQQKPGQSPKLLIYWASTRHTGVPDRFTGSG SGTDYTLTISSVQAEDLALYYCQQHYTTPFTFGS GTKL | U.S. Pat. No. 7,229,618 |
| 82 | MDLMCKKMKHLWFFLLLVAAPRWVLSQLQLQES GPGLVKPSETLSLTCTVSGGSIISKSSYYWGWIRQPPG KGLEWIGSIYYSGSTFYNPSLKSRVTISVDTSKNQFS LKLSSVTAADTAVYYCARLTVAEFDYWGQGTLVT VSSAS | 83 | MEAPAQLLFLLLLWLPDTTGEIVLTQSPATLSLS PGERATLSCRASQSVSSFLAWYQQKPGQAPRLLI YDASNRATGIPARFSGSGSGTDFTLTISSLEPEDF AVYYCQQRSNWPLTFGPGTKVDIKRT | U.S. Pat. No. 7,115,717 |
| 84 | MDLMCKKMKHLWFFLLLVAAPRWVLSQLQLQES GPGLVKPSETLSLTCTVSGGSISISRSNYWGWIRQPP GKGLEWIGNVYYRGSTYYNSSLKSRVTISVDTSKN QFSLKLSSVTADTAVYYCARLSVAEFDYWGQGIL VTVSSAS | 85 | MEAPAQLLFLLLLWLPDTTGEIVLTQSPATLSLS PGERATLSCRASQSVSSFLAWYQQKPGQAPRLLI YDASNRATGSPARFSGSGSGTDFTLTISSLEPEDF AVYYCQQRSDWPLTFGPGTKVDIKRT | U.S. Pat. No. 7,115,717 |
| 86 | MDLMCKKMKHLWFFLLLVAAPRWVLSQLQLQES GPGLVKPSETLSLTCTVSGGSISSSSYYWGWVRQPP GKGLEWIGSIHYSGSTFYNPSLKSRVTISVDTSKNQF SLKLSSVTAADTTVYYCARQGSTVVRGVYYYGMD VWGQGTTVTVSSAS | 87 | METPAQLLFLLLLWLPDTTGEIVLTQSPGTLSLSP GERATLSCRASQSVSSSYLAWYQQKPGQAPRLL IYGASSRATGIPDRFSGSGSGTDGTLTISRLEPEDF AVYYCQQYGSSPLYTFGQGTKLEIKRT | U.S. Pat. No. 7,115,717 |
| 88 | MEFGLSWLFLVAILKGVQCEVQLLESGGGLVQPGR SLRLSCAASGFTFSSYAMSWVRQAPGKGLEWVSAI SGSGGSRYYADSVKGRFTISRDNSKNTLYLQMNSL RAEDTAVYYCAKESSGWFGAFDYWGQGTLVTVSS | 89 | MSPSQLIGFLLLWVPASRGEIVLTQSPDFQSVTPK EKVTITCRASQSIGSSLHWYQQKPDQSPKLLIKY ASQSFSGVPSRFSGSGSGTDFTLTINSLEAEDAAA YYCHQSSSLPITFGQGTRLEIKR | U.S. Pat. No. 7,115,717 |

TABLE 3

Anti DR5 ScFv Sequences

| SEQ ID | SEQUENCE | Reference |
|---|---|---|
| 57 | EVQLVQSGGGVERPGGSLRLSCAASGFTFDDYGMSWVRQAPGKGLEWVSGINWNGGSTGYAD SVKGRVTISRDNAKNSLYLQMNSLRAEDTAVYYCAKILGAGRGWYFDLWGKGTTVTVSSGGG GSGGGGSGGGGSSELTQDPAVSALGQTVRITCQGDSLRSYYASWYQQKPGQAPVLVIYGKNN RPSGIPDRFSGSSSGNTASLTITGAQAEDEADYYCNSRDSSGNHVVFGGGTKLTVLG | U.S. Patent Application Publication No. 2006/0269555 |
| 58 | EVQLVETGGGLVQPGGSLRLSCAASGFTFSSYAMSWVRQAPGKGLEWVSAISGSGGSTYYADS VKGRFTISRDNSKNTLYLQMNSLRAEDTAVYHCARGGYSSSRSAAYDIWGQGTLVTVSSGGGG SGGGGSGGGGSSELTQDPAVSALGQTVRITCQGDSLRSYYASWYQQKPGQAPVLVIYGKNNR PSGIPDRFSGSSSGNTASLTITGAQAEDEADYYCNSRDSSGNHVVFGGGTKLTVLG | U.S. Patent Application Publication No. 2006/0269556 |

TABLE 3-continued

Anti DR5 ScFv Sequences

| SEQ ID | SEQUENCE | Reference |
|---|---|---|
| 59 | QVQLVQSGAEVKKPGASVKISCEGSGYTFNSYTLHWLRQAPGQRLEWMGRINAGNQNTKYSQ NFQGRLSITRDTSATTAYMELSSLRSEDTGVYYCARVFTVSFGMDVWGRGTLVTVSSGGGGSG GGGSGGGGSAQSVLTQPPSASGI1PGQRVTISCSGGGSNIGRNSVSWYQQLPGTAPKLILYSNNQRP PSGVPDRFSGSKSGTSASLAISGLRSEDEALYYCAAWDDSLSGGVFGGGTKLTVLG | U.S. Patent Application Publication No. 2006/0269557 |
| 60 | QVQLVESGGGLVQPGGSLRLSCAASGFTFSSYAMSWVRQAPGKGLEWVSAISGSGGSTYYADS VKGRFTISRDNSKNTLYLQMNSLRAEDTAVYYCAKVHRPGRSGYFDYWGRGTLVTVSSGGGGS GGGGSGGGGSSELTQDPAVSVALGQTVRITCQGDSLRSYYASWYQQKPGQAPVLVIYGKNNRP SGIPDRFSGSSSGNTASLTITGAQAEDEADYYCNSRDSSGNHVVFGGGTKLTVLG | U.S. Patent Application Publication No. 2006/0269558 |
| 61 | QVQLQQSGAEVKKPGASVRVSCQASGYSLSEYYIHWVRQAPGQGLEWMGWLNPNSGVTDYA QKFQGRVSMIRDTSISTAYMELSSLFFNDTAVYFCARGNGDYWGKGTLVTVSPGGGGSGGGGS GGGGSSELTQDPAVSVALGQTVRITCQGDSLRSYYTNWFQQKPGQAPLLVVYAKNKRPSGIPDR FSGSSSGNTASLTITGAQAEDEADYYCHSRDSSGWVFGGGTKLTVLG | U.S. Patent Application Publication No. 2006/0269559 |
| 62 | QVQLVQSGGGVVQPGRSLRLSCAASGFTFSPDAMHWVRQAPGKGLEWMGVISFDGSQTFYADS VKGRFTISRDNSQNTLYLQMNSLRSDDTAVYYCARAPARFFPLHFDIWGRGTMVTVSSGGGGS GGGGSGGGGSALSSELTQDPAVSVALGQTVRITCQGDSLRTHYASWYHQRPGRAPVLVNYPKD SRPSGIPDRFSGSSSGNTASLTIIGAQAADEGDYYCQSRDSSGVLFGGGTKVTVLG | U.S. Patent Application Publication No. 2006/0269560 |
| 63 | EVQLVESGGGLVQPGGSLRLSCAASGFTFSSYWMSWVRQAPGKGLEWVANIKQDGSEKYYVD SVKGRFTISRDNAKNSLYLQMNSLRAEDTAVYYCARDFSGYGDYLDYWGKGTLVTVSSGGGG SGGGGSGGGGSAQSALTQPPSASGSPGQSVTISCTGTSSDIGNYNYVSWYQQHPGKAPKLMIYE VNERPSGVPDRFSGSKSGNTASLTVSGLRPEDEADYYCSSYAGNNAVIFGGGTQLTVLG | U.S. Patent Application Publication No. 2006/0269561 |
| 64 | QVQLVQSGAEVKKPGASVKVSCKASGYTFTTHAMHWVRQAPGQSLEWMGWINTGNGNTKYS QSFQGRVSITRDTSANTAYMELSSLKSEDTAMYYCARASRDSSGYYYVPGDFFDIWGQGTLVT VSSGGGGSGGGGSGGGGSAQSALTQPASVSGSPGQSITISCTGSRSDIGGYNFVSWYQQHPGKAPP KLLIYDVYNRPSGISDHFSGSKSDNTASLTISGLQSEDDADYYCSSYAGYHTWIFGGGTKVTVLG | U.S. Patent Application Publication No. 2006/0269562 |
| 65 | EVQLVQSGAEVKKPGASVKLSCKASGYTLVNYFMHWVRQAPGQGPEWMGMINPSGGTTKNR QKFQDRVTMTRDTSTRTVYMELSGLTSEDTAVYYCATDFKGTDILFRDWGRGTLVTVSSGGGG SGGGGSGGGGSAQSVLTQPPSASGTPGQRVSISCSGSSSNIGSNTVIWYQQLPGTAPKLLMYSND RRPSGVPDRFSGSKSGTSASLAISGLQSEDEADYYCATWDDSLNGHYVFGTGTKLTVLG | U.S. Patent Application Publication No. 2006/0269563 |
| 66 | QMQLVQSGGGLVKPGGSLRLSCAASGFTFSDYYMSWIRQAPGKGLEWVSAISGSGGSTYYADS VKGRFTISRDNSKNTLYLQMNSLRAEDTAVYYCARGGSTFDIWGRGTMVTVSSGGGGSGGGGS GGGGSAQPVLTQPPSASGTPGQRVTISCSGSNSNIGSRPVNWYQQLPGTAPKLLIQGNNQRPSGV PDRFSGSKSGTSASLAISGLQSEDEADYYCAAWDDSLTGYVFGPGTKLTVLG | U.S. Patent Application Publication No. 2006/0269564 |
| 67 | QMQLVQSGGAVVQPGRSLRLSCAASGFTFSSYGMHWVRQAPGKGLEWVAVISYDGSIKYYAD SVKGRFTISRDNSKNTLYLQMNSLRAEDTAVYYCARERLRGLDPWGQGTMVTVSSGGGGSGG GGSGGGGSSELTQDPAVSVALGQTVRITCQGDSLRSYYASWYQQKPGQAPVLVIYGKNNRPSGI PDRFSGSSSGNTASLTITGAQAEDEADYYCNSRDSSGNHVVFGGGTKLTVLG | U.S. Patent Application Publication No. 2006/0269565 |
| 68 | EVQLVETGGGLVQPGGSLRLSCAASGFTFSPYYMSWVRQAPGKGLEWVSAISGSGGSIYYADSV KGRFTISRDNSKNTLYLQMNSLRAEDTALYYCARGASGPDYWGRGTMVTVSSGGGGSGGGGS GGGGSAQSVLTQPPSVSAAPGQKVTISCSGSTSNIGNNYVSWYQQVPGTAPKLLIYDNNKRPSGI PDRFSGSKSGTSATLGITGLQTGDEADYYCGTWDSSLSALVFGGGTKVTVLG | U.S. Patent Application Publication No. 2006/0269566 |
| 69 | QVQLQQSGAEVKTPGSSVKVSCKASGGTFRNNAISWVRQAPGQGLEWMGGFIPKFGTTNHAQK FQGRVTMTADDSTNTVYMELSSLRSEDTAVYYCARGGAYCGGGRCYLYGMDVWGQGTLVTV SSGGGGSGGGGSGGGGSAQAVVIQEPSLTVSPGGTVTLTCGSSTGAVTSGHYPYWFQQKPGQAP RTLIYDTSNKRSWTPARFSGSLLGGKAALTLSGAQPEDEAEYYCLVSYSGSLVVFGGGTKLTVL G | U.S. Patent Application Publication No. 2006/0269567 |
| 70 | EVQLLESGGGLVQPGGSLRLSCAASGFTFSSYAMSWVRQAPGKGLEWVSAISGSGGSTYYADSV KGRFTISRDNSKNTLYLQMNSLRAEDTAVYYCVKGAWLDYWGRGTMVTVSSGGGGSGGGGS GGGGSALNFMLTQPHSVSESPGKTVTISCTGSSGSVARNYVQWYQRPGSAPTIVIYEDNRRPSG VPGRFSGSIDRSSNSASLTISGLQTEDEADYYCQSYNYNTWVFGGGTKLTVLG | U.S. Patent Application Publication No. 2006/0269568 |
| 71 | EVQLVQSGAEVKKPGASVKVSCRASGYTFTSYGITWVRQAPGQGLEWMGWISAYNGKTNYVQ ELQGRVTMTTDTSTSTVYMELTSLRSDDTAVYYCARRGNNYRFGYFDFWGQGTLVTVSSGGG GSGGGGSGGGGSALETTLTQSPGTLSLSPGERATLSCRASQSISSSNLAWYQQKPGRAPRLLIYGA ASSRAIGPDRFSGSGSGTDFTLTISRLEAEDFAVYYCQQYGSSPITFGQGTRLEIKR | U.S. Patent Application Publication No. 2006/0269569 |
| 72 | QVQLQQSGPG LVKPSQTLSL TCAISGDSVS STTVAWDWIR QSPSRGLEWL GRTYYRSKWY NEYAVSVKSR ITINVDTSKN QISLQLNSVT PEDTAVYYCA REPDAGRGAF DIWQGGTTVT SPLRWGRFGW RGLGRGWLRS PVTQSPGTLS LSPGERATLS CRASQSVSSS HLAWYQQKPG QAPRLLIYGA SSRATGIPDR FSGSGSGTDF TLTISSLEPE DFAVYYCQQR SNWPPRAVFG QGTRLEIK | U.S. Pat. No. 8,097,704 |
| 73 | QVQLQQSGPG RVQPSQTLSL TCAISGDSVS NNNAAWYWIR QSPSRGLEWL GRTYYRSKWY NDYAVSVKSR ITISPDTSKN QFSLQLNSVT PEDTAVYYCA RRGDGNSYFD YWGQGTLVTV | U.S. Pat. No. 8,097,705 |

TABLE 3-continued

Anti DR5 ScFv Sequences

| SEQ ID | SEQUENCE | Reference |
|---|---|---|
| | SSGILRWGRF GWRGLGRGWL EIVLTQSPGT LSLSPGERAT LSCRASQSVS SGYVSWYRQK PGQAPRLLIY GASTRATGIP DRFSGSGSGT DFTLTISRLE PEDFAVYYCH QYGSSPNTYG QGTKVGIK | |

In certain aspects the DR5 binding domain comprises a VH and a VL, wherein the VH and VL comprise amino acid sequences at least 60%, at least 65%, at least 70%, at least 75%, at least 80%, at least 85%, at least 90%, at least 95% or 100% identical to SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; SEQ ID NO: 47 and SEQ ID NO: 48; SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 82 and SEQ ID NO: 83; SEQ ID NO: 84 and SEQ ID NO: 85; SEQ ID NO: 86 and SEQ ID NO: 87; or SEQ ID NO: 88 and SEQ ID NO: 89; respectively, or where the VH and VL are situated in an ScFv comprising an amino acid sequence at least 60%, at least 65%, at least 70%, at least 75%, at least 80%, at least 85%, at least 90%, at least 95% or 100% identical to SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

While a variety of different dimeric, pentameric, and hexameric binding molecules can be contemplated by a person of ordinary skill in the art based on this disclosure, and as such are included in this disclosure, in certain aspects, a binding molecule as described above is provided in which each binding unit comprises two IgA or IgM heavy chains each comprising a VH situated amino terminal to the IgA or IgM constant region or fragment thereof, and two immunoglobulin light chains each comprising a VL situated amino terminal to an immunoglobulin light chain constant region.

Moreover in certain aspects, at least one binding unit of the binding molecule, or at least two, at least three, at least four, at least five, or at least six binding units of the binding molecule, comprises or comprise two of the DR5 binding domains as described above. In certain aspects the two DR5 binding domains in the at least one binding unit of the binding molecule, or at least two, at least three, at least four, at least five, or at least six binding units of the binding molecule, can be different from each other, or they can be identical.

In certain aspects, the two IgA or IgM heavy chains within the at least one binding unit of the binding molecule, or at least two, at least three, at least four, at least five, or at least six binding units of the binding molecule, are identical. In certain aspects, two identical IgA or IgM heavy chains within at least one binding unit, or within at least two, at least three, at least four, at least five, or at least six binding units of the binding molecule comprise the heavy chain variable domain amino acid sequences as disclosed in Tables 2 and 3.

In certain aspects, the two light chains within the at least one binding unit of the binding molecule, or at least two, at least three, at least four, at least five, or at least six binding units of the binding molecule, are identical. In certain aspects, two identical light chains within at least one binding unit, or within at least two, at least three, at least four, at least five, or at least six binding units of the binding molecule are kappa light chains, e.g., human kappa light chains, or lambda light chains, e.g., human lambda light chains. In certain aspects, two identical light chains within at least one binding unit, or within at least two, at least three, at least four, at least five, or at least six binding units of the binding molecule each comprise the light chain variable domain amino acid sequences as disclosed in Tables 2 and 3.

In certain aspects at least one, at least two, at least three, at least four, at least five, or at least six binding units of a dimeric, pentameric, or hexameric binding molecule provided by this disclosure comprises or each comprise two identical IgA or IgM heavy chain constant regions each comprising identical heavy chain variable domain amino acid sequences as disclosed in Tables 2 and 3, and two identical light chains each comprising identical heavy chain variable domain amino acid sequences as disclosed in Tables 2 and 3. According to this aspect, the DR5 binding domains in the at least one binding unit of the binding molecule, or at least two, at least three, at least four, at least five, or at least six binding units of the binding molecule, can be identical. Further according to this aspect, a dimeric, pentameric, or hexameric binding molecule as provided herein can comprise at least one, at least two, at least three, at least four, at least five, at least six, at least seven, at least eight, at least nine, at least ten, at least eleven, or at least twelve copies of an DR5 binding domain as described above. In certain aspects at least two, at least three, at least four, at least five, or at least six of the binding units can be identical and, in certain aspects the binding units can comprise identical binding domains, e.g., at least two, at least three, at least four, at least five, at least six, at least seven, at least eight, at least nine, at least ten, at least eleven, or at least twelve DR5 binding domains can be identical.

In certain aspects, a dimeric, pentameric, or hexameric TNF superfamily receptor protein binding molecule as provided herein can possess advantageous structural or functional properties compared to other binding molecules. For example, the dimeric, pentameric, or hexameric TNF superfamily receptor protein binding relative to a corresponding bivalent binding molecule having the same antigen binding domains. Biological assays include, but are not limited to ELISA and Western blot caspase assays, and FACS analyses using stains indicative of apoptotic cell death such as annexin-v. In certain aspects a dimeric, pentameric, or hexameric binding molecule as provided herein can trigger apoptosis of a TNF superfamily receptor protein-expressing cell at higher potency than an equivalent amount of a monospecific, bivalent IgG1 antibody or fragment thereof that specifically binds to the same TNF superfamily receptor protein epitope as the TNF superfamily receptor protein binding domain. In certain aspects a dimeric, pentameric, or hexameric binding molecule as provided herein can trigger apoptosis of a DR5-expressing cell at higher potency than an equivalent amount of monospecific, bivalent anti-DR5 monoclonal antibody or fragment thereof, where the antibody is, or comprises the same VH and VL regions as, the antibodies provided in Tables 2 and 3, e.g., Conatumumab (Amgen), Drozitumab (Genentech), or Lexatumumab (HGS/GlaxoSmithKline).

Polynucleotides, Vectors, and Host Cells

The disclosure further provides a polynucleotide, e.g., an isolated, recombinant, and/or non-naturally-occurring polynucleotide, comprising a nucleic acid sequence that encodes a polypeptide subunit of a dimeric, pentameric, or hexameric binding molecule as provided herein. By "polypeptide subunit" is meant a portion of a binding molecule, binding unit, or binding domain that can be independently translated. Examples include, without limitation, an antibody VH, an antibody VL, a single chain Fv, an antibody heavy chain, an antibody light chain, an antibody heavy chain constant region, an antibody light chain constant region, and/or any fragment thereof.

The disclosure further provides a composition comprising two or more polynucleotides, where the two or more polynucleotides collectively can encode a dimeric, pentameric, or hexameric binding molecule as described above. In certain aspects the composition can include a polynucleotide encoding an IgA or IgM heavy chain or fragment thereof, e.g, a human IgA or IgM heavy chain as described above where the IgA or IgM heavy chain comprises at least the VH of a TNF superfamily receptor protein binding domain, and a polynucleotide encoding a light chain or fragment thereof, e.g., a human kappa or lambda light chain that comprises at least the VL of a TNF superfamily receptor protein binding domain. A polynucleotide composition as provided can further include a polynucleotide encoding a J chain, e.g., a human J chain, or a fragment thereof or a variant thereof. In certain aspects the polynucleotides making up a composition as provided herein can be situated on two or three separate vectors, e.g., expression vectors. Such vectors are provided by the disclosure. In certain aspects two or more of the polynucleotides making up a composition as provided herein can be situated on a single vector, e.g., an expression vector. Such a vector is provided by the disclosure.

The disclosure further provides a host cell, e.g., a prokaryotic or eukaryotic host cell, comprising a polynucleotide or two or more polynucleotides encoding a dimeric, pentameric, or hexameric TNF superfamily receptor protein binding molecule as provided herein, or any subunit thereof, a polynucleotide composition as provided herein, or a vector or two, three, or more vectors that collectively encode a dimeric, pentameric, or hexameric TNF superfamily receptor protein binding molecule as provided herein, or any subunit thereof. In certain aspects a host cell provided by the disclosure can express a dimeric, pentameric, or hexameric TNF superfamily receptor protein binding molecule as provided by this disclosure, or a subunit thereof.

In a related aspect, the disclosure provides a method of producing a dimeric, pentameric, or hexameric TNF superfamily receptor protein binding molecule as provided by this disclosure, where the method comprises culturing a host cell as described above, and recovering the binding molecule.

Methods of Use

This disclosure provides improved methods for triggering apoptosis of cells that express TNF superfamily receptor proteins, e.g., malignant or immortalized cells, using a dimeric, pentameric, or hexameric IgA- or IgM-based TNF superfamily receptor protein binding molecule as provided herein. The methods described below can utilize binding molecules comprising TNF superfamily receptor protein binding domains derived from any existing anti-TNF superfamily receptor protein antibodies, including without limitation the antibodies provided in Tables 2 and 3, or variants, derivatives, or analogs thereof, where the dimeric, pentameric, or hexameric TNF superfamily receptor protein binding molecule can provide improved apoptosis-mediated cell death TNF superfamily receptor protein-expressing cells as compared to an equivalent bivalent antibody, fragment, variant, derivative, or analog. Based on this disclosure, construction of a dimeric, pentameric, or hexameric IgA- or IgM-based TNF superfamily receptor protein binding molecule comprising any TNF superfamily receptor protein binding domain of interest is well within the capabilities of a person of ordinary skill in the art. The improved activity can, for example, allow a reduced dose to be used, or can result in more effective killing of cells that are resistant to killing by the original antibody. By "resistant" is meant any degree of reduced activity of an anti-TNF superfamily receptor protein antibody on the TNF superfamily receptor protein-expressing cell.

In certain aspects, this disclosure provides a method for triggering apoptosis, morphogenesis or proliferation in cells which express TNF superfamily receptor proteins, where the method includes contacting a TNF superfamily receptor protein-expressing cell with a dimeric, pentameric, or hexameric binding molecule as described herein, where the binding molecule triggers apoptosis, morphogenesis or proliferation of a TNF superfamily receptor protein-expressing cell at higher potency than an equivalent amount of a monospecific, bivalent IgG1 antibody or fragment thereof that specifically binds to the same TNF superfamily receptor protein epitope as the TNF superfamily receptor protein binding domain.

In yet another aspect a TNF superfamily receptor protein binding molecule as provided herein can facilitate cancer treatment, e.g., by slowing tumor growth, stalling tumor growth, or reducing the size of existing tumors, when administrated as an effective dose to a subject in need of cancer treatment. The disclosure provides a method of treating cancer comprising administering to a subject in need of treatment an effective dose of a TNF superfamily receptor protein binding molecule as provided herein, e.g., a DR5 binding molecule as provided herein.

In certain aspects the TNF superfamily receptor protein-expressing cell is an immortalized cell line, i.e. a cancer cell. The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer including, but not limited to, squamous cell cancers, and cancers of mucinous origins, such as, mucinous ovarian cancer, cholangiocarcinoma (liver) and renal papillary carcinoma. Mucosal distribution, for example as provided by an IgA-based binding molecule as provided herein, could be beneficial for certain cancers, e.g., lung cancer, ovarian cancer, colorectal cancer, or squamous cell carcinoma.

This disclosure further provides a method of preventing or treating a cancer in a subject in need thereof, comprising administering to the subject an effective amount of a dimeric, pentameric, or hexameric TNF superfamily receptor protein binding molecule as provided herein or an antigen-binding fragment thereof, a composition or formulation comprising the binding molecule, or a polynucleotide, a vector, or a host cell as described herein.

Effective doses of compositions for treatment of cancer vary depending upon many different factors, including means of administration, target site, physiological state of the patient, whether the patient is human or an animal, other medications administered, and whether treatment is prophylactic or therapeutic. In certain aspects the treatment methods provided herein can provide increased safety, in that the composition exhibits greater cytotoxicity (e.g., induces apoptosis to a greater extent) on cancer cells than on non-cancer cells, e.g., normal human hepatocytes. Usually, the patient is a human but non-human mammals including transgenic mammals can also be treated. Treatment dosages can be titrated using routine methods known to those of skill in the art to optimize safety and efficacy.

The compositions of the disclosure can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The subject to be treated can be any animal, e.g., mammal, in need of treatment, in certain aspects, subject is a human subject.

In its simplest form, a preparation to be administered to a subject is a dimeric, pentameric, or hexameric binding molecule as provided herein, or an antigen-binding fragment thereof, administered in conventional dosage form, which can be combined with a pharmaceutical excipient, carrier or diluent as described elsewhere herein.

A TNF superfamily receptor protein binding molecule as provided herein or an antigen-binding fragment thereof can be administered by any suitable method as described elsewhere herein, e.g., via IV infusion. In certain aspects, a TNF superfamily receptor protein binding molecule as provided herein or an antigen-binding fragment thereof can be introduced into a tumor, or in the vicinity of a tumor cell.

All types of tumors are potentially amenable to treatment by this approach including, without limitation, carcinoma of the breast, lung, pancreas, ovary, kidney, colon and bladder, as well as melanomas, sarcomas and lymphomas. Mucosal distribution could be beneficial for certain cancers, e.g., lung cancer, ovarian cancer, colorectal cancer, or squamous cell carcinoma.

A dimeric, pentameric, or hexameric binding molecule for use in the methods provided herein, is a binding molecule with two, five, or six "binding units" as defined herein, that can specifically bind to a TNF superfamily receptor protein, e.g., human DR5. In certain aspects, a dimeric, pentameric, or hexameric binding molecule for use in the methods provided herein comprises two, five, or six bivalent binding units, respectively, where each binding unit includes two IgA or IgM heavy chain constant regions or fragments thereof. In certain aspects, the two IgA or IgM heavy chain constant regions are human heavy chain constant regions.

Where the binding molecule for use in the methods provided herein is a dimeric IgA-based binding molecule, the binding molecule can further comprise a J chain, or fragment thereof, or variant thereof, and can further comprise a secretory component, or fragment thereof, or variant thereof.

Where the binding molecule for use in the methods provided herein is pentameric IgM-based binding molecule, the binding molecule can further comprise a J chain, or fragment thereof, or variant thereof.

An IgA heavy chain constant region of a binding molecule for use in the methods provided herein can include one or more of a $C\alpha 1$ domain, a $C\alpha 2$ domain, and/or a $C\alpha 3$ domain, provided that the constant region can serve a desired function in the binding molecule, e.g., associate with a light chain constant region to facilitate formation of a binding domain, or associate with another binding unit to form a dimer. In certain aspects the two IgA heavy chain constant regions or fragments thereof within an individual binding unit each comprise a $C\alpha 3$ domain or fragment thereof, a tailpiece (TP) or fragment thereof, or any combination of a $C\alpha 3$ domain and a TP or fragment thereof. In certain aspects the two IgA heavy chain constant regions or fragments thereof within an individual binding unit each further comprise a $C\alpha 2$ domain or fragment thereof, a $C\alpha 1$ domain or fragment thereof, or a $C\alpha 1$ domain or fragment thereof and a $C\alpha 2$ domain or fragment thereof.

An IgM heavy chain constant region of a binding molecule for use in the methods provided herein can include one or more of a $C\mu 1$ domain, a $C\mu 2$ domain, a $C\mu 3$ domain, and/or a $C\mu 4$ domain, provided that the constant region can serve a desired function in the binding molecule, e.g., associate with a light chain constant region to facilitate formation of a binding domain, or associate with other binding units to form a hexamer or a pentamer. In certain aspects the two IgM heavy chain constant regions or fragments thereof within an individual binding unit each comprise a $C\mu 3$ domain or fragment thereof, a $C\mu 4$ domain or fragment thereof, a tailpiece (TP) or fragment thereof, or any combination of a $C\mu 3$ domain a $C\mu 4$ domain, and a TP or fragment thereof. In certain aspects the two IgM heavy chain constant regions or fragments thereof within an individual binding unit each further comprise a $C\mu 2$ domain or fragment thereof, a $C\mu 1$ domain or fragment thereof, or a $C\mu 1$ domain or fragment thereof and a $C\mu 2$ domain or fragment thereof.

While a variety of different dimeric, pentameric, and hexameric binding molecules for use in the methods provided herein can be contemplated by a person of ordinary skill in the art based on this disclosure, and as such are included in this disclosure, in certain aspects, a binding molecule for use in the methods provided herein is provided in which each binding unit comprises two IgA or IgM heavy chains each comprising a VH situated amino terminal to the IgA or IgM constant region or fragment thereof, and two immunoglobulin light chains each comprising a VL situated amino terminal to an immunoglobulin light chain constant region.

Moreover in certain aspects, at least one binding unit of the binding molecule for use in the methods provided herein, or at least two, at least three, at least four, at least five, or at least six binding units of the binding molecule for use in the methods provided herein, comprises or comprise two of the TNF superfamily receptor protein binding domains as described above. In certain aspects the two TNF superfamily receptor protein binding domains in at least one binding unit of the binding molecule, or at least two, at least three, at least four, at least five, or at least six binding units of the binding molecule for use in the methods provided herein for use in the methods provided herein can be different from each other, or they can be identical.

In certain aspects, the two IgA or IgM heavy chains within at least one binding unit of the binding molecule, or at least two, at least three, at least four, at least five, or at least six binding units of the binding molecule for use in the methods provided herein are identical.

In certain aspects, the two light chains within at least one binding unit of the binding molecule, or at least two, at least three, at least four, at least five, or at least six binding units of the binding molecule for use in the methods provided herein are identical. In certain aspects, two identical light chains within at least one binding unit, or within at least two, at least three, at least four, at least five, or at least six binding units of the binding molecule for use in the methods provided herein are kappa light chains, e.g., human kappa light chains, or lambda light chains, e.g., human lambda light chains.

Dimeric, pentameric, or hexameric TNF receptor binding molecule for use in the methods provided herein can possess advantageous structural or functional properties compared to other binding molecules. For example, a dimeric, pentameric, or hexameric TNF receptor binding molecule for use in the methods provided herein can possess improved activity in a biological assay, either in vitro or in vivo, than a corresponding binding molecule, e.g., Lexatumumab or a variant, analog, or derivative thereof. Biological assays include, but are not limited to ELISA or Western blot caspase assays, and FACS analyses using stains indicative of apoptotic cell death such as annexin-v.

Pharmaceutical Compositions and Administration Methods

Methods of preparing and administering a dimeric, pentameric, or hexameric TNF receptor binding molecule as provided herein to a subject in need thereof are well known to or are readily determined by those skilled in the art in view of this disclosure. The route of administration of a TNF receptor binding molecule can be, for example, oral, parenteral, by inhalation or topical. The term parenteral as used herein includes, e.g., intravenous, intraarterial, intraperitoneal, intramuscular, subcutaneous, rectal, or vaginal administration. While these forms of administration are contemplated as suitable forms, another example of a form for administration would be a solution for injection, in particular for intravenous or intraarterial injection or drip. A suitable pharmaceutical composition can comprise a buffer (e.g. acetate, phosphate or citrate buffer), a surfactant (e.g. polysorbate), optionally a stabilizer agent (e.g. human albumin), etc.

As discussed herein, a dimeric, pentameric, or hexameric TNF receptor binding molecule as provided herein can be administered in a pharmaceutically effective amount for the in vivo treatment of cancers expressing TNF superfamily receptor proteins. In this regard, it will be appreciated that the disclosed binding molecules can be formulated so as to facilitate administration and promote stability of the active agent. Pharmaceutical compositions accordingly can comprise a pharmaceutically acceptable, non-toxic, sterile carrier such as physiological saline, non-toxic buffers, preservatives and the like. A pharmaceutically effective amount of a dimeric, pentameric, or hexameric TNF receptor binding molecule as provided herein means an amount sufficient to achieve effective binding to a target and to achieve a therapeutic benefit. Suitable formulations are described in Remington's Pharmaceutical Sciences (Mack Publishing Co.) 16th ed. (1980).

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a dimeric, pentameric, or hexameric TNF superfamily receptor protein binding molecule that can be combined with carrier materials to produce a single dosage form will vary depending, e.g., upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, a dimeric, pentameric, or hexameric TNF superfamily receptor protein binding molecule as provided herein can be administered to a subject in need of therapy in an amount sufficient to produce a therapeutic effect. A dimeric, pentameric, or hexameric TNF superfamily receptor protein binding molecule as provided herein can be administered to the subject in a conventional dosage form prepared by combining the antibody or antigen-binding fragment, variant, or derivative thereof of the disclosure with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables.

By "therapeutically effective dose or amount" or "effective amount" is intended an amount of a dimeric, pentameric, or hexameric TNF superfamily receptor protein binding molecule, that when administered brings about a positive therapeutic response with respect to treatment of a patient with cancer expressing TNF superfamily receptor protein.

Therapeutically effective doses of the compositions disclosed herein for treatment of cancer can vary depending upon many different factors, including means of administration, target site, physiological state of the patient, whether the patient is human or an animal, other medications administered, and whether treatment is prophylactic or therapeutic. In certain aspects, the subject or patient is a human, but non-human mammals including transgenic mammals can also be treated. Treatment dosages can be titrated using routine methods known to those of skill in the art to optimize safety and efficacy.

The amount of a dimeric, pentameric, or hexameric TNF superfamily receptor protein binding molecule to be administered is readily determined by one of ordinary skill in the art without undue experimentation given this disclosure. Factors influencing the mode of administration and the respective amount of a dimeric, pentameric, or hexameric TNF superfamily receptor protein binding molecule include, but are not limited to, the severity of the disease, the history of the disease, and the age, height, weight, health, and physical condition of the individual undergoing therapy. Similarly, the amount of a dimeric, pentameric, or hexameric TNF receptor binding molecule to be administered will be dependent upon the mode of administration and whether the subject will undergo a single dose or multiple doses of this agent.

This disclosure also provides for the use of a dimeric, pentameric, or hexameric TNF superfamily receptor protein binding molecule in the manufacture of a medicament for treating, preventing, or managing cancer where the cancer expresses TNF superfamily receptor proteins.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., N.Y.).

Standard reference works setting forth general principles of immunology include Current Protocols in Immunology, John Wiley & Sons, New York; Klein (1982) J., Immunology: The Science of Self-Nonself Discrimination (John Wiley & Sons, N.Y.); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: DR5 Expression Profiling

DR5 cell surface expression was quantitated by fluorescence activated cell sorting (FACS) analysis. Briefly, FACS stain buffer (BD Pharmigen Catalog #554656) was used for staining and wash steps. Tumor cells ($1\times10^5$-$5\times10^5$) were stained with 0.25 µg of anti-human DR5-PE (eBioscience Catalog #12-9908-42) or isotype-PE control (eBioscience Catalog #12-4714-42) for 15 minutes at 4° C., protected from light. Cells were washed twice, resuspended in FACS stain buffer, and results were acquired by flow cytometry. FIG. 1A shows the peak shift with the anti-human DR5 antibody (lower panel) as opposed to the isotype control (upper panel). FIG. 1B shows that DR5 expression varies by cell line, with 293F cells expressing the most DR5 among this set of cell lines.

Example 2: Anti-DR5 mAb Specificity

Specificity ELISA

The purpose of this assay is to demonstrate anti-DR5 mAb binding to DR5, but not to DR4 or decoy receptors DcR1 and DcR2. Soluble DR5, DR4, DcR1, or DcR2 protein (R&D Systems Catalog #631-T2-100/CF, 347-DR-100/CF, 630-TR-100/CF, 633-TR-100 respectively) were coated on an ELISA plate at 2 µg/mL in 100 mM NaHCO$_3$ pH 9.5 overnight at 4° C. A solution of 2% BSA in PBS was used for the blocking and antibody incubation steps. The plate was blocked for 1 hour at room temperature, then incubated with mouse anti-human DR5 mAb (Acris Antibodies Catalog #AM31206AF-N) for 1 hour at room temperature. anti-DR5 mAb was 3-fold serially diluted to concentrations ranging from 1 to 200 ng/mL. After washing 3 times with PBS plus 0.05% Tween-20, the plate was incubated with rat anti-mouse kappa-HRP (Southern Biotech Catalog #1180-05) for 1 hour at room temperature, protected from light. After washing 3 times with PBS plus 0.05% Tween-20, the plate was incubated with TMB substrate (BD Biosciences Catalog #555214) for 20 minutes at room temperature. The reaction was stopped with 1M H$_2$SO$_4$ and absorbance at 450 nm was determined using a microtiter plate reader. FIG. 2 shows that the mouse anti-human DR5 mAb bound to DR5, but not to DR4, DcR1 or DcR2.

For Human Anti-DR5 mAb ELISAs, 1:2000 Mouse Anti-Human Lambda-HRP (Southern

Biotech Catalog #9180-05) or 1:6000 Mouse Anti-Human Kappa-HRP (Southern Biotech Catalog #9230-05) was used for detection.

Cell Binding

This example was used to confirm anti-DR5 mAb binding to cells. FACS Stain Buffer (BD Pharmigen Catalog #554656) was used for staining and washing steps. Colo205 cells ($2\times10^5$ cells from ATCC Catalog #CCL-222) were stained with 10 µg/mL of mouse anti-human DR5 mAb (Acris Antibodies Catalog #AM31206AF-N) or an isotype control (Invivogen Catalog #hcd20-mab9) for 15 minutes at 4° C., protected from light. Cells were washed twice, then stained with goat anti-mouse IgG-APC (Jackson ImmunoResearch Catalog #115-136-071) at a final dilution of 1:200 for 15 minutes at 4° C., protected from light. Cells were washed twice, then resuspended in FACS stain buffer, and results were acquired by flow cytometry. Results are provided in FIG. 3, the lower panel showing the peak shift observed for the anti-DR5 mAb.

For Human Anti-DR5 mAb binding, Goat Anti-Human IgG Fc-Alexa 647 (Southern Biotech Catalog #2014-31) or Rabbit Anti-Human IgM-Alexa 647 (Abcam Catalog #ab 150191) was used for detection.

Example 3: Anti-DR5 mAb Functional Activity and Cytotoxicity Assay

This example demonstrates that cross-linking is required to achieve DR5 mAb cytotoxicity. Colo205 cells (ATCC Catalog #CCL-222) were seeded, $1\times10^4$ cells per well, in a 96-well plate and allowed to attach overnight. The next day, cells were treated with serially diluted mouse anti-human DR5 mAb (Acris Antibodies Catalog #AM31206AF-N, R&D Systems Catalog #MAB631, BioLegend Catalog #307402, or Acris Antibodies Catalog # AM31205AF-N) and incubated for 24 hours at 37° C. Colorimetric readout: three hours prior to harvest, CCK-8 cell viability reagent (Dojindo CK04-13) was added at 10 percent of the total reaction volume and the plate was incubated at 37° C. for the remaining 3 hours. Absorbance at 450 nm was evaluated on a plate reader. Results are shown in FIG. 4 (open circles), showing little or no cytotoxicity in the absence of a cross-linker.

The assay was then performed as above, except that after pre-incubation of cells with serially diluted mouse anti-human DR5 mAb for 20 minutes at room temperature, goat anti-mouse IgG1 Fc (Jackson ImmunoResearch Catalog #115-005-205) cross-linking agent was added at 3 fold the concentration of the highest dose of anti-DR5 mAb. Results are provided in FIG. 4 (closed circles), showing 100% cytotoxicity with the cross-linker.

For human anti-DR5 mAb induced cytotoxicity, Anti-Human IgG Fc (Biolegend Catalog #409302) was used as the cross-linking agent. Alternatively, goat anti-human IgG plus IgM (H+L) Fab2 (Jackson ImmunoResearch Catalog #109-006-127) can be used as cross-linking agent.

Luminescent readout: at time of harvest, CELL TITER GLO® viability reagent (Promega G7572) was added at a volume equal to that of the medium in the well. Cells were lysed for 10 min and luminescence was read on a plate reader.

Example 4: Apoptosis Assays

Anti-DR5-induced apoptosis in the presence or absence of cross linker was measured using the following methods. Colo205 cells ($1\times10^5$ cells from ATCC, Catalog #CCL-222) were treated with 5 µg/mL mouse anti-human DR5 mAb (Acris Antibodies Catalog #AM31206AF-N or R&D Systems Catalog #MAB631) or an isotype control (Invivogen Catalog #hcd20-mab9) for up to 4 hours at 37° C. Cells were washed twice with cold PBS, then stained with Annexin V-PE and 7-AAD (1 µL each per sample) in the supplied binding buffer (BD Pharmigen Catalog #559763) for 15 minutes at 4° C., protected from light. Annexin V and 7-AAD were used to measure apoptotic (x-axis) and dead cells (y-axis), respectively, using flow cytometry. Results with untreated cells are shown in the leftmost panel of FIG. 5 (untreated), and results using anti-human DR5 mAb in the absence of cross linker are shown in the second panel from the left in FIG. 5 (Anti-DR5 IgG only). Little or no change in the pattern was observed.

The assay was then performed as above, except that after pre-incubation of cells with serially diluted mouse anti-human DR5 mAb for 20 minutes at room temperature, goat anti-mouse IgG1 Fc (Jackson ImmunoResearch Catalog #115-005-205) cross-linking agent was added at 3 fold increased concentration over of the highest dose of anti-DR5 mAb. The third panel from the left in FIG. 5 shows results from cross-linker only (no apoptosis). The right-most panel of FIG. 5 shows significant annexin V-stained cells, indicating that apoptosis occurred in the presence of the cross-linker (Anti-DR5 IgG+crosslinker).

For human anti-DR5 mAb induced apoptosis, Anti-Human IgG Fc (Biolegend Catalog #409302) was used as the cross-linking agent. Alternatively, goat anti-human IgG plus IgM (H+L) Fab2 (Jackson ImmunoResearch Catalog #109-006-127) can be used as cross-linking agent.

Example 5: Caspase Activation Assay

This example shows anti-DR5 induced apoptosis demonstrated by caspase activation. Colo205 cells (ATCC Catalog #CCL-222) were seeded with $1\times10^4$ cells per well in a 96-well plate and allowed to attach overnight. The next day, cells were treated with 5 µg/mL mouse anti-human DR5 mAb (Acris Antibodies Catalog #AM31206AF-N or R&D Systems Catalog #MAB631) for up to 24 hours at 37° C. At time of harvest, CASPASE GLO® 3/7 reagent (Promega Catalog #G8090) was added at a volume equal to the total media in each well. Reaction was incubated with shaking, for 30 minutes at room temperature and luminescence was evaluated on a plate reader. In the absence of cross-linking little or no caspase activity was observed (FIG. 6, crosshatch bars).

The assay was then performed as above, except that after pre-incubation of cells with serially diluted mouse anti-human DR5 mAb for 20 minutes at room temperature, goat anti-mouse IgG1 Fc (Jackson ImmunoResearch Catalog #115-005-205) cross-linking agent was added at 3 fold over the concentration of anti-DR5 mAb. The results are shown as solid bars in FIG. 6. In the presence of cross linking, significant caspase activity was observed.

For human anti-DR5 mAb induced caspase activation, Anti-Human IgG Fc (Biolegend Catalog #409302) was used as the cross-linking agent. Alternatively, goat anti-human IgG plus IgM (H+L) Fab2 (Jackson ImmunoResearch Catalog #109-006-127) can be used as cross-linking agent.

Example 6: Multimeric Anti-DR5 Antibodies Have Superior Activity

This example shows the superior in vitro activity of multimeric anti-DR5 antibodies. FIG. 7A, is a photograph of a non-reducing SDS-PAGE showing one anti-DR5 mAb that is predominantly multimeric (lane 1, R&D Systems clone 71903), lane 2 corresponds to BioLegend clone DJR2-4, lane 3 corresponds to Acris Antibodies clone B-K29, and lane 4 corresponds to Acris Antibodies clone B-D37.

Anti-DR5 mAb Functional Activity and Cytotoxicity Assay

Using similar methods as in Example 3, it is shown that only the multimeric Anti-DR5 mAb causes Colo205 cytotoxicity in the absence of cross-linker. (See, FIG. 7B; R&D Systems clone 71903, filled squares; BioLegend clone DJR2-4, open circles, dashed line; Acris Antibodies clone B-K29, filled diamonds; Acris Antibodies clone B-D37, open triangles, dashed line).

Apoptosis Assays

Using similar methods as in Example 4, it is shown that in the absence of cross-linker, the multimeric anti-DR5 mAb induces apoptosis in Colo205 cells over time, but not the monomeric anti-DR5 mAb or isotype control. (See, FIG. 7C; 1 hr, 2 hr and 4 hr time points shown).

Caspase Activation Assay

Using methods similar to those provided in Example 5, it is shown that in the absence of crosslinker the multimeric, but not monomeric, anti-DR5 mAb induces caspase activation in Colo205 cells. (See, FIG. 7D).

Example 7: Construction of an IgM Anti-DR5 Antibody

Generation of DNA constructs

The VH and VL sequences according to SEQ ID NO: 1 and SEQ ID NO: 2 (Anti-DR5 mAb #1), the VH and VL sequences according to SEQ ID NO; 5 and SEQ ID NO: 6 (Anti-DR5 mAb #2), the VH and VL sequences according to SEQ ID NO; 84 and SEQ ID NO: 85 (Anti-DR5 mAb #3), and the VH and VL sequences according to SEQ ID NO; 88 and SEQ ID NO: 89 (Anti-DR5 mAb #4) were inserted into Aragen Biosciences and Lake Pharma proprietary IgG and IgM vectors by standard cloning methods.

Transfection

Mammalian cells are co-transfected with equal molar ratios of different expression vectors by standard procedures.

Purification of Human Anti-DR5 IgG

Human anti-DR5 IgG is purified using the MABSELECT SURE™ affinity matrix (GE Life Sciences Catalog #17-5438-01) according to manufacturer's recommendation.

Purification of Human Anti-DR5 IgM.

Human anti-DR5 IgM with or without J chain is purified using the CAPTURESELECT® IgM affinity matrix (BAC, Thermo Fisher Catalog #2890.05) according to manufacturer's recommendation.

Example 8: IgM Anti-DR5 mAb #2 is Specific for DR5

An IgG version and pentameric IgM-J chain version of anti-DR5 mAb #2 were tested for binding specificity by ELISA as described in Example 2. As shown in FIG. 8A (IgG) and FIG. 8B (IgM), the antibodies bound to human DR5 but not human DR4 or either of the decoy receptors DcR1 or DcR2.

IgG and IgM versions of anti-DR5 Mab #1 were tested for binding to the target cell Colo205 by the method described in Example 2. The results are shown in FIG. 9.

Figure 10A:
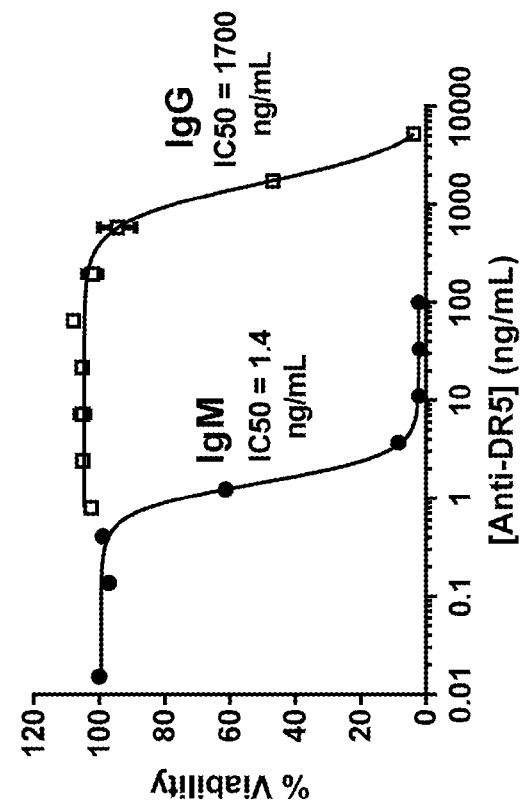
Figure 10B:
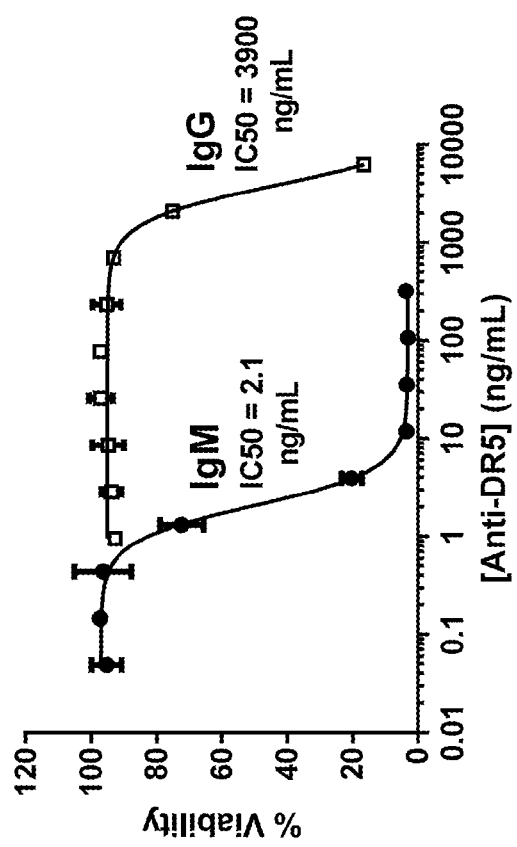
Figure 10C:
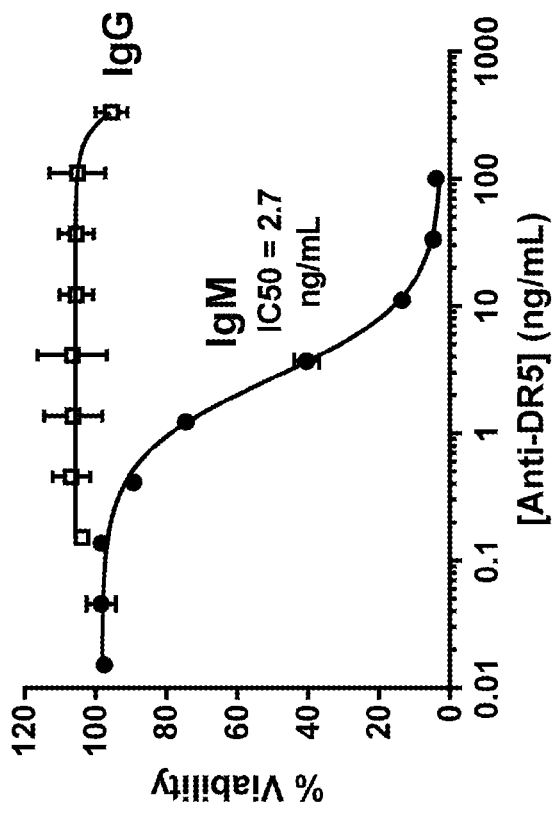
Figure 10D:
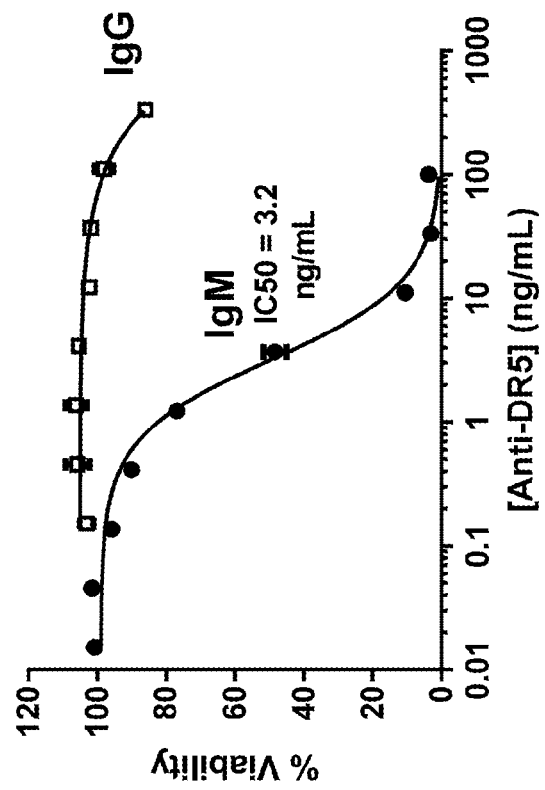
Figure 10E:
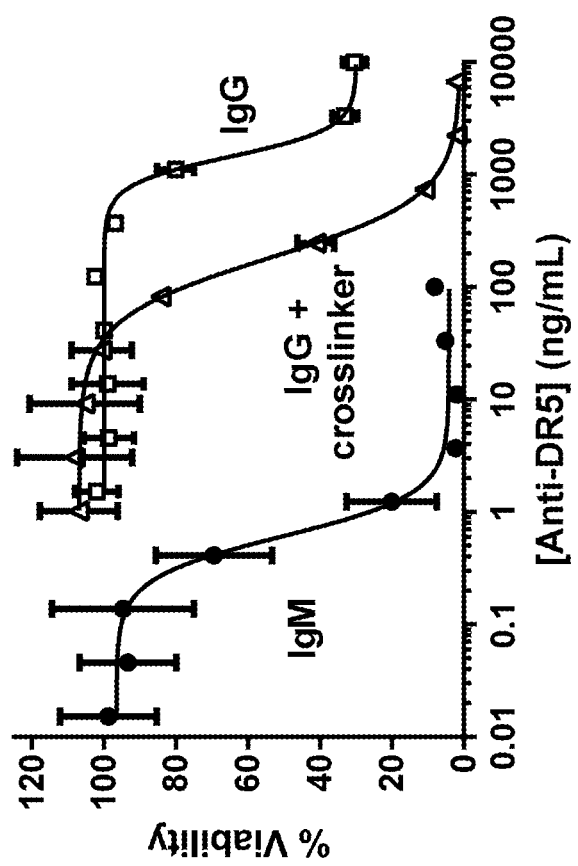
Figure 11A:
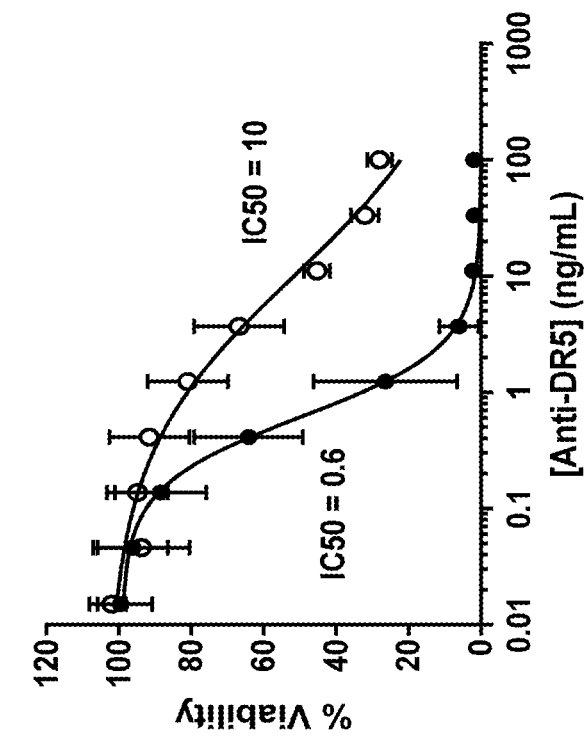
Figure 11B:
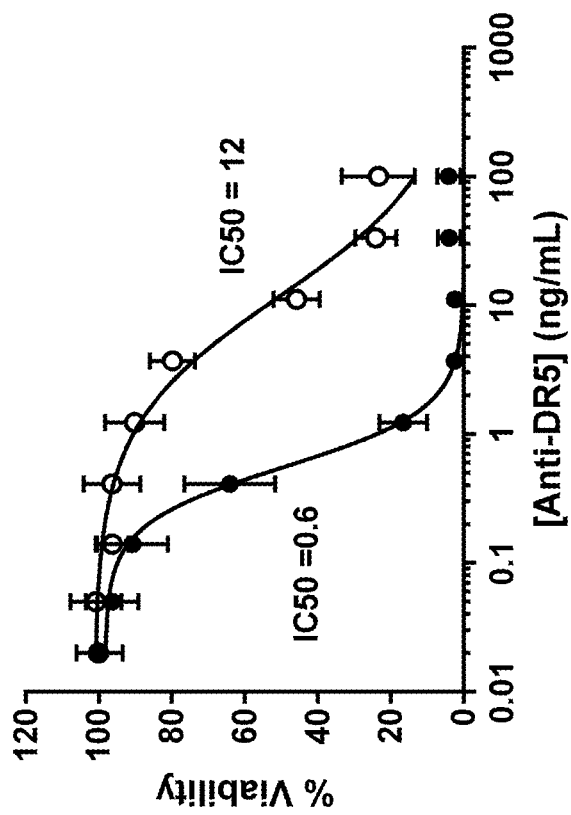
Figure 11D:
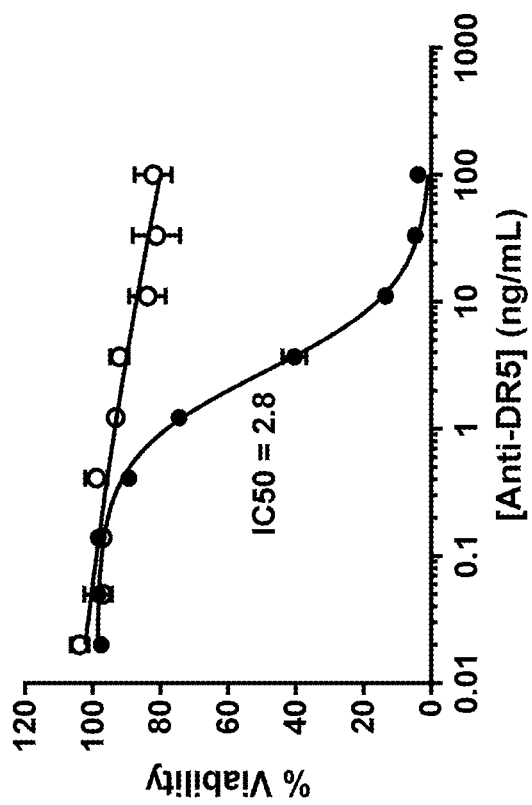
Figure 11C:
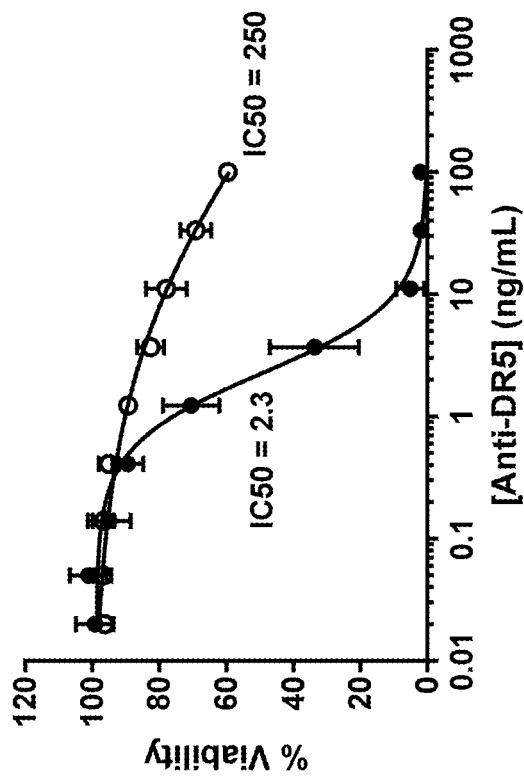

Example 9: IgM Anti-DR5 mAbs are More Cytotoxic than the Corresponding IgG Versions IgG versions and pentameric IgM-J chain versions of anti-DR5 Mabs #1, #2, #3, and #4 were tested for cytotoxicity on Colo205 cells using the bioluminescence assay described in Example 3. As shown in FIG. 10A-FIG. 10D, anti-DR5 IgMs are more cytotoxic than the IgG counterparts. In FIG. 10E, the IgM version of anti-DR5 Mab #1 was compared to the corresponding IgG version with and without a crosslinker. Even with the crosslinker, the IgM version was more cytotoxic.

Hepatotoxicity Assay

Moreover, DR5 mAb IGM superagonists are more cytotoxic on Colo205 tumor cells than on primary human hepatocytes. The Colo205 cytotoxicity assays were carried out using the bioluminescence assay described in Example 3. About $3.5 \times 10^4$ primary human hepatocytes (Bioreclamation Catalog #X008001-P) were seeded in a collagen coated 96-well plate and allowed to attach overnight. The next day, the Colo205 cells and hepatocytes were treated with serially diluted IgM Anti-DR5 mAbs #1-#4, and incubated for 24 hours at 37° C. At time of harvest, CELL TITER GLO® viability reagent (Promega G7572) was added at a volume equal to that of the medium in the well. The cells were lysed for 10 min and luminescence was read on a plate reader. As shown in FIG. 11A-FIG. 11D, the cytotoxicity of the four IgM anti-DR5 mAbs was consistently greater on Colo205 tumor cells (closed circles) than on primary human hepatocytes (open circles).

What is claimed is:

1. An isolated IgM antibody comprising five or six identical bivalent binding units,
   wherein each binding unit comprises two IgM heavy chain constant regions, each associated with an identical antigen-binding domain,
   wherein the IgM heavy chain constant regions each comprise a Cμ1 domain, a Cμ2 domain, a Cμ3 domain, and a Cμ4-tp domain,
   wherein the antigen-binding domains of the antibody specifically and agonistically bind to a tumor necrosis factor (TNF) superfamily receptor protein,
   wherein the antibody can cross-link at least three identical TNF superfamily receptor proteins expressed on the surface of a cell, thereby activating signal transduction in the cell; and
   wherein the antibody can activate TNF superfamily receptor-mediated signal transduction in a TNF receptor superfamily-expressing cell at a higher potency than an equivalent amount of a bivalent IgG antibody or fragment thereof comprising two of the same antigen binding domains, which also specifically binds to and agonizes the same TNF superfamily receptor protein.

2. The antibody of claim 1, wherein the activation of signal transduction can trigger apoptosis, proliferation and/or morphogenesis in the cell in which the receptor protein is expressed.

3. The antibody of claim 2, wherein the signal transduction can trigger apoptosis, and wherein the TNF superfamily receptor protein is TNFR1 (DR1), TNFR2, TNFR1/2, CD40 (p50), Fas (CD95, Apo1, DR2), CD30, 4-1BB (CD137, ILA), TRAILR1 (DR4, Apo2), TRAILR2 (DR5), TRAILR3 (DcR1), TRAILR4 (DcR2), OPG (OCIF), TWEAKR (FN14), LIGHTR (HVEM), DcR3, DR3, EDAR, or XEDAR.

4. The antibody of claim 2, wherein the signal transduction can trigger proliferation, and wherein the TNF superfamily receptor protein is TNFR1/2, GITR (AITR), TACI, BCMA, TWEAKR (FN14), RANK (TRANCER), CD27, CD40 (p50), OX40 (CD134), LT-βR, TNFR1 (DR1), or TNFR2.

5. The antibody of claim 2, wherein the signal transduction can trigger morphogenesis, and wherein the TNF superfamily receptor protein is Fas (CD95, Apo1, DR2), TRAILR1 (DR4, Apo2), DR5 (TRAILR2), TRAILR3 (DcR1), TRAILR4 (DcR2), OPG (OCIF), CD40 (p50), EDAR, XEDAR, or TNFR1/2.

6. The antibody of claim 1, wherein the five or six binding units are human, humanized, or chimeric IgM binding units.

7. The antibody of claim 1, wherein the cell is a cancer cell.

8. The antibody of claim 1, which is pentameric, and further comprises a J chain, or fragment thereof, or variant thereof.

9. The antibody of claim 1, wherein the IgM heavy chain constant regions are human IgM constant regions.

10. The antibody of claim 1, wherein each binding unit comprises two IgM heavy chains each comprising a VH situated amino terminal to the IgM constant region or fragment thereof, and two immunoglobulin light chains each comprising a VL situated amino terminal to an immunoglobulin light chain constant region.

11. A composition comprising the antibody claim 1.

12. The antibody of claim 2, which can trigger apoptosis, morphogenesis, or proliferation of a TNF superfamily receptor protein-expressing cell at higher potency than an equivalent amount of a monospecific, bivalent IgG1 antibody or fragment thereof comprising two of the same antigen binding domains that specifically binds to the same TNF superfamily receptor protein epitope as the TNF superfamily receptor protein binding domain.

13. A method of inducing TNF superfamily receptor-mediated signal transduction in a TNF superfamily receptor-expressing cell, which comprises contacting the TNF superfamily receptor-expressing cell with the antibody of claim 1.

14. The method of claim 13, wherein the antibody triggers apoptosis, morphogenesis, or proliferation of the TNF superfamily receptor protein-expressing cell at higher potency than an equivalent amount of a monospecific, bivalent IgG1 antibody or fragment thereof that specifically binds to the same TNF superfamily receptor protein.

15. A method of treating cancer comprising administering to a subject in need of treatment an effective amount of the antibody of claim 1.

16. The method of claim 15, wherein the subject is human.

* * * * *

SEQUENCE LISTING

```
<160> NUMBER OF SEQ ID NOS: 89

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

-continued

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Ile Leu Gly Ala Gly Arg Gly Trp Tyr Phe Asp Leu Trp Gly
        100                 105                 110

Lys Gly Thr Thr Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
            85                  90                  95

Val Val Phe Gly Gly Gly Thr Lys Leu Thr Val Leu
        100                 105

<210> SEQ ID NO 3
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Gly Ser Thr Gly Tyr Ala Asp Ser Val
50                  55                  60

```
Lys Gly Arg Val Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Glu Leu Thr Gln Asp Pro Ala Val Ser Val Ala Leu Gly Gln Thr
 1               5                  10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Ala Asp Ser Ser Gly Asn His Val
                 85                  90                  95

Val Phe Gly Gly Gly Thr Lys Leu Thr Val Leu
            100                 105

<210> SEQ ID NO 5
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Cys Ile Gly His Ile His Asn Ser Gly Thr Thr Tyr Tyr Asn Pro Ser
 50                  55                  60

Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
                 85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120
```

```
<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys
            100                 105

<210> SEQ ID NO 7
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Asp Ser Met Ile Thr Thr Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 8
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Arg Thr
                85                  90                  95

```
Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Phe
            20                  25                  30

Ser Met Asn Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Leu Ser Met Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Val Arg Ile Asp Tyr Trp Gly Gln Gly Thr Thr Leu Thr Val Ser Ser
            100                 105                 110

<210> SEQ ID NO 10
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Ser
                85                  90                  95

Thr His Val Pro His Thr Phe Gly Gly Gly Thr Lys Leu Glu Ile Lys
                100                 105                 110

Arg

<210> SEQ ID NO 11
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Trp Thr Trp Arg Ile Leu Phe Leu Val Ala Ala Ala Thr Ser
1               5                   10                  15

Ala His Ser Gln Val Gln Leu Val Gln Ser Gly Ala Glu Met Lys Lys
                20                  25                  30

Pro Gly Ala Ser Val Lys Val Ser Cys Lys Thr Ser Gly Tyr Thr Phe
            35                  40                  45

Thr Asn Tyr Lys Ile Asn Trp Val Arg Gln Ala Pro Gly Gln Gly Leu
        50                  55                  60

Glu Trp Met Gly Trp Met Asn Pro Asp Thr Asp Ser Thr Gly Tyr Pro
65                  70                  75                  80

Gln Lys Phe Gln Gly Arg Val Thr Met Thr Arg Asn Thr Ser Ile Ser
                85                  90                  95

Thr Ala Tyr Met Glu Leu Ser Ser Leu Arg Ser Glu Asp Thr Ala Val
                100                 105                 110

Tyr Tyr Cys Ala Arg Ser Tyr Gly Ser Gly Ser Tyr Tyr Arg Asp Tyr
            115                 120                 125

Tyr Tyr Gly Met Asp Val Trp Gly Gln Gly Thr Thr Val Thr Val Ser
        130                 135                 140

Ser
145

<210> SEQ ID NO 12
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser

```
                    85                  90                  95
Ser Leu Glu Pro Glu Asp Phe Ala Val Tyr Tyr Cys Gln Gln Arg Ser
                100                 105                 110

Asn Trp Pro Leu Thr Phe Gly Gly Gly Thr Lys Val Glu Ile Lys Arg
            115                 120                 125
```

<210> SEQ ID NO 13
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Lys His Leu Trp Phe Phe Leu Leu Leu Val Ala Ala Pro Arg Trp
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Ile Gly Tyr Phe Met Asn Trp Met Lys Gln Ser His Gly Lys Ser Leu
    50                  55                  60

Glu Trp Ile Gly Arg Phe Asn Pro Tyr Asn Gly Asp Thr Phe Tyr Asn
65                  70                  75                  80

Gln Lys Phe Lys Gly Lys Ala Thr Leu Thr Val Asp Lys Ser Ser Thr
                85                  90                  95

Thr Ala His Met Glu Leu Leu Ser Leu Thr Ser Glu Asp Ser Ala Val
            100                 105                 110

Tyr Phe Cys Gly Arg Ser Ala Tyr Tyr Phe Asp Ser Gly Gly Tyr Phe
        115                 120                 125

Asp Tyr Trp Gly Gln Gly Thr Thr Leu Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320
```

```
Asn Ser Thr Tyr Arg Val Ser Val Leu Thr Val Leu His Gln Asp
            325                 330                 335

Trp Leu Asn Gly Lys Glu Tyr Lys Cys Lys Val Ser Asn Lys Ala Leu
        340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
        420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 14
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Val Leu Gln Thr Gln Val Phe Ile Ser Leu Leu Leu Trp Ile Ser
1               5                   10                  15

Gly Ala Tyr Gly Asp Val Val Met Thr Gln Thr Pro Leu Ser Leu Pro
            20                  25                  30

Val Ser Leu Gly Asp Gln Ala Ser Ile Ser Cys Arg Ser Ser Gln Ser
        35                  40                  45

Leu Val His Ser Asn Gly Asn Thr Tyr Leu His Trp Tyr Leu Gln Lys
    50                  55                  60

Pro Gly Gln Ser Pro Lys Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Leu Gly Ile Tyr Phe
        100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
        180                 185                 190

Ser Lys Asp Ser Thr Tyr Ser Leu Ser Ser Thr Leu Thr Leu Ser Lys
        195                 200                 205
```

```
Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Phe
            20                  25                  30

Ser Met Asn Trp Val Arg Gln Ala Pro Gly Gln Gly Leu Glu Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ile Asp Tyr Trp Gly Gln Gly Thr Thr Val Thr Val Ser Ser
            100                 105                 110

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Thr His Val Pro His Thr Phe Gly Gln Gly Thr Lys Leu Glu Ile Lys
            100                 105                 110

Arg

<210> SEQ ID NO 17
<211> LENGTH: 470
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

<400> SEQUENCE: 17

```
Met Gly Xaa Leu Gly Leu Ser Trp Val Phe Leu Val Val Ile Leu Glu
1               5                   10                  15

Gly Val Gln Cys Glu Val His Leu Val Glu Ser Gly Gly Gly Leu Val
            20                  25                  30

Arg Pro Gly Gly Ser Leu Lys Leu Ser Cys Ala Ala Ser Gly Phe Ala
        35                  40                  45

Phe Ser Ser Tyr Asp Met Ser Trp Val Arg Gln Thr Pro Glu Lys Arg
    50                  55                  60

Leu Glu Trp Val Ala Tyr Ile Ser Asp Gly Gly Ile Thr Tyr Tyr
65              70                  75                  80

Pro Asp Thr Met Lys Gly Arg Phe Thr Ile Ser Arg Asp Asn Ala Lys
                85                  90                  95

Asn Thr Leu Ser Leu Gln Met Ser Ser Leu Lys Ser Glu Asp Thr Ala
            100                 105                 110

Met Tyr Tyr Cys Ala Arg His Ile Thr Met Val Val Gly Pro Phe Ala
        115                 120                 125

Tyr Trp Gly Gln Gly Thr Leu Val Thr Val Ser Ala Ala Ser Thr Lys
    130                 135                 140

Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
```

```
                370                 375                 380
Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Met Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly Lys
465                 470

<210> SEQ ID NO 18
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Arg Leu Pro Ala Gln Leu Leu Gly Leu Leu Met Leu Trp Val Ser
1               5                   10                  15

Gly Ser Ser Gly Asp Ile Gln Met Thr Gln Ser Ser Ser Ser Phe Ser
                20                  25                  30

Val Ser Leu Gly Asp Arg Val Thr Ile Thr Cys Lys Ala Ser Glu Asp
                35                  40                  45

Ile Tyr Asn Arg Leu Ala Trp Tyr Gln Gln Lys Pro Gly Asn Ala Pro
50                  55                  60

Arg Leu Leu Ile Ser Gly Ala Thr Ser Leu Glu Thr Gly Val Pro Ser
65                  70                  75                  80

Arg Phe Ser Gly Ser Gly Ser Gly Lys Asp Tyr Thr Leu Ser Ile Thr
                85                  90                  95

Ser Leu Gln Thr Glu Asp Val Ala Thr Tyr Tyr Cys Gln Gln Tyr Trp
                100                 105                 110

Ser Thr Pro Leu Thr Phe Gly Ala Gly Thr Lys Leu Glu Leu Lys Arg
                115                 120                 125

Ala Val Ala Ala Pro Ser Val Asp Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
                210                 215                 220

Val Thr Lys Ser Phe Asn Arg Gly Glu Cys
225                 230

<210> SEQ ID NO 19
<211> LENGTH: 466
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Met Glu Leu Gly Leu Ser Trp Val Phe Leu Val Ala Ile Leu Glu Gly
1               5                   10                  15

Val Gln Cys Glu Val Gln Leu Gln Gln Ser Gly Pro Glu Leu Val Lys
            20                  25                  30

Pro Gly Ala Ser Val Arg Met Ser Cys Lys Ala Ser Gly Tyr Thr Phe
        35                  40                  45

Thr Ser Tyr Phe Ile His Trp Val Lys Gln Arg Pro Gly Gln Gly Leu
    50                  55                  60

Glu Trp Ile Gly Trp Ile Tyr Pro Gly Asn Val Asn Thr Lys Tyr Ser
65                  70                  75                  80

Glu Lys Phe Lys Gly Lys Ala Thr Leu Thr Ala Asp Lys Ser Ser Ser
                85                  90                  95

Thr Ala Tyr Met Gln Phe Ser Ser Leu Thr Ser Glu Asp Ser Ala Val
            100                 105                 110

Tyr Phe Cys Ala Arg Gly Glu Ala Gly Tyr Phe Asp Tyr Trp Gly Gln
        115                 120                 125

Gly Thr Thr Leu Thr Val Ser Ser Ala Ser Thr Lys Gly Pro Ser Val
130                 135                 140

Phe Pro Leu Ala Pro Cys Ser Arg Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
370                 375                 380

```
Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Met Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 20
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Arg Leu Pro Ala Gln Leu Leu Gly Leu Leu Met Leu Trp Val Ser
1               5                   10                  15

Gly Ser Ser Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Arg Leu Leu Ile Tyr Trp Ala Ser Thr Arg His Thr Gly Val Pro Asp
65                  70                  75                  80

Arg Phe Thr Gly Ser Gly Ser Gly Thr Asp Tyr Thr Leu Thr Ile Ser
                85                  90                  95

Ser Val Gln Ala Glu Asp Gln Ala Leu Tyr Tyr Cys Gln Gln His Tyr
            100                 105                 110

Arg Thr Pro Trp Thr Phe Gly Gly Gly Thr Lys Leu Glu Ile Lys Arg
        115                 120                 125

Ala Val Ala Ala Pro Ser Val Asp Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 21
<211> LENGTH: 121
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Asp Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asn His Tyr Gly Ser Gly Ser His Phe Asp Tyr Trp Gly
            100                 105                 110

Gln Gly Thr Leu Val Thr Val Ser Ser
        115                 120

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Ser Tyr Lys Thr Pro Leu
                85                  90                  95

Thr Phe Gly Gly Gly Thr Lys Val Glu Ile Lys
            100                 105

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

```
Gly His Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Asp Ser Ser Gly Trp Gly Phe Asp Tyr Trp Gly Gln
            100                 105                 110

Gly Ile Leu Val Thr Val Ser Ser
            115                 120

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Leu Arg Asn Asp
            20                  25                  30

Leu Gly Trp Phe Gln Lys Pro Gly Lys Val Thr Lys Arg Leu Ile
            35                  40                  45

Tyr Ala Ala Ser Ser Leu Gln Arg Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Tyr Ser Phe Pro Trp
                85                  90                  95

Thr Phe Gly Gln Gly Thr Lys Val Glu Ile Lys
            100                 105

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
            35                  40                  45

Trp Ile Gly Tyr Ile Tyr Tyr Ser Gly Ser Ala Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95
```

```
Cys Ala Arg Asp Asp Ser Ser Gly Trp Gly Phe Asp Tyr Trp Gly Gln
                100                 105                 110

Gly Ile Leu Val Thr Val Ser Ser
        115                 120

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Leu Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Arg Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Thr Thr Tyr Phe Cys Leu Gln His Asn Ser Phe Pro Trp
                85                  90                  95

Thr Phe Gly Gln Gly Thr Lys Val Glu Ile Lys
            100                 105

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile Tyr Tyr Ser Gly Ser Ala Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Asp Ser Ser Gly Trp Gly Phe Asp Tyr Trp Gly Gln
                100                 105                 110

Gly Ile Leu Val Thr Val Ser Ser
        115                 120

<210> SEQ ID NO 28
<211> LENGTH: 107
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Leu Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Phe Cys Leu Gln His Asn Ser Phe Pro Trp
                85                  90                  95

Thr Phe Gly Gln Gly Thr Lys Val Glu Ile Lys
            100                 105

<210> SEQ ID NO 29
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
        35                  40                  45

Ser His Ile Ser Ser Ser Gly Ser Ile Leu Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Gly Ala Ala Ala Gly Thr Asp Ala Phe Asp Leu Trp Gly
            100                 105                 110

Gln Gly Thr Met Val Thr Val Ser Ser
        115                 120

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Leu Ser Ala Ser Val Gly
1               5                   10                  15

Asp Arg Val Thr Ile Thr Cys Arg Ser Ser Gln Ser Ile Ser Asn Tyr
            20                  25                  30
```

Ile Asn Trp Tyr Gln Gln Arg Pro Gly Lys Ala Pro Asn Leu Leu Ile
             35                   40                  45

His Asp Val Ser Ser Phe Gln Ser Ala Val Pro Ser Arg Phe Ser Arg
 50                      55                  60

Ser Gly Ser Gly Thr Val Phe Thr Leu Thr Ile Ser Ser Leu Gln Pro
 65                  70                  75                  80

Glu Asp Phe Ala Thr Tyr Phe Cys Gln Gln Thr Tyr Ile Thr Pro Phe
                 85                  90                  95

Thr Phe Gly Pro Gly Thr Lys Val Asp Ile Lys
            100                 105

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Tyr Tyr
             20                  25                  30

Gly Ile His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Tyr Ser Ser Ser Trp Trp Tyr Phe Asp Leu Trp
            100                 105                 110

Gly Arg Gly Thr Leu Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Ser Asn Tyr
             20                  25                  30

Leu Ala Trp Tyr Gln Gln Lys Pro Gly Lys Val Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Leu
                 85                  90                  95

Thr Phe Gly Gly Gly Thr Lys Val Glu Ile Lys
            100                 105

<210> SEQ ID NO 33
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Ala Glu Gln Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Thr Ala Asp Thr Ala Val Tyr Tyr Cys Ala
                85                  90                  95

Arg Asp Ser Pro Arg Gly Phe Ser Gly Tyr Glu Ala Phe Asp Ser Trp
            100                 105                 110

Gly Gln Gly Thr Leu Val Thr Val Ser Ser
        115                 120

<210> SEQ ID NO 34
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Lys Ile Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Leu Ala Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
            100                 105                 110

Lys

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Asn Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Asn Trp Asn Phe Leu Phe Asp Ile Trp Gly Gln
            100                 105                 110

Gly Thr Met Val Thr Val Ser Ser
        115                 120

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Glu Val Glu Ile Lys
            100                 105                 110

<210> SEQ ID NO 37
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Ser Gly Ser Thr Ile Tyr Tyr Ala Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Ser Leu Gly Gly Met Asp Val Trp Gly Gln Gly Thr Thr Val
            100                 105                 110

Thr Val Ser Ser
        115

<210> SEQ ID NO 38
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Val Met Thr Gln Phe Pro Asp Ser Leu Ala Val Ser Leu Gly
 1               5                  10                  15

Glu Arg Ala Thr Ile Asn Cys Lys Ser Ser Gln Ser Val Leu His Ser
                20                  25                  30

Ser Asn Asn Lys Asn Tyr Leu Thr Trp Tyr Gln Leu Lys Pro Gly Gln
                35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                85                  90                  95

Tyr Tyr Ser Thr Pro Ser Ser Phe Gly Gln Gly Thr Lys Leu Glu Ile
            100                 105                 110

Lys

<210> SEQ ID NO 39
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Asn Asn Tyr
                20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

```
Ala Arg Asp Arg Thr Val Tyr Ser Asn Ser Ser Pro Phe Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Ser Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 41
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Val Tyr Ser Ser Ser Pro Phe Tyr Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 42
```

<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Ser Ala Thr Ser Ser Phe Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ala Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

Gln Val Gln Leu Gln Gln Trp Gly Ala Arg Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Gly Gly Ser Ser Gly Tyr Trp Tyr Phe Asp Leu Trp Gly Arg Gly
            100                 105                 110

Thr Leu Val Thr Val Ser Ser
        115

<210> SEQ ID NO 44
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu His Ser
            20                  25                  30

Ser Asn Asn Lys Asn Tyr Leu Val Trp Tyr Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 45
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Val Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Gly Asp Trp Phe Pro Trp Gly
            100                 105                 110

Gln Gly Thr Leu Val Thr Val Ser Ser
        115                 120

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Val Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                    65                  70                  75                  80
Glu Asp Phe Ala Thr Tyr Tyr Cys Gln Gln Ala Asn Ser Phe Pro Phe
                        85                  90                  95

Thr Phe Gly Gly Gly Thr Lys Val Glu Ile Lys
                100                 105
```

```
<210> SEQ ID NO 47
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Leu Val Glu Ser Gly Gly Gly Val Val Gln Pro Gly Arg Ser Leu
1               5                   10                  15

Arg Leu Ser Cys Ala Ala Ser Gly Phe Thr Phe Ser Ser Tyr Gly Met
            20                  25                  30

His Trp Val Arg Gln Ala Pro Gly Lys Gly Leu Glu Trp Val Ala Val
        35                  40                  45

Ile Trp Tyr Asp Gly Arg Asn Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Glu Val Gly Tyr Cys Thr Asn Gly Val Cys Ser Tyr Tyr Tyr Tyr Gly
            100                 105                 110

Met Asp Val Trp Gly Gln Gly Thr Thr Val Thr Val Ser Ser
        115                 120                 125
```

```
<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
                100                 105
```

```
<210> SEQ ID NO 49
<211> LENGTH: 122
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Glu Ser Gly Pro Gly Leu Val Lys Pro Ser Gln
1               5                   10                  15

Thr Leu Ser Leu Thr Cys Ser Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Cys Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Asn Gly Ser Gly Ser Tyr Asp Trp Phe Asp Pro Trp
            100                 105                 110

Gly Gln Gly Ile Leu Val Thr Val Ser Ser
        115                 120

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Phe Leu Ile
        35                  40                  45

Phe Val Ala Ser Ser Phe Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 51
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Met Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

```
Asp Tyr Tyr Trp Ser Trp Ile Arg Gln His Pro Gly Lys Asn Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Asn Gly Ser Gly Ser Tyr Asp Trp Phe Asp Pro Trp
            100                 105                 110

Gly Gln Gly Thr Leu Val Thr Val Ser Ser
            115                 120
```

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Phe Leu Ile
            35                  40                  45

Phe Val Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
            85                  90                  95

Thr Phe Gly Gln Gly Thr Lys Val Glu Ile Lys
            100                 105
```

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Thr Ile His Trp Val Lys Gln Arg Ser Gly Gln Gly Leu Glu Trp Ile
            35                  40                  45

Gly Trp Phe Tyr Pro Gly Gly Gly Tyr Ile Lys Tyr Asn Glu Lys Phe
 50                  55                  60

Lys Asp Arg Ala Thr Leu Thr Ala Asp Lys Ser Ser Asn Thr Val Tyr
65                  70                  75                  80

Met Glu Leu Ser Arg Leu Thr Ser Glu Gly Ser Ala Val Tyr Phe Cys
            85                  90                  95
```

Ala Arg His Glu Glu Gly Ile Tyr Phe Asp Tyr Trp Gly Gln Gly Thr
            100                 105                 110

Thr Leu Thr Val Ser Ser
        115

<210> SEQ ID NO 54
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Ala Met Thr Gln Ser His Lys Phe Met Ser Thr Leu Val Gly
1               5                   10                  15

Asp Arg Val Ser Ile Thr Cys Lys Ala Ser Gln Asp Val Asn Thr Ala
            20                  25                  30

Ile Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Met Glu Ala
65                  70                  75                  80

Glu Asp Ala Ala Thr Tyr Tyr Cys Gln Gln Trp Ser Ser Asn Pro Leu
                85                  90                  95

Thr Phe Gly Ala Gly Thr Lys Leu Glu Leu Lys Arg Ala
            100                 105

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Thr Ile His Trp Val Lys Gln Arg Ser Gly Gln Gly Leu Glu Trp Ile
        35                  40                  45

Gly Trp Phe Tyr Pro Gly Gly Gly Tyr Ile Lys Tyr Asn Glu Lys Phe
50                  55                  60

Lys Asp Arg Ala Thr Leu Thr Ala Asp Lys Ser Ser Asn Thr Val Tyr
65                  70                  75                  80

Met Glu Leu Ser Arg Leu Thr Ser Glu Asp Ser Ala Val Tyr Phe Cys
                85                  90                  95

Ala Arg His Glu Glu Gly Ile Tyr Phe Asp Tyr Trp Gly Gln Gly Thr
            100                 105                 110

Thr Leu Thr Val Ser Ser
        115

<210> SEQ ID NO 56
<211> LENGTH: 104
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 56

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Ile Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Phe
                85                  90                  95

Thr Phe Gly Ser Gly Thr Lys Leu
            100

<210> SEQ ID NO 57
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ser Gly Gly Gly Gly Ser Gly Gly
        115                 120                 125

Gly Gly Ser Gly Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220
```

Arg Asp Ser Ser Gly Asn His Val Val Phe Gly Gly Thr Lys Leu
225                 230                 235                 240

Thr Val Leu Gly

<210> SEQ ID NO 58
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Arg Gly Gly Tyr Ser Ser Arg Ser Ala Ala Tyr Asp Ile Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Ser Glu Leu Thr Gln Asp Pro
    130                 135                 140

Ala Val Ser Val Ala Leu Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Gly Asn Thr Ala Ser Leu
        195                 200                 205

Thr Ile Thr Gly Ala Gln Ala Glu Asp Glu Ala Asp Tyr Tyr Cys Asn
    210                 215                 220

Ser Arg Asp Ser Ser Gly Asn His Val Val Phe Gly Gly Thr Lys
225                 230                 235                 240

Leu Thr Val Leu Gly
                245

<210> SEQ ID NO 59
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Glu Val Lys Lys Pro Gly Ala
1               5                   10                  15

-continued

Ser Val Lys Ile Ser Cys Glu Gly Ser Gly Tyr Thr Phe Asn Ser Tyr
            20                  25                  30

Thr Leu His Trp Leu Arg Gln Ala Pro Gly Gln Arg Leu Glu Trp Met
        35                  40                  45

Gly Arg Ile Asn Ala Gly Asn Gly Asn Thr Lys Tyr Ser Gln Asn Phe
    50                  55                  60

Gln Gly Arg Leu Ser Ile Thr Arg Asp Thr Ser Ala Thr Thr Ala Tyr
65                  70                  75                  80

Met Glu Leu Ser Ser Leu Arg Ser Glu Asp Thr Gly Val Tyr Tyr Cys
                85                  90                  95

Ala Arg Val Phe Thr Tyr Ser Phe Gly Met Asp Val Trp Gly Arg Gly
            100                 105                 110

Thr Leu Val Thr Val Ser Ser Gly Gly Gly Ser Gly Gly Gly Gly
        115                 120                 125

Ser Gly Gly Gly Gly Ser Ala Gln Ser Val Leu Thr Gln Pro Pro Ser
    130                 135                 140

Ala Ser Gly Thr Pro Gly Gln Arg Val Thr Ile Ser Cys Ser Gly Gly
145                 150                 155                 160

Gly Ser Asn Ile Gly Arg Asn Ser Val Ser Trp Tyr Gln Gln Leu Pro
                165                 170                 175

Gly Thr Ala Pro Lys Leu Ile Leu Tyr Ser Asn Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Leu Tyr Tyr Cys
    210                 215                 220

Ala Ala Trp Asp Asp Ser Leu Ser Gly Val Phe Gly Gly Gly Thr
225                 230                 235                 240

Lys Leu Thr Val Leu Gly
                245

<210> SEQ ID NO 60
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val His Arg Pro Gly Arg Ser Gly Tyr Phe Asp Tyr Trp Gly
            100                 105                 110

Arg Gly Thr Leu Val Thr Val Ser Ser Gly Gly Gly Gly Ser Gly Gly
        115                 120                 125

```
Gly Gly Ser Gly Gly Gly Ser Ser Glu Leu Thr Gln Asp Pro Ala
        130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
                180                 185                 190

Pro Asp Arg Phe Ser Gly Ser Ser Gly Asn Thr Ala Ser Leu Thr
                195                 200                 205

Ile Thr Gly Ala Gln Ala Glu Asp Glu Ala Asp Tyr Tyr Cys Asn Ser
        210                 215                 220

Arg Asp Ser Ser Gly Asn His Val Val Phe Gly Gly Gly Thr Lys Leu
225                 230                 235                 240

Thr Val Leu Gly

<210> SEQ ID NO 61
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Ser Gly Ala Glu Val Lys Lys Pro Gly Ala
1               5                   10                  15

Ser Val Arg Val Ser Cys Gln Ala Ser Gly Tyr Ser Leu Ser Glu Tyr
                20                  25                  30

Tyr Ile His Trp Val Arg Gln Ala Pro Gly Gln Gly Leu Glu Trp Met
            35                  40                  45

Gly Trp Leu Asn Pro Asn Ser Gly Val Thr Asp Tyr Ala Gln Lys Phe
        50                  55                  60

Gln Gly Arg Val Ser Met Thr Arg Asp Thr Ser Ile Ser Thr Ala Tyr
65                  70                  75                  80

Met Glu Leu Ser Ser Leu Thr Phe Asn Asp Thr Ala Val Tyr Phe Cys
                85                  90                  95

Ala Arg Gly Asn Gly Asp Tyr Trp Gly Lys Gly Thr Leu Val Thr Val
                100                 105                 110

Ser Pro Gly Gly Gly Gly Ser Gly Gly Gly Gly Ser Gly Gly Gly Gly
            115                 120                 125

Ser Ser Glu Leu Thr Gln Asp Pro Ala Val Ser Val Ala Leu Gly Gln
        130                 135                 140

Thr Val Arg Ile Thr Cys Gln Gly Asp Ser Leu Arg Ser Tyr Tyr Thr
145                 150                 155                 160

Asn Trp Phe Gln Gln Lys Pro Gly Gln Ala Pro Leu Leu Val Val Tyr
                165                 170                 175

Ala Lys Asn Lys Arg Pro Ser Gly Ile Pro Asp Arg Phe Ser Gly Ser
                180                 185                 190

Ser Ser Gly Asn Thr Ala Ser Leu Thr Ile Thr Gly Ala Gln Ala Glu
            195                 200                 205

Asp Glu Ala Asp Tyr Tyr Cys His Ser Arg Asp Ser Ser Gly Trp Val
        210                 215                 220

Phe Gly Gly Gly Thr Lys Leu Thr Val Leu Gly
225                 230                 235
```

<210> SEQ ID NO 62
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Pro Asp
            20                  25                  30

Ala Met His Trp Val Arg Gln Ala Pro Gly Lys Gly Leu Glu Trp Met
        35                  40                  45

Gly Val Ile Ser Phe Asp Gly Ser Gln Thr Phe Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Ala Pro Ala Arg Phe Phe Pro Leu His Phe Asp Ile Trp Gly
            100                 105                 110

Arg Gly Thr Met Val Thr Val Ser Gly Gly Gly Ser Gly Gly
        115                 120                 125

Gly Gly Ser Gly Gly Gly Ser Ala Leu Ser Ser Glu Leu Thr Gln
    130                 135                 140

Asp Pro Ala Val Ser Val Ala Leu Gly Gln Thr Val Arg Ile Thr Cys
145                 150                 155                 160

Gln Gly Asp Ser Leu Arg Thr His Tyr Ala Ser Trp Tyr His Gln Arg
                165                 170                 175

Pro Gly Arg Ala Pro Val Leu Val Asn Tyr Pro Lys Ser Arg Pro
            180                 185                 190

Ser Gly Ile Pro Asp Arg Phe Ser Gly Ser Ser Gly Asn Thr Ala
        195                 200                 205

Ser Leu Thr Ile Ile Gly Ala Gln Ala Ala Asp Glu Gly Asp Tyr Tyr
    210                 215                 220

Cys Gln Ser Arg Asp Ser Ser Gly Val Leu Phe Gly Gly Gly Thr Lys
225                 230                 235                 240

Val Thr Val Leu Gly
                245

<210> SEQ ID NO 63
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

```
Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Phe Ser Gly Tyr Gly Asp Tyr Leu Asp Tyr Trp Gly Lys
                100                 105                 110

Gly Thr Leu Val Thr Val Ser Gly Gly Gly Gly Ser Gly Gly Gly
            115                 120                 125

Gly Ser Gly Gly Gly Ser Ala Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Ile Gly Asn Tyr Asn Tyr Val Ser Trp Tyr Gln Gln
                165                 170                 175

His Pro Gly Lys Ala Pro Lys Leu Met Ile Tyr Glu Val Asn Glu Arg
                180                 185                 190

Pro Ser Gly Val Pro Asp Arg Phe Ser Gly Ser Lys Ser Gly Asn Thr
                195                 200                 205

Ala Ser Leu Thr Val Ser Gly Leu Arg Pro Glu Asp Glu Ala Asp Tyr
210                 215                 220

Tyr Cys Ser Ser Tyr Ala Gly Asn Asn Ala Val Ile Phe Gly Gly Gly
225                 230                 235                 240

Thr Gln Leu Thr Val Leu Gly
                245

<210> SEQ ID NO 64
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr His
                20                  25                  30

Ala Met His Trp Val Arg Gln Ala Pro Gly Gln Ser Leu Glu Trp Met
            35                  40                  45

Gly Trp Ile Asn Thr Gly Asn Gly Asn Thr Lys Tyr Ser Gln Ser Phe
        50                  55                  60

Gln Gly Arg Val Ser Ile Thr Arg Asp Thr Ser Ala Asn Thr Ala Tyr
65                  70                  75                  80

Met Glu Leu Ser Ser Leu Lys Ser Glu Asp Thr Ala Met Tyr Tyr Cys
                85                  90                  95

Ala Arg Ala Ser Arg Asp Ser Ser Gly Tyr Tyr Tyr Val Pro Pro Gly
                100                 105                 110

Asp Phe Phe Asp Ile Trp Gly Gln Gly Thr Leu Val Thr Val Ser Ser
            115                 120                 125

Gly Gly Gly Gly Ser Gly Gly Gly Ser Gly Gly Gly Ser Ala
        130                 135                 140

Gln Ser Ala Leu Thr Gln Pro Ala Ser Val Ser Gly Ser Pro Gly Gln
```

```
                145                 150                 155                 160
Ser Ile Thr Ile Ser Cys Thr Gly Ser Arg Ser Asp Ile Gly Gly Tyr
                165                 170                 175

Asn Phe Val Ser Trp Tyr Gln Gln His Pro Gly Lys Ala Pro Lys Leu
                180                 185                 190

Leu Ile Tyr Asp Val Tyr Asn Arg Pro Ser Gly Ile Ser Asp His Phe
                195                 200                 205

Ser Gly Ser Lys Ser Asp Asn Thr Ala Ser Leu Thr Ile Ser Gly Leu
                210                 215                 220

Gln Ser Glu Asp Asp Ala Asp Tyr Tyr Cys Ser Ser Tyr Ala Gly Tyr
225                 230                 235                 240

His Thr Trp Ile Phe Gly Gly Thr Lys Val Thr Val Leu Gly
                245                 250                 255

<210> SEQ ID NO 65
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Leu Val Asn Tyr
                20                  25                  30

Phe Met His Trp Val Arg Gln Ala Pro Gly Gln Gly Pro Glu Trp Met
                35                  40                  45

Gly Met Ile Asn Pro Ser Gly Gly Thr Thr Lys Asn Arg Gln Lys Phe
            50                  55                  60

Gln Asp Arg Val Thr Met Thr Arg Asp Thr Ser Thr Arg Thr Val Tyr
65                  70                  75                  80

Met Glu Leu Ser Gly Leu Thr Ser Glu Asp Thr Ala Val Tyr Tyr Cys
                85                  90                  95

Ala Thr Asp Phe Lys Gly Thr Asp Ile Leu Phe Arg Asp Trp Gly Arg
                100                 105                 110

Gly Thr Leu Val Thr Val Ser Ser Gly Gly Gly Gly Ser Gly Gly Gly
                115                 120                 125

Gly Ser Gly Gly Gly Gly Ser Ala Gln Ser Val Leu Thr Gln Pro Pro
            130                 135                 140

Ser Ala Ser Gly Thr Pro Gly Gln Arg Val Ser Ile Ser Cys Ser Gly
145                 150                 155                 160

Ser Ser Ser Asn Ile Gly Ser Asn Thr Val Ile Trp Tyr Gln Gln Leu
                165                 170                 175

Pro Gly Thr Ala Pro Lys Leu Leu Met Tyr Ser Asn Asp Arg Arg Pro
                180                 185                 190

Ser Gly Val Pro Asp Arg Phe Ser Gly Ser Lys Ser Gly Thr Ser Ala
                195                 200                 205

Ser Leu Ala Ile Ser Gly Leu Gln Ser Glu Asp Glu Ala Asp Tyr Tyr
                210                 215                 220

Cys Ala Thr Trp Asp Asp Ser Leu Asn Gly His Tyr Val Phe Gly Thr
225                 230                 235                 240

Gly Thr Lys Leu Thr Val Leu Gly
                245
```

```
<210> SEQ ID NO 66
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Met Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Thr Phe Asp Ile Trp Gly Arg Gly Thr Met Val
            100                 105                 110

Thr Val Ser Ser Gly Gly Gly Gly Ser Gly Gly Gly Gly Ser Gly Gly
        115                 120                 125

Gly Gly Ser Ala Gln Pro Val Leu Thr Gln Pro Ser Ala Ser Gly
    130                 135                 140

Thr Pro Gly Gln Arg Val Thr Ile Ser Cys Ser Gly Ser Asn Ser Asn
145                 150                 155                 160

Ile Gly Ser Arg Pro Val Asn Trp Tyr Gln Gln Leu Pro Gly Thr Ala
                165                 170                 175

Pro Lys Leu Leu Ile Gln Gly Asn Asn Gln Arg Pro Ser Gly Val Pro
            180                 185                 190

Asp Arg Phe Ser Gly Ser Lys Ser Gly Thr Ser Ala Ser Leu Ala Ile
        195                 200                 205

Ser Gly Leu Gln Ser Glu Asp Glu Ala Asp Tyr Tyr Cys Ala Ala Trp
    210                 215                 220

Asp Asp Ser Leu Thr Gly Tyr Val Phe Gly Pro Gly Thr Lys Leu Thr
225                 230                 235                 240

Val Leu Gly

<210> SEQ ID NO 67
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Met Gln Leu Val Gln Ser Gly Gly Ala Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Leu Arg Gly Leu Asp Pro Trp Gly Gln Gly Thr Met
            100                 105                 110

Val Thr Val Ser Ser Gly Gly Gly Ser Gly Gly Gly Ser Gly
        115                 120                 125

Gly Gly Gly Ser Ser Glu Leu Thr Gln Asp Pro Ala Val Ser Val Ala
        130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Val Leu
                165                 170                 175

Val Ile Tyr Gly Lys Asn Asn Arg Pro Ser Gly Ile Pro Asp Arg Phe
            180                 185                 190

Ser Gly Ser Ser Ser Gly Asn Thr Ala Ser Leu Thr Ile Thr Gly Ala
            195                 200                 205

Gln Ala Glu Asp Glu Ala Asp Tyr Tyr Cys Asn Ser Arg Asp Ser Ser
        210                 215                 220

Gly Asn His Val Val Phe Gly Gly Gly Thr Lys Leu Thr Val Leu Gly
225                 230                 235                 240

<210> SEQ ID NO 68
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Gly Ala Ser Gly Pro Asp Tyr Trp Gly Arg Gly Thr Met Val
            100                 105                 110

Thr Val Ser Ser Gly Gly Gly Gly Ser Gly Gly Gly Ser Gly Gly
        115                 120                 125

Gly Gly Ser Ala Gln Ser Val Leu Thr Gln Pro Pro Ser Val Ser Ala
        130                 135                 140

Ala Pro Gly Gln Lys Val Thr Ile Ser Cys Ser Gly Ser Thr Ser Asn
145                 150                 155                 160

Ile Gly Asn Asn Tyr Val Ser Trp Tyr Gln Gln Val Pro Gly Thr Ala
                165                 170                 175

```
Pro Lys Leu Leu Ile Tyr Asp Asn Asn Lys Arg Pro Ser Gly Ile Pro
            180                 185                 190

Asp Arg Phe Ser Gly Ser Lys Ser Gly Thr Ser Ala Thr Leu Gly Ile
        195                 200                 205

Thr Gly Leu Gln Thr Gly Asp Glu Ala Asp Tyr Tyr Cys Gly Thr Trp
    210                 215                 220

Asp Ser Ser Leu Ser Ala Leu Val Phe Gly Gly Thr Lys Val Thr
225                 230                 235                 240

Val Leu Gly

<210> SEQ ID NO 69
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Gln Gln Ser Gly Ala Glu Val Lys Thr Pro Gly Ser
1               5                   10                  15

Ser Val Lys Val Ser Cys Lys Ala Ser Gly Gly Thr Phe Arg Asn Asn
            20                  25                  30

Ala Ile Ser Trp Val Arg Gln Ala Pro Gly Gln Gly Leu Glu Trp Met
        35                  40                  45

Gly Gly Phe Ile Pro Lys Phe Gly Thr Thr Asn His Ala Gln Lys Phe
    50                  55                  60

Gln Gly Arg Val Thr Met Thr Ala Asp Asp Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Tyr Cys Gly Gly Gly Arg Cys Tyr Leu Tyr Gly
            100                 105                 110

Met Asp Val Trp Gly Gln Gly Thr Leu Val Thr Val Ser Ser Gly Gly
        115                 120                 125

Gly Gly Ser Gly Gly Gly Gly Ser Gly Gly Gly Gly Ser Ala Gln Ala
    130                 135                 140

Val Val Ile Gln Glu Pro Ser Leu Thr Val Ser Pro Gly Gly Thr Val
145                 150                 155                 160

Thr Leu Thr Cys Gly Ser Ser Thr Gly Ala Val Thr Ser Gly His Tyr
                165                 170                 175

Pro Tyr Trp Phe Gln Gln Lys Pro Gly Gln Ala Pro Arg Thr Leu Ile
            180                 185                 190

Tyr Asp Thr Ser Asn Lys Arg Ser Trp Thr Pro Ala Arg Phe Ser Gly
        195                 200                 205

Ser Leu Leu Gly Gly Lys Ala Ala Leu Thr Leu Ser Gly Ala Gln Pro
    210                 215                 220

Glu Asp Glu Ala Glu Tyr Tyr Cys Leu Val Ser Tyr Ser Gly Ser Leu
225                 230                 235                 240

Val Val Phe Gly Gly Gly Thr Lys Leu Thr Val Leu Gly
                245                 250

<210> SEQ ID NO 70
<211> LENGTH: 243
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Ala Trp Leu Asp Tyr Trp Gly Arg Gly Thr Met Val Thr
            100                 105                 110

Val Ser Ser Gly Gly Gly Gly Ser Gly Gly Gly Gly Ser Gly Gly Gly
        115                 120                 125

Gly Ser Ala Leu Asn Phe Met Leu Thr Gln Pro His Ser Val Ser Glu
    130                 135                 140

Ser Pro Gly Lys Thr Val Thr Ile Ser Cys Thr Gly Ser Ser Gly Ser
145                 150                 155                 160

Val Ala Arg Asn Tyr Val Gln Trp Tyr Gln Gln Arg Pro Gly Ser Ala
                165                 170                 175

Pro Thr Ile Val Ile Tyr Glu Asp Asn Arg Arg Pro Ser Gly Val Pro
            180                 185                 190

Gly Arg Phe Ser Gly Ser Ile Asp Arg Ser Ser Asn Ser Ala Ser Leu
        195                 200                 205

Thr Ile Ser Gly Leu Gln Thr Glu Asp Glu Ala Asp Tyr Tyr Cys Gln
    210                 215                 220

Ser Tyr Asn Tyr Asn Thr Trp Val Phe Gly Gly Gly Thr Lys Leu Thr
225                 230                 235                 240

Val Leu Gly

<210> SEQ ID NO 71
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Ser Tyr
            20                  25                  30

Gly Ile Thr Trp Val Arg Gln Ala Pro Gly Gln Gly Leu Glu Trp Met
        35                  40                  45

Gly Trp Ile Ser Ala Tyr Asn Gly Lys Thr Asn Tyr Val Gln Glu Leu
    50                  55                  60

Gln Gly Arg Val Thr Met Thr Thr Asp Thr Ser Thr Ser Thr Val Tyr
65                  70                  75                  80

Met Glu Leu Thr Ser Leu Arg Ser Asp Asp Thr Ala Val Tyr Tyr Cys

```
            85                  90                  95
Ala Arg Arg Gly Asn Asn Tyr Arg Phe Gly Tyr Phe Asp Phe Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Ala Leu Glu Thr Thr Leu Thr Gln
        130                 135                 140

Ser Pro Gly Thr Leu Ser Leu Ser Pro Gly Glu Arg Ala Thr Leu Ser
145                 150                 155                 160

Cys Arg Ala Ser Gln Ser Ile Ser Ser Asn Leu Ala Trp Tyr Gln
                165                 170                 175

Gln Lys Pro Gly Arg Ala Pro Arg Leu Leu Ile Tyr Gly Ala Ser Ser
                180                 185                 190

Arg Ala Ile Gly Ile Pro Asp Arg Phe Ser Gly Ser Gly Ser Gly Thr
            195                 200                 205

Asp Phe Thr Leu Thr Ile Ser Arg Leu Glu Ala Glu Asp Phe Ala Val
            210                 215                 220

Tyr Tyr Cys Gln Gln Tyr Gly Ser Ser Pro Ile Thr Phe Gly Gln Gly
225                 230                 235                 240

Thr Arg Leu Glu Ile Lys Arg
                245
```

<210> SEQ ID NO 72
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Thr
            20                  25                  30

Thr Val Ala Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Lys Ser Arg Ile Thr Ile Asn Val Asp Thr Ser Lys Asn
65                  70                  75                  80

Gln Ile Ser Leu Gln Leu Asn Ser Val Thr Pro Glu Asp Thr Ala Val
                85                  90                  95

Tyr Tyr Cys Ala Arg Glu Pro Asp Ala Gly Arg Gly Ala Phe Asp Ile
            100                 105                 110

Trp Gly Gln Gly Thr Thr Val Thr Ser Pro Leu Arg Trp Gly Arg Phe
        115                 120                 125

Gly Trp Arg Gly Leu Gly Arg Gly Trp Leu Arg Ser Pro Val Thr Gln
    130                 135                 140

Ser Pro Gly Thr Leu Ser Leu Ser Pro Gly Glu Arg Ala Thr Leu Ser
145                 150                 155                 160

Cys Arg Ala Ser Gln Ser Val Ser Ser Ser His Leu Ala Trp Tyr Gln
                165                 170                 175

Gln Lys Pro Gly Gln Ala Pro Arg Leu Leu Ile Tyr Gly Ala Ser Ser
                180                 185                 190
```

```
Arg Ala Thr Gly Ile Pro Asp Arg Phe Ser Gly Ser Gly Ser Gly Thr
            195                 200                 205

Asp Phe Thr Leu Thr Ile Ser Ser Leu Glu Pro Glu Asp Phe Ala Val
210                 215                 220

Tyr Tyr Cys Gln Gln Arg Ser Asn Trp Pro Pro Arg Ala Val Phe Gly
225                 230                 235                 240

Gln Gly Thr Arg Leu Glu Ile Lys
            245
```

<210> SEQ ID NO 73
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Gln Val Gln Leu Gln Gln Ser Gly Pro Gly Arg Val Gln Pro Ser Gln
1               5                   10                  15

Thr Leu Ser Leu Thr Cys Ala Ile Ser Gly Asp Ser Val Ser Asn Asn
            20                  25                  30

Asn Ala Ala Trp Tyr Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Ser Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Gly Asp Gly Asn Ser Tyr Phe Asp Tyr Trp
            100                 105                 110

Gly Gln Gly Thr Leu Val Thr Val Ser Ser Gly Ile Leu Arg Trp Gly
        115                 120                 125

Arg Phe Gly Trp Arg Gly Leu Gly Arg Gly Trp Leu Glu Ile Val Leu
130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Gly Tyr Val Ser Trp
                165                 170                 175

Tyr Arg Gln Lys Pro Gly Gln Ala Pro Arg Leu Leu Ile Tyr Gly Ala
            180                 185                 190

Ser Thr Arg Ala Thr Gly Ile Pro Asp Arg Phe Ser Gly Ser Gly Ser
        195                 200                 205

Gly Thr Asp Phe Thr Leu Thr Ile Ser Arg Leu Glu Pro Glu Asp Phe
210                 215                 220

Ala Val Tyr Tyr Cys His Gln Tyr Gly Ser Ser Pro Asn Thr Tyr Gly
225                 230                 235                 240

Gln Gly Thr Lys Val Gly Ile Lys
            245
```

<210> SEQ ID NO 74
<211> LENGTH: 452
<212> TYPE: PRT
<213> ORGANISM: Homo sapiens

<400> SEQUENCE: 74

-continued

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
    195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
    275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
    355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
```

```
              420               425               430
Gly Lys Pro Thr Leu Tyr Asn Val Ser Leu Val Met Ser Asp Thr Ala
        435                 440                 445
Gly Thr Cys Tyr
    450

<210> SEQ ID NO 75
<211> LENGTH: 1347
<212> TYPE: DNA
<213> ORGANISM: Homo sapiens

<400> SEQUENCE: 75
gccccaaccc ttttcccct cgtctcctgt gagaattccc cgtcggatac gagcagcgtg      60
gccgttggct gcctcgcaca ggacttcctt cccgactcca tcactttctc ctggaaatac    120
aagaacaact ctgacatcag cagcacccgg ggcttcccat cagtcctgag aggggggcaag   180 cacgcagcca cctcacaggt gctgctgcct tccaaggacg tcatgcaggg cacagacgaa    240
cacgtggtgt gcaaagtcca gcaccccaac ggcaacaaag aaagaacgt gcctcttcca     300 gtgattgctg agctgcctcc caaagtgagc gtcttcgtcc caccccgcga cggcttcttc    360
ggcaaccccc gcaagtccaa gctcatctgc caggccacgg gtttcagtcc ccggcagatt    420
caggtgtcct ggctgcgcga ggggaagcag gtggggtctg gcgtcaccac ggaccaggtg    480
caggctgagg caaaggagtc tgggaccacg acctacaagg tgaccagcac actgaccatc    540
aaagagagcg actggctcag ccagagcatg ttcacctgcc gcgtggatca gggggcctg     600 accttccagc agaatgcgtc ctccatgtgt ggccccgatc aagacacagc catccgggtc    660
ttctccatcc ccccatcctt tgccagcatc ttcctcacca gtccaccaa gttgacctgc     720 ctggtcacag acctgaccac ctatgacagc gtgaccatct cctggacccg ccagaatggc    780
gaagctgtga aacccacac caacatctcc gagagccacc ccaatgccac tttcagcgcc    840
gtgggtgagg ccagcatctg cgaggatgac tggaattccg gggagaggtt cacgtgcacc    900
gtgacccaca cagacctgcc ctcgccactg aagcagacca tctcccggcc caagggggtg    960
gccctgcaca ggccccgatgt ctacttgctg ccaccagccc gggagcagct gaacctgcgg   1020
gagtcggcca ccatcacgtg cctggtgacg gcttctctc ccgcggacgt cttcgtgcag     1080
tggatgcaga gggggcagcc cttgtccccg gagaagtatg tgaccagcgc ccaatgcct    1140 gagccccagg ccccaggccg gtacttcgcc cacagcatcc tgaccgtgtc cgaagaggaa   1200
tggaacacgg gggagaccta cacctgcgtg gtgcccatg aggccctgcc caacagggtc    1260
accgagagga ccgtggacaa gtccaccggt aaacccaccc tgtacaacgt gtccctggtc   1320
atgtccgaca cagctggcac ctgctac                                        1347

<210> SEQ ID NO 76
<211> LENGTH: 159
<212> TYPE: PRT
<213> ORGANISM: Homo sapiens

<400> SEQUENCE: 76

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45
```

```
Glu Asp Pro Asn Glu Asp Ile Val Glu Arg Asn Ile Arg Ile Val
     50                  55                  60
Pro Leu Asn Asn Arg Glu Asn Ile Ser Asp Pro Thr Ser Pro Leu Arg
 65                  70                  75                  80
Thr Arg Phe Val Tyr His Leu Ser Asp Leu Cys Lys Lys Cys Asp Pro
                 85                  90                  95
Thr Glu Val Glu Leu Asp Asn Gln Ile Val Thr Ala Thr Gln Ser Asn
                100                 105                 110
Ile Cys Asp Glu Asp Ser Ala Thr Glu Thr Cys Tyr Thr Tyr Asp Arg
            115                 120                 125
Asn Lys Cys Tyr Thr Ala Val Val Pro Leu Val Tyr Gly Gly Glu Thr
        130                 135                 140
Lys Met Val Glu Thr Ala Leu Thr Pro Asp Ala Cys Tyr Pro Asp
145                 150                 155
```

<210> SEQ ID NO 77
<211> LENGTH: 480
<212> TYPE: DNA
<213> ORGANISM: Homo sapiens

<400> SEQUENCE: 77

```
atgaagaacc atttgctttt ctggggagtc ctggcggttt ttattaaggc tgttcatgtg       60
aaagcccaag aagatgaaag gattgttctt gttgacaaca atgtaagtg tgcccggatt      120
acttccagga tcatccgttc ttccgaagat cctaatgagg acattgtgga gagaaacatc     180
cgaattattg ttcctctgaa caacagggag aatatctctg atcccacctc accattgaga     240
accagatttg tgtaccattt gtctgacctc tgtaaaaaat gtgatcctac agaagtggag     300
ctggataatc agatagttac tgctacccag agcaatatct gtgatgaaga cagtgctaca     360
gagacctgct acacttatga cagaaacaag tgctacacag ctgtggtccc actcgtatat     420
ggtggtgaga ccaaaatggt ggaaacagcc ttaaccccag atgcctgcta tcctgactaa     480
```

<210> SEQ ID NO 78
<211> LENGTH: 353
<212> TYPE: PRT
<213> ORGANISM: Homo sapiens

<400> SEQUENCE: 78

```
Ala Ser Pro Thr Ser Pro Lys Val Phe Pro Leu Ser Leu Cys Ser Thr
  1               5                  10                  15
Gln Pro Asp Gly Asn Val Val Ile Ala Cys Leu Val Gln Gly Phe Phe
                 20                  25                  30
Pro Gln Glu Pro Leu Ser Val Thr Trp Ser Glu Ser Gly Gln Gly Val
             35                  40                  45
Thr Ala Arg Asn Phe Pro Pro Ser Gln Asp Ala Ser Gly Asp Leu Tyr
     50                  55                  60
Thr Thr Ser Ser Gln Leu Thr Leu Pro Ala Thr Gln Cys Leu Ala Gly
 65                  70                  75                  80
Lys Ser Val Thr Cys His Val Lys His Tyr Thr Asn Pro Ser Gln Asp
                 85                  90                  95
Val Thr Val Pro Cys Pro Val Pro Ser Thr Pro Pro Thr Pro Ser Pro
                100                 105                 110
Ser Thr Pro Pro Thr Pro Ser Pro Ser Cys Cys His Pro Arg Leu Ser
            115                 120                 125
Leu His Arg Pro Ala Leu Glu Asp Leu Leu Leu Gly Ser Glu Ala Asn
        130                 135                 140
```

```
Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 79
<211> LENGTH: 340
<212> TYPE: PRT
<213> ORGANISM: Homo sapiens

<400> SEQUENCE: 79

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160
```

```
Pro Pro Glu Arg Asp Leu Cys Gly Cys Tyr Ser Val Ser Ser Val Leu
            165                 170                 175

Pro Gly Cys Ala Gln Pro Trp Asn His Gly Glu Thr Phe Thr Cys Thr
        180                 185                 190

Ala Ala His Pro Glu Leu Lys Thr Pro Leu Thr Ala Asn Ile Thr Lys
    195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 80
<211> LENGTH: 764
<212> TYPE: PRT
<213> ORGANISM: Homo sapiens

<400> SEQUENCE: 80

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
```

```
            180                 185                 190
Leu Asp Ile Gln Gly Thr Gly Gln Leu Leu Phe Ser Val Val Ile Asn
            195                 200                 205

Gln Leu Arg Leu Ser Asp Ala Gly Gln Tyr Leu Cys Gln Ala Gly Asp
        210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Gly Ser Val Ala
        355                 360                 365

Val Leu Cys Pro Tyr Asn Arg Lys Glu Ser Lys Ser Ile Lys Tyr Trp
    370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605
```

Lys Ala Val Ala Asp Thr Arg Asp Gln Ala Asp Gly Ser Arg Ala Ser
610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
            645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
    690                 695                 700

Gln Glu Thr Ser Leu Gly Gly Lys Glu Phe Val Ala Thr Thr Glu
705                 710                 715                 720

Ser Thr Thr Glu Thr Lys Glu Pro Lys Ala Lys Arg Ser Ser Lys
            725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
        755                 760

<210> SEQ ID NO 81
<211> LENGTH: 585
<212> TYPE: PRT
<213> ORGANISM: Homo sapiens

<400> SEQUENCE: 81

Lys Ser Pro Ile Phe Gly Pro Glu Glu Val Asn Ser Val Glu Gly Asn
1               5                   10                  15

Ser Val Ser Ile Thr Cys Tyr Tyr Pro Pro Thr Ser Val Asn Arg His
            20                  25                  30

Thr Arg Lys Tyr Trp Cys Arg Gln Gly Ala Arg Gly Gly Cys Ile Thr
        35                  40                  45

Leu Ile Ser Ser Glu Gly Tyr Val Ser Ser Lys Tyr Ala Gly Arg Ala
50                  55                  60

Asn Leu Thr Asn Phe Pro Glu Asn Gly Thr Phe Val Val Asn Ile Ala
65                  70                  75                  80

Gln Leu Ser Gln Asp Asp Ser Gly Arg Tyr Lys Cys Gly Leu Gly Ile
            85                  90                  95

Asn Ser Arg Gly Leu Ser Phe Asp Val Ser Leu Glu Val Ser Gln Gly
            100                 105                 110

Pro Gly Leu Leu Asn Asp Thr Lys Val Tyr Thr Val Asp Leu Gly Arg
        115                 120                 125

Thr Val Thr Ile Asn Cys Pro Phe Lys Thr Glu Asn Ala Gln Lys Arg
130                 135                 140

Lys Ser Leu Tyr Lys Gln Ile Gly Leu Tyr Pro Val Leu Val Ile Asp
145                 150                 155                 160

Ser Ser Gly Tyr Val Asn Pro Asn Tyr Thr Gly Arg Ile Arg Leu Asp
            165                 170                 175

Ile Gln Gly Thr Gly Gln Leu Leu Phe Ser Val Val Ile Asn Gln Leu
            180                 185                 190

Arg Leu Ser Asp Ala Gly Gln Tyr Leu Cys Gln Ala Gly Asp Asp Ser
        195                 200                 205

Asn Ser Asn Lys Lys Asn Ala Asp Leu Gln Val Leu Lys Pro Glu Pro

```
            210                 215                 220
Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
                245                 250                 255

Ser Gly Glu Asn Cys Asp Val Val Asn Thr Leu Gly Lys Arg Ala
            260                 265                 270

Pro Ala Phe Glu Gly Arg Ile Leu Leu Asn Pro Gln Asp Lys Asp Gly
            275                 280                 285

Ser Phe Ser Val Val Ile Thr Gly Leu Arg Lys Glu Asp Ala Gly Arg
290                 295                 300

Tyr Leu Cys Gly Ala His Ser Asp Gly Gln Leu Gln Glu Gly Ser Pro
305                 310                 315                 320

Ile Gln Ala Trp Gln Leu Phe Val Asn Glu Glu Ser Thr Ile Pro Arg
                325                 330                 335

Ser Pro Thr Val Val Lys Gly Val Ala Gly Gly Ser Val Ala Val Leu
            340                 345                 350

Cys Pro Tyr Asn Arg Lys Glu Ser Lys Ser Ile Lys Tyr Trp Cys Leu
            355                 360                 365

Trp Glu Gly Ala Gln Asn Gly Arg Cys Pro Leu Leu Val Asp Ser Glu
370                 375                 380

Gly Trp Val Lys Ala Gln Tyr Glu Gly Arg Leu Ser Leu Leu Glu Glu
385                 390                 395                 400

Pro Gly Asn Gly Thr Phe Thr Val Ile Leu Asn Gln Leu Thr Ser Arg
                405                 410                 415

Asp Ala Gly Phe Tyr Trp Cys Leu Thr Asn Gly Asp Thr Leu Trp Arg
                420                 425                 430

Thr Thr Val Glu Ile Lys Ile Ile Glu Gly Glu Pro Asn Leu Lys Val
            435                 440                 445

Pro Gly Asn Val Thr Ala Val Leu Gly Glu Thr Leu Lys Val Pro Cys
            450                 455                 460

His Phe Pro Cys Lys Phe Ser Ser Tyr Glu Lys Tyr Trp Cys Lys Trp
465                 470                 475                 480

Asn Asn Thr Gly Cys Gln Ala Leu Pro Ser Gln Asp Glu Gly Pro Ser
                485                 490                 495

Lys Ala Phe Val Asn Cys Asp Glu Asn Ser Arg Leu Val Ser Leu Thr
                500                 505                 510

Leu Asn Leu Val Thr Arg Ala Asp Glu Gly Trp Tyr Trp Cys Gly Val
            515                 520                 525

Lys Gln Gly His Phe Tyr Gly Glu Thr Ala Ala Val Tyr Val Ala Val
            530                 535                 540

Glu Glu Arg Lys Ala Ala Gly Ser Arg Asp Val Ser Leu Ala Lys Ala
545                 550                 555                 560

Asp Ala Ala Pro Asp Glu Lys Val Leu Asp Ser Gly Phe Arg Glu Ile
                565                 570                 575

Glu Asn Lys Ala Ile Gln Asp Pro Arg
            580                 585

<210> SEQ ID NO 82
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 82

Met Asp Leu Met Cys Lys Lys Met Lys His Leu Trp Phe Phe Leu Leu
1               5                   10                  15

Leu Val Ala Ala Pro Arg Trp Val Leu Ser Gln Leu Gln Leu Gln Glu
            20                  25                  30

Ser Gly Pro Gly Leu Val Lys Pro Ser Glu Thr Leu Ser Leu Thr Cys
        35                  40                  45

Thr Val Ser Gly Gly Ser Ile Ile Ser Lys Ser Ser Tyr Trp Gly Trp
    50                  55                  60

Ile Arg Gln Pro Pro Gly Lys Gly Leu Glu Trp Ile Gly Ser Ile Tyr
65                  70                  75                  80

Tyr Ser Gly Ser Thr Phe Tyr Asn Pro Ser Leu Lys Ser Arg Val Thr
                85                  90                  95

Ile Ser Val Asp Thr Ser Lys Asn Gln Phe Ser Leu Lys Leu Ser Ser
            100                 105                 110

Val Thr Ala Ala Asp Thr Ala Val Tyr Tyr Cys Ala Arg Leu Thr Val
        115                 120                 125

Ala Glu Phe Asp Tyr Trp Gly Gln Gly Thr Leu Val Thr Val Ser Ser
    130                 135                 140

Ala Ser
145

<210> SEQ ID NO 83
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Phe Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Leu Thr Phe Gly Pro Gly Thr Lys Val Asp Ile Lys Arg
        115                 120                 125

Thr

<210> SEQ ID NO 84
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Met Asp Leu Met Cys Lys Lys Met Lys His Leu Trp Phe Phe Leu Leu
1               5                   10                  15
Leu Val Ala Ala Pro Arg Trp Val Leu Ser Gln Leu Gln Leu Gln Glu
                20                  25                  30
Ser Gly Pro Gly Leu Val Lys Pro Ser Glu Thr Leu Ser Leu Thr Cys
            35                  40                  45
Thr Val Ser Gly Gly Ser Ile Ser Ser Arg Ser Asn Tyr Trp Gly Trp
        50                  55                  60
Ile Arg Gln Pro Pro Gly Lys Gly Leu Glu Trp Ile Gly Asn Val Tyr
65                  70                  75                  80
Tyr Arg Gly Ser Thr Tyr Tyr Asn Ser Ser Leu Lys Ser Arg Val Thr
                85                  90                  95
Ile Ser Val Asp Thr Ser Lys Asn Gln Phe Ser Leu Lys Leu Ser Ser
            100                 105                 110
Val Thr Val Ala Asp Thr Ala Val Tyr Tyr Cys Ala Arg Leu Ser Val
        115                 120                 125
Ala Glu Phe Asp Tyr Trp Gly Gln Gly Ile Leu Val Thr Val Ser Ser
130                 135                 140
Ala Ser
145
```

<210> SEQ ID NO 85
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Met Glu Ala Pro Ala Gln Leu Leu Phe Leu Leu Leu Leu Trp Leu Pro
1               5                   10                  15
Asp Thr Thr Gly Glu Ile Val Leu Thr Gln Ser Pro Ala Thr Leu Ser
                20                  25                  30
Leu Ser Pro Gly Glu Arg Ala Thr Leu Ser Cys Arg Ala Ser Gln Ser
            35                  40                  45
Val Ser Ser Phe Leu Ala Trp Tyr Gln Gln Lys Pro Gly Gln Ala Pro
        50                  55                  60
Arg Leu Leu Ile Tyr Asp Ala Ser Asn Arg Ala Thr Gly Ser Pro Ala
65                  70                  75                  80
Arg Phe Ser Gly Ser Gly Ser Gly Thr Asp Phe Thr Leu Thr Ile Ser
                85                  90                  95
Ser Leu Glu Pro Glu Asp Phe Ala Val Tyr Tyr Cys Gln Gln Arg Ser
            100                 105                 110
Asp Trp Pro Leu Thr Phe Gly Pro Gly Thr Lys Val Asp Ile Lys Arg
        115                 120                 125
Thr
```

<210> SEQ ID NO 86
<211> LENGTH: 154
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Met Asp Leu Met Cys Lys Lys Met Lys His Leu Trp Phe Phe Leu Leu
1               5                   10                  15

Leu Val Ala Ala Pro Arg Trp Val Leu Ser Gln Leu Gln Leu Gln Glu
            20                  25                  30

Ser Gly Pro Gly Leu Val Lys Pro Ser Glu Thr Leu Ser Leu Thr Cys
        35                  40                  45

Thr Val Ser Gly Gly Ser Ile Ser Ser Ser Tyr Tyr Trp Gly Trp
50                  55                  60

Val Arg Gln Pro Pro Gly Lys Gly Leu Glu Trp Ile Gly Ser Ile His
65                  70                  75                  80

Tyr Ser Gly Ser Thr Phe Tyr Asn Pro Ser Leu Lys Ser Arg Val Thr
                85                  90                  95

Ile Ser Val Asp Thr Ser Lys Asn Gln Phe Ser Leu Lys Leu Ser Ser
            100                 105                 110

Val Thr Ala Ala Asp Thr Thr Val Tyr Tyr Cys Ala Arg Gln Gly Ser
        115                 120                 125

Thr Val Val Arg Gly Val Tyr Tyr Tyr Gly Met Asp Val Trp Gly Gln
130                 135                 140

Gly Thr Thr Val Thr Val Ser Ser Ala Ser
145                 150

<210> SEQ ID NO 87
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Leu Tyr Thr Phe Gly Gln Gly Thr Lys Leu Glu Ile
        115                 120                 125

Lys Arg Thr
    130

<210> SEQ ID NO 88
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88
```

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Ser Ser Tyr Ala Met Ser Trp Val Arg Gln Ala Pro Gly Lys Gly Leu
        50                  55                  60

Glu Trp Val Ser Ala Ile Ser Gly Ser Gly Gly Ser Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ser Ser Gly Trp Phe Gly Ala Phe Asp Tyr
        115                 120                 125

Trp Gly Gln Gly Thr Leu Val Thr Val Ser Ser
    130                 135
```

<210> SEQ ID NO 89
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
                20                  25                  30

Thr Pro Lys Glu Lys Val Thr Ile Thr Cys Arg Ala Ser Gln Ser Ile
            35                  40                  45

Gly Ser Ser Leu His Trp Tyr Gln Gln Lys Pro Asp Gln Ser Pro Lys
        50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Ile Thr Phe Gly Gln Gly Thr Arg Leu Glu Ile Lys Arg
        115                 120                 125
```